United States Patent
Ravins et al.

(10) Patent No.: US 6,432,035 B1
(45) Date of Patent: Aug. 13, 2002

(54) FIBEROPTIC-GUIDED INTERSTITIAL SEED MANUAL APPLICATOR AND CARTRIDGE

(75) Inventors: Steven S. Ravins, New York, NY (US); Edward Kaplan, Coral Springs, FL (US); Ernest A. Elgin, III, New Rochelle, NY (US)

(73) Assignee: Integrated Implant Systems, L.L.C., Arlington, VA (US)

( * ) Notice: Subject to any disclaimer, the term of this patent is extended or adjusted under 35 U.S.C. 154(b) by 0 days.

(21) Appl. No.: 09/512,452

(22) Filed: Feb. 24, 2000

Related U.S. Application Data

(62) Division of application No. 08/763,759, filed on Dec. 11, 1996, now Pat. No. 6,102,844.
(60) Provisional application No. 60/008,791, filed on Dec. 18, 1995, and provisional application No. 60/009,949, filed on Jan. 16, 1996.

(51) Int. Cl.⁷ .................................................. A61N 5/00
(52) U.S. Cl. ............................ 600/7; 604/57; 604/59; 604/60; 604/62
(58) Field of Search ................... 600/3, 7, 8, 101, 600/104, 108, 121, 125, 137, 160, 162, 178, 179; 604/57, 61, 62, 64, 59, 60; 221/69, 79, 80, 81

(56) References Cited

U.S. PATENT DOCUMENTS

| | | |
|---|---|---|
| 1,347,622 A | 7/1920 | Deininger |
| 2,269,963 A | 1/1942 | Wappler |
| 3,750,653 A | 8/1973 | Simon |
| 4,086,914 A | 5/1978 | Moore |
| 4,167,179 A | 9/1979 | Kirsch |
| 4,402,308 A * | 9/1983 | Scott .......................... 600/7 |
| 4,461,280 A | 7/1984 | Baumgartner |
| 4,586,490 A | 5/1986 | Katz |
| 4,697,575 A | 10/1987 | Horowitz |
| 4,700,692 A | 10/1987 | Baumgartner |
| 4,762,515 A | 8/1988 | Grimm ........................ 604/61 |
| 4,763,642 A | 8/1988 | Horowitz |
| 4,897,076 A | 1/1990 | Puthawala et al. |
| 5,084,001 A | 1/1992 | Van't Hooft et al. |
| 5,135,493 A * | 8/1992 | Peschke ...................... 604/61 |
| 5,147,282 A | 9/1992 | Kan |
| 5,147,295 A | 9/1992 | Stewart |
| 5,242,373 A | 9/1993 | Scott et al. |
| 5,282,781 A | 2/1994 | Liprie |
| 5,300,080 A | 4/1994 | Clayman et al. |
| 5,310,407 A | 5/1994 | Casale |

FOREIGN PATENT DOCUMENTS

| | | |
|---|---|---|
| DE | 41 09 205 | 9/1992 |
| EP | 077 145 | 4/1983 |
| EP | 466 681 | 1/1992 |
| EP | 642 762 | 3/1995 |
| EP | 0642 764 | 3/1995 |
| EP | 668 088 | 8/1995 |
| EP | 677 278 | 10/1995 |
| GB | 786 850 | 11/1957 |
| WO | 88/06905 | 9/1988 |

OTHER PUBLICATIONS

Derwent English–language Abstract of EPO 466 681.
Derwent English–language Abstract of EPO 677 278.
Derwent English–language Abstract of DE 41 09 205.

(List continued on next page.)

*Primary Examiner*—R Kearney
(74) *Attorney, Agent, or Firm*—Foley & Lardner

(57) ABSTRACT

A method for implanting seeds in or about a target area, such as a tumor, within a patient. The implantation device includes an implantation needle having a bore extending longitudinally therethrough from a proximal end to a distal end of the needle, the needle bore being adapted to permit at least one seed to pass therethrough. An elongated plunger extends longitudinally through the implantation device in aligned relation to the needle bore. An optical device is carried by and operatively connected to the plunger to provide visual assistance to an operator of the implantation device to guide and verify implantation of the ejected seed into the target area.

10 Claims, 28 Drawing Sheets

OTHER PUBLICATIONS

H.J. Hodt et al., "A Gun for Interstitial Implatntion of Radioactive Gold Grains", *British Journal of Radiology*, pp. 419–421 (date of publication unknown).

L. Delclos et al., "A slim gold–grain implatned loaded with Standard Royal Marsden 14–grain magazines", *Cancer* 43:1022, 1979 (Figs. 11:12 and 11:13).

W.U. Shipley et al., "Iodine–125 Implant and External Beam . . . Pancreatic Carconoma", *Cancer*, vol. 45, pp. 709–714, Feb. 1980.

L. Delclos, "A second look at interstitial irradiation", *Topical Rev. in Radio. And Onco. –Z*, 1982 (Fig. 11–48).

J.J. Batterman et al., "Interstitial Therapy . . . Bladder Tumors", *Endo/Hypo. Onc.*, vol. 4, pp. 1–6, 1/88.

D. Donath et al., "Brachytherapy in the Treatment . . . Metastases to the Liver", *J Surg. Onc.*, vol. 44, pp. 55–61, 1990.

J.W. Lewis et al., "Role of Brachytherapy in the Management of Pulmonary and Mediastinal Malignancies", *Ann Thorac Surgery*, vol. 49, pp. 728–733, 1990.

Abstract, Y. Maruyama et al., "In Situ Predictive Assay Using Cervical Cancer Preoperative Radiation Therapy", *Endocurie, Hypertherm, Oncol..*, vol. 9, p. 60, 1993.

Abstract, J. Fontanesi et al., "Pediatric Brachytherapy: Update of St. Jude Children's Research Hospital Experience", *Endocurie, Hypertherm. Oncol.*, vol. 9, p. 60, Jan. 1993.

Abstract, J.G. Armstrong et al., "Brachytherapy of Colorectal Liver Metastases", *Endocurie, Hypertherm. Oncol.*, vol. 9, pp. 60–61, Jan. 1993.

J.M. Childers et al., Laparascopically Assisted Transperineal Interstitial Irradiation and Surgical . . . Cervical Carcinoma, *Endocurie, Hypertherm. Onco.*, vol. 10, pp. 83–86, Apr. 1994.

M. Mohiuddin et al., "Carcinoma of the pancreas—the Jefferson experience 197501988", *European J. Surg. Onco.*, vol. 20, pp. 13–20, 1994.

N. Subir et al., "Survey of Brachytherapy Practice in the United States . . . American Endocurietherapy Society", *Int. J. Radiation Onc. Biol. Phys*, vol. 31:1, pp. 103–107, 1995.

R.G. Middleton et al., "Prostate Cancer Clinical Guidelines . . . Localized Prostate Cancer", *J. Urology*, vol. 154, pp. 2144–2148, Dec. 1995.

Cancer of the Prostate, pp. 1049, 1089–1097 (date of publication unknown).

Communication Relating to the Results of the Partial International Search Corresponding to PCT/US96/19620.

Copy of PCT International Search Report Corresponding to the International Application No. PCT/US96/19620.

\* cited by examiner

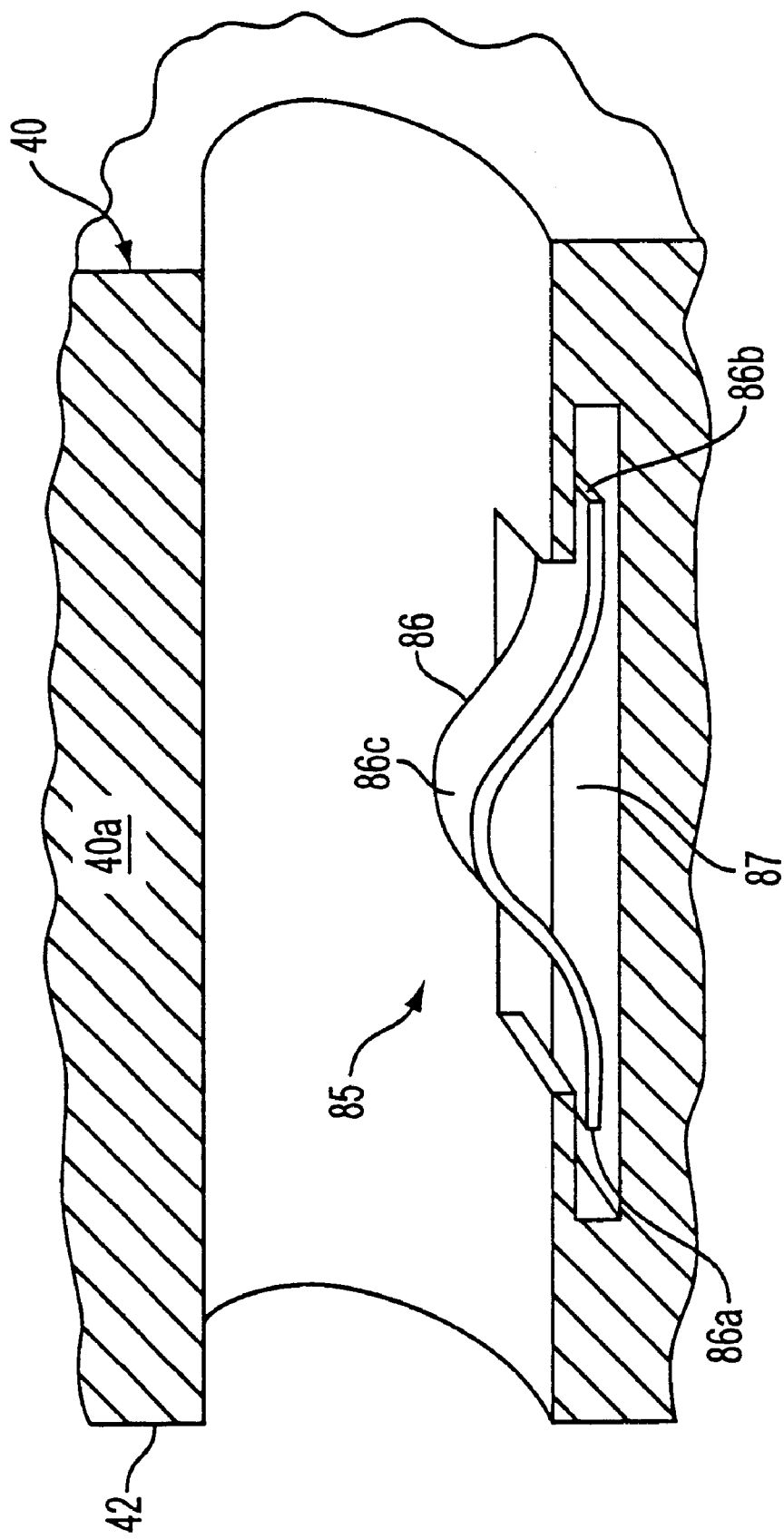

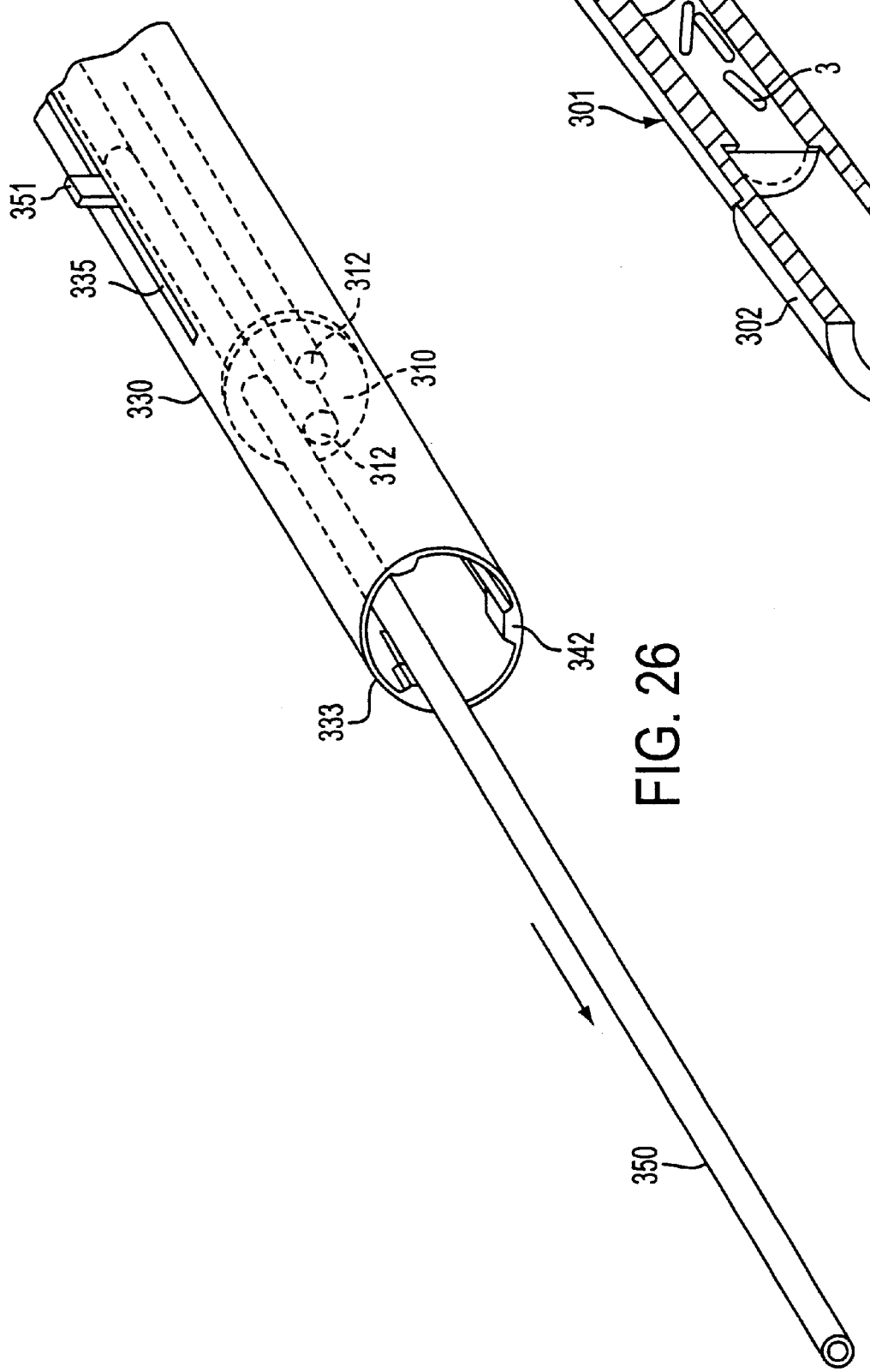

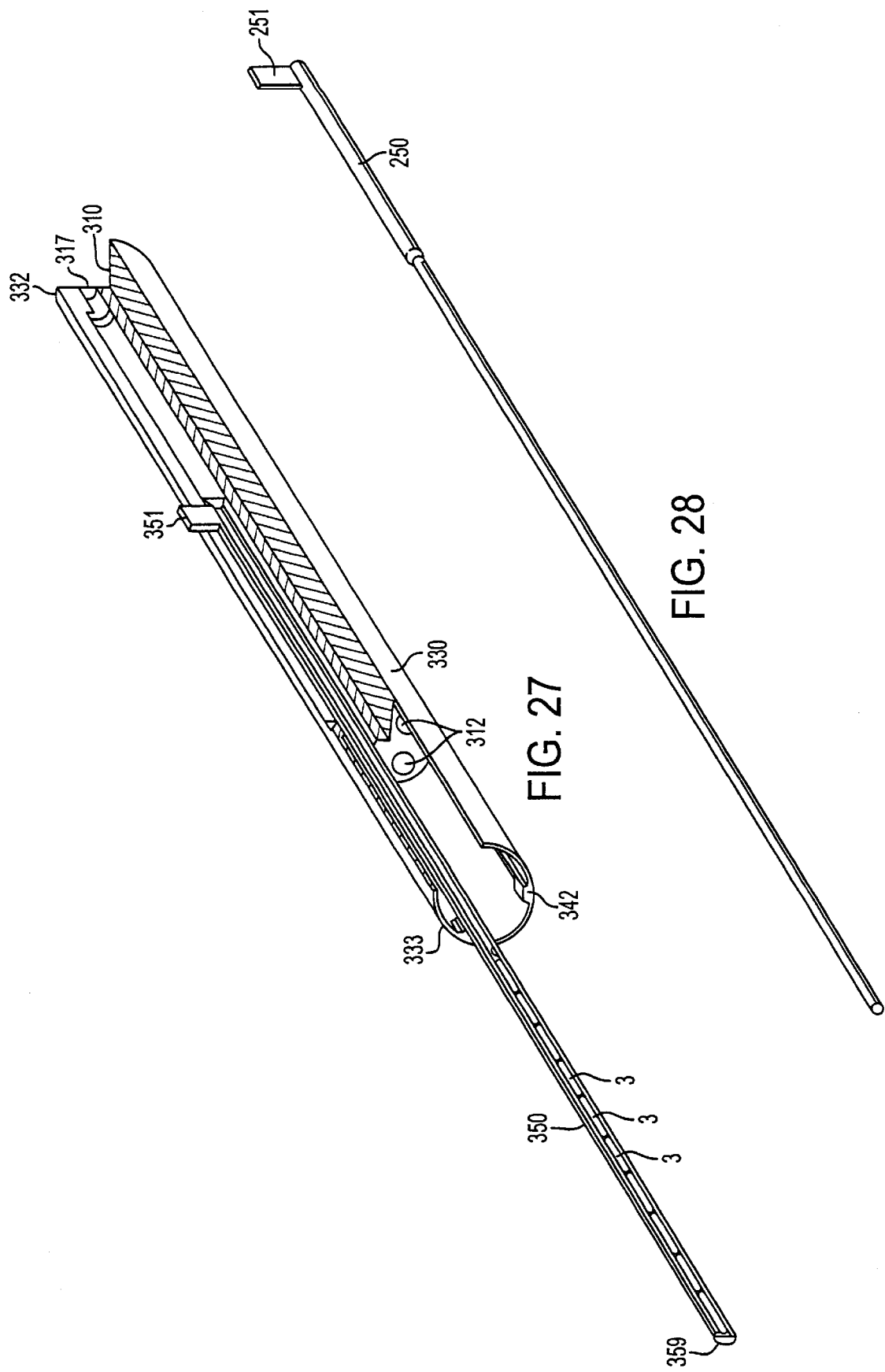

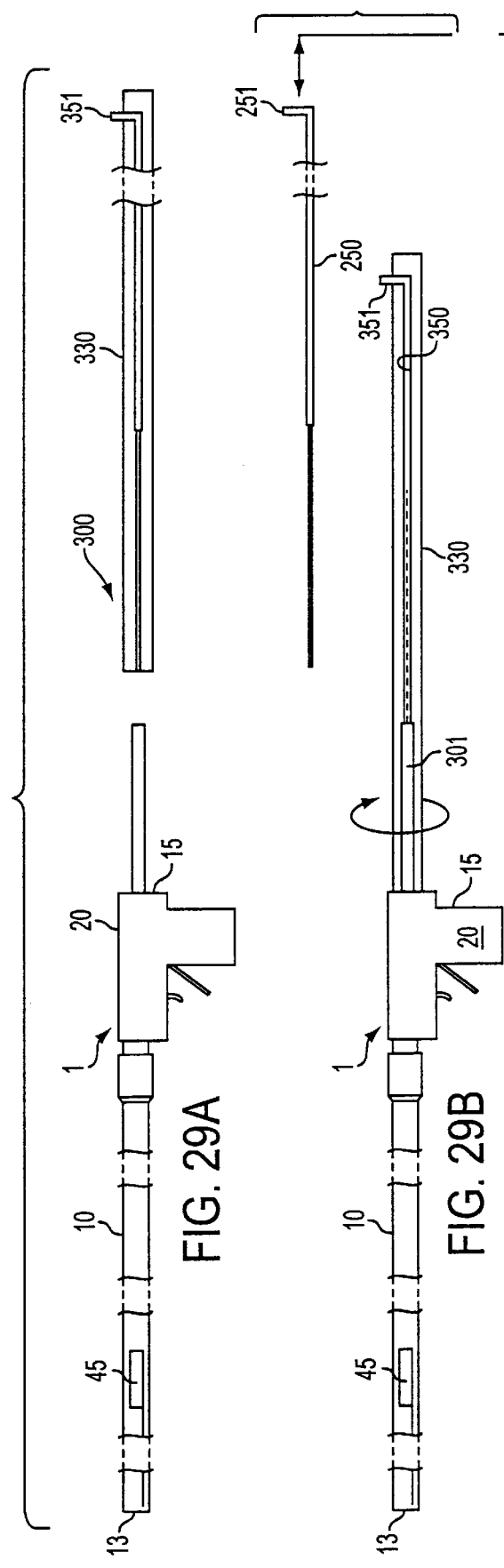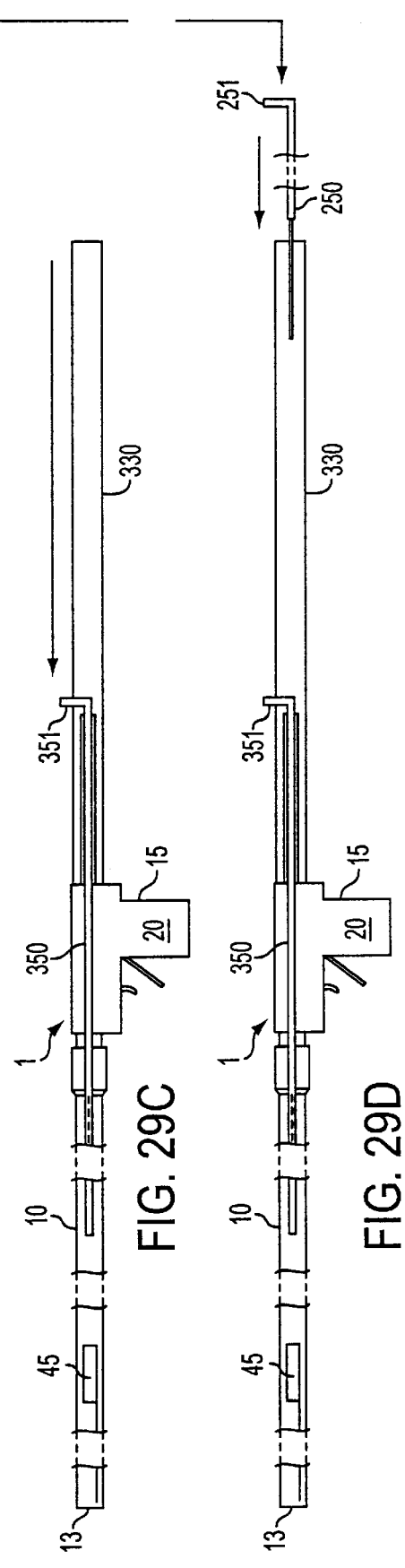
FIG. 29A
FIG. 29B
FIG. 29C
FIG. 29D

FIBEROPTIC-GUIDED INTERSTITIAL SEED MANUAL APPLICATOR AND CARTRIDGE

This application is a Divisional of Ser. No. 08/763,759, which was filed Dec. 11, 1996, U.S. Pat. No. 6,102,844 Aug. 15, 2000, which claims benefit to U.S. Provisional application Ser. No. 60/008,791, filed Dec. 12, 1995 and claims benefit to U.S. provisional application Ser. No. 60/009,949, filed Jan. 16, 1996.

BACKGROUND OF THE INVENTION

1. Field of the Invention

The present invention relates generally to the field of medical implantation devices and, more particularly, to an improved fiberoptic-guided interstitial seed manual applicator and seed cartridge.

2. Description of the Related Art

Afterloading brachytherapy has been in use since 1960 when it was pioneered in the United States by Ulrich Henschke. In this medical procedure, malignant tumors, and the like are treated by surgically implanting radioactive sources ("seeds") in or about the malignant tumor in order to irradiate the malignancy. The term "seeds" as used herein is intended to broadly mean an object or body to be implanted within a patient, including, but not limited to radioactive seeds used in brachytherapy procedures.

A variety of different radioactive materials have been used as seeds. For instance, Basil Hilaris was the first to use Iodine-125 for permanent implantation in a tumor. Since then, use of Iodine-125 has persisted, serving as the seeds used in the vast majority of interstitial brachytherapy implants for a host of tissues and organs. More recently, Palladium-103 has been approved for use as an implantable radionuclide and applications using Palladium-103 continue to be explored. Other radioactive materials that have also been used include Radon-222, Gold-198 and Iridium-192.

Precise location and spacing of the implanted seeds is of particular importance in the treatment of such malignant tumors and the like. Poor location or distribution of seeds can result in undesirable concentrations of seeds leading to either an overdosage or underdosage of radiation. As such, conventional interstitial seed implantation is frequently performed through an open surgical incision in the patient. In one conventional technique, hollow needles are inserted into the tumor and the seed are thereafter placed in the needles while the needles are being retracted to implant or deposit the seeds in the tumor. Popular instruments commonly used today for surgically implanting seeds in or about the tumor include the Henschke, Fletcher-Suit, and Mick applicators, Royal Marsden gold grain gun, and stainless steel needles/hairpins. With few exceptions, however, the basic concept and design behind most of these seed implantation systems have changed little over the years.

In contract, the last two decades have witnessed remarkable advances in surgical, imaging, and anesthetic practices, as well as new developments in permanent radionuclide source availability. Despite the fact that many surgical procedures are currently accomplished using conventional endoscopes or laparoscopes with minimal or limited incisions into chest, abdominal or pelvic wall tissue, conventional implantation systems have generally failed to combine such a technique with brachytherapy implantation due to a dearth in brachytherapy technology.

While many problems associated with interstitial seed implantation have been addressed by the above-mentioned conventional implantation instruments, there remains a tremendous need to develop an interstitial seed manual applicator that utilizes fiberoptics and is capable of precise implantation of seeds using minimal or limited incisions into chest, abdominal, or pelvic wall tissue of a patient.

In addition, seed handling in connection with brachytherapy has not changed since the inception of this therapeutic approach thirty years ago. Seeds may be ordered from a distributor and typically arrive loose in a protective lead-lined pig. Seed strength and number of seeds are generally communicated on the appropriate paperwork accompanying the seeds. Following delivery of the seeds, however, all further seed handling duties are typically accomplished manually by the radiation oncologist or related technical staff. These duties include seed counting; loading seeds into the appropriate cartridge, needle, or magazine; sterilizing the seeds in their receptacle for use in the operating suite; keeping a running tally of the number of dispensed seeds in the operating room with paper and pencil; surveying the operating suite following the procedure in order to track possible loose or stray seeds; and frequent switching of empty seed cartridges, needles, and magazine due to limited seed capacity.

Not only is this current seed handling procedure labor-intensive, but it invariably leads to radiation exposure of the personnel involved. In the best of circumstances, seeds can jam or dislodge from their receptacle and become temporarily or permanently misplaced. Sterilization of seeds intraoperatively wastes precious time and maintaining an accurate seed tally can be confusing. Accordingly, there is a tremendous need to develop a device that simplifies seed handling in connection with brachytherapy and minimizes the above-mentioned problems associated with current techniques.

SUMMARY OF THE INVENTION

By the use of the present invention, it is no longer necessary to limit brachytherapy applications or other implantation procedures to instances involving large, open surgical wounds or incisions. Rather, seed implantation may be achieved with fiberoptic or other optical assistance through a small incision associated most commonly with minimally-invasive surgery, as well as with the traditional large, open surgical incision. In addition, the fiberoptic or other optical assistance provided in accordance with the present invention facilitates accurate seed implantation into the target tissue using direct visualization of the seed passing into the tissue. Such an advance in seed implantation technology as a result of the present invention will broaden the applicability of interstitial implantation to include those patients who undergo fiberoptic-guided tumor biopsy and ordinarily would be sent for external beam radiotherapy thereafter; patients who medically cannot tolerate a large incisional wound; patients who are poor operative candidates based on technical considerations, such as those who have been previously irradiated with external beam therapy and whose tissues would heal poorly with additional radical surgery; patients with recurrences following either surgery or radiation therapy; or patients in whom minimally-invasive interstitial implantation is deemed advantageous. The unique feature of the implantation technique and manual applicator according to the present invention, including its fiberoptic guidance, minimally-invasive surgical requirement, automatic firing mechanism; gravity-independent posture, and integral dispensed/remaining seed visual indicator all serve to enhance the attractiveness and utility of interstitial brachytherapy, in general, and of this novel system in particular.

The foregoing and other objects and advantages are achieved in accordance with the present invention through the provision of a fiberoptic-guided interstitial seed manual applicator (FOGISMA) or implantation device. According to the present invention, a method and system is provided for interstitial implantation into or around neoplasms of tumoricidal or tumoristatic doses of radiation carried by radioactive seeds whose placement is guided via an intrinsic fiberoptic or optical component, potentially, but not necessarily, enhanced by laparoscopic, thoracoscopic, bronchoscopic, cystoscopic, or other types of assisted surveillance including direct vision. The FOGISMA device according to the present invention may require minimally invasive surgery in order to introduce the applicator through a small incision into the target issue, rather than the wide incision required by previous techniques.

With proper mounting, the FOGISMA device according to the present invention may also be used for percutaneous seed implantation, such as through the transperineal route for implanting the prostate gland. The same automatic firing mechanism and precision needle positioning as with the minimally invasive technique would apply, with the advantage of knowing the exact location of the needle tip by fiberoptic guidance. The radioactive seeds are introduced one at a time from a shielded seed magazine down the barrel of the applicator into the target tissue using a gravity-independent automatic firing mechanism instead of the conventional manual plunger, and the introducing needle is automatically withdrawn the desired amount by the precision FOGISMA device. Seeds may be placed sequentially along a given needle track and/or in separate needle tracks, while maintaining an integral visual numerical indication of all dispensed/remaining seeds.

In accordance with the present invention, all implantation device is provided for implanting seeds within or adjacent to a target area, such as a tumor, located within a patient. The implantation device comprises an implantation needle having a bore extending longitudinally therethrough from a proximal end to a distal end of the needle. The needle bore is adapted to permit at least one seed to pass therethrough into the target area. An elongated plunger extends longitudinally through the implantation device in aligned relation to the needle bore and is selectively movable in the longitudinal direction relative the needle from a retracted position spaced apart from the needle to an extended position wherein the plunger is advanced through the needle bore to eject at least one of the seeds through the bore, out of the distal end of the needle and into the target area. An optical device is carried by an operatively connected to the plunger to provide visual assistance to an operator of the implantation device to guide and verify implantation of the ejected seed into the target area.

THE FOGISMA implantation device of the present invention may also comprise: (1) a multi-seed cartridge, either pre-packaged or loaded ad hoc, which is inserted into the proximal end of the device; (2) an operational/controlling proximal end with a grip that allows the user, manually or with robotic assistance, to adjust and guide each motion related to seed placement; (3) a rotating loading barrel in the mid portion of the device that assures precise transfer of each individual seed from the loading chamber into the firing chamber (4) an introducer needle attached to the distal portion of the device that is effectively exposed from a protective sheath, enabling the needle to be driven into or around the tumor, thus providing a channel for seed insertion; (5) an outer sheath that functions as a protective housing for the introducer needle in its resting position and is adjustable to appropriate shorter lengths as required to permit a given length of the introducer needle to protrude for desired tissue penetration. Upon firing a radioactive seed into tissue, the subsequent seed in the seed cartridge will automatically shift into firing position, permitting easy and rapid firing of any number of seeds deemed appropriate. Additional seed cartridges may be required and can be exchanged for exhausted cartridges as necessary.

The present invention further addresses the glaring shortcomings of conventional seed handling in a way that will facilitate the user of the therapeutic modality of both seasoned practitioners and those who have been reluctant to attempt it in the past because of it inherent disadvantages. A Brachytherapy Interstitial Seed Cartridge (BISC) is provided in accordance with the present invention to hold a plurality of seeds for use with an implantation device of the type having a seed alignment channel, a hollow needle and a moveable plunger that causes seeds within the device to pass through the hollow needle and be implanted within or adjacent to a target area, such as a tumor, located within a patient. The seed cartridge comprises an elongated cylindrically-shaped core member having a seed conduit extending longitudinally therethrough, the seed conduit being adapted to retain the plurality of seeds in end-to-end aligned relation prior to feeding the seeds into the seed alignment channel of the implantation device. Locking means are provided to releasably connect the core member to the implantation device so that the seed conduit is in aligned relation to and communication with the seed alignment channel of the implementation device. As elongated seed advancement push rod is slidably received within the seed conduit to move longitudinally within the seed conduit to cause the seeds contained within the seed conduit to advance into the seed alignment channel of the implementation device from the seed cartridge.

The BISC seed cartridge may be a preloaded, self-contained seed cartridge for brachytherapy or other operators and is adaptable for a host of implant applicators. This delivery system comprises of a protective outer casing that stores a pre-sterilized cartridge containing the seeds. The easy-lock and unloading of the seed cartridge facilitates implantation by: 1) precluding exposure to staff before the implant; (2) ensuring a verified seed count; (3) eliminating the potential for seed spills or inadvertent loss due to seed manipulation in the brachytherapy room or operating suite; (4) efficient use of physician and operating room time by eliminating the need for autoclaving of the seeds/cartridge before use in the operating suite; (5) allowing rapid deposition of seeds that are preloaded with many more seeds per cartridge than the standard number allowed by today's seed magazines; and (6) limiting the potential for seed jamming or other misapplication through the smooth mechanical action of the seed cartridge.

The foregoing specific objects and advantages of the invention are illustrative of those that can be achieved by the present invention and are not intended to be exhaustive or limiting of the possible advantages which can be realized. Thus, these and other objects and advantages of this invention will be apparent from the description herein or can be learned from practicing this invention, both as embodied herein or as modified in view of any variations which may be apparent to those skilled in the art. Accordingly, the present invention resides in the novel parts, constructions, arrangements, combinations and improvements herein shown and described.

BRIEF DESCRIPTION OF THE DRAWINGS

The foregoing features and other aspects of the invention are explained in the following description taken in connection with the accompanying drawings wherein:

FIG. 13 is a side elevational view illustrating the seed lock mechanism of the fiberoptic-guided interstitial seed manual applicator illustrated in FIG. 5;

FIG. 25 is a cross-sectional view of the alignment adaptor/seed repository illustrated in FIG. 24;

FIG. 26 is a partial perspective view of the seed cartridge illustrated in FIG. 22;

FIG. 27 is a cross-sectional view of the seed cartridge illustrated in FIG. 26;

FIG. 28 is a perspective view of a push rod for use with the seed cartridges illustrated in FIGS. 18 and 22;

FIGS. 29A–29G illustrate the sequence of events when loading a full seed cartridge into the fiberoptic-guided interstitial seed manual applicator in accordance with the present invention;

DETAILED DESCRIPTION

Figure 1:
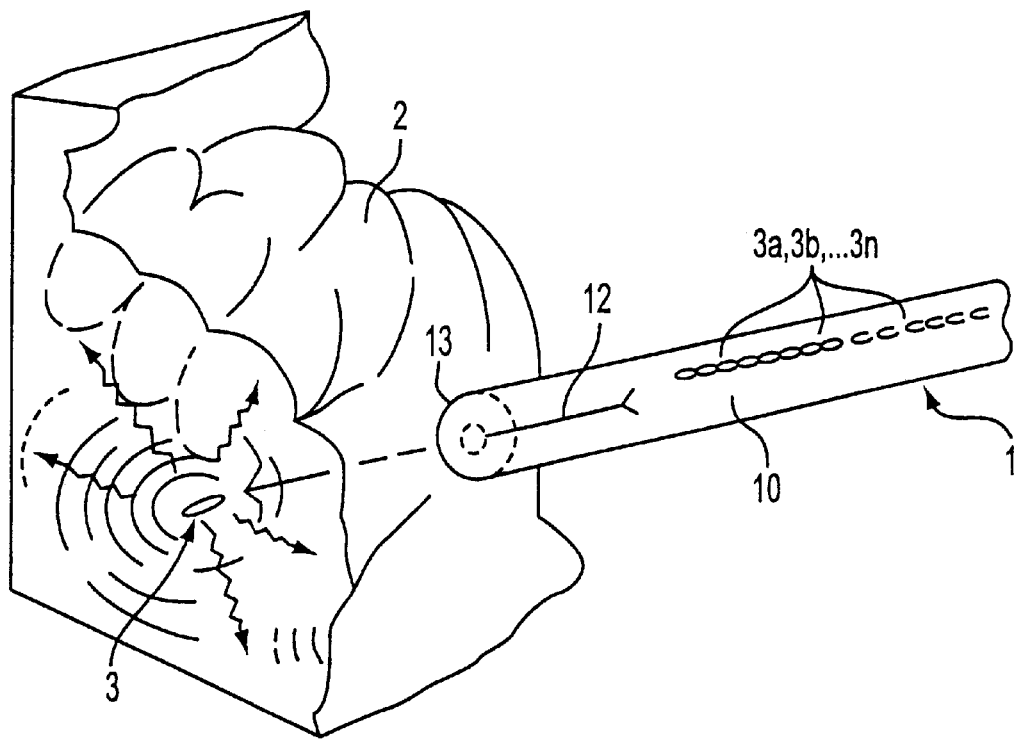
FIG. 1 is a perspective view illustrating implantation of interstitial seeds using the fiberoptic-guided interstitial seed manual applicator in accordance with the present invention.

Referring to the drawings, there is illustrated a fiberoptic-guided interstitial seed manual applicator ("FOGISMA") 1 in accordance with the present invention. FIG. 1 is illustrative of the general purpose of the FOGISMA device 1; e.g., to implant one or more seeds, 3, 3a, 3b, . . . 3n in or around a tumor or other target tissue 2 within a patient. It is understood that the present invention is not intended to be limited solely by brachytherapy procedures for implanting radioactive seeds, and may be utilized for performing other medical implantation procedures where small bodies or objects are implanted within or near target tissue of a patient (e.g., chemotherapy). As such, the term "seed" as used herein is intended to broadly mean an object or body to be implanted within a patient, including, but not limited to radioactive seeds used in brachytherapy procedures.

The FOGISMA device 1 illustrated in FIG. 1 comprises an outer sheath 10 and a hollow introducer needle 12 that is longitudinally displaceable relative the outer sheath 10 for implanting seeds 3, 3a, 3b, . . . 3n. The distal end 13 of the outer sheath 10 is illustrated as being in generally apposed or abutting relationship to the tumor 2. Numerous "unfired" seeds 3a, 3b, . . . 3n that have not yet been implanted or deposited within or near the tumor 2 are also illustrated in FIG. 1 as being in aligned end-to-end relation to each other within the FOGISMA device 1.

Figure 2:
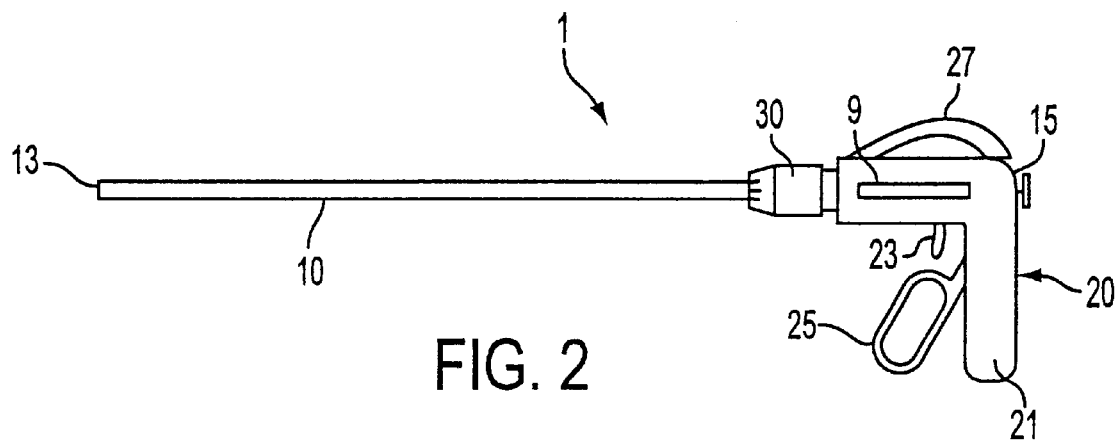
FIG. 2 is a side elevation view of the fiberoptic-guided interstitial seed manual applicator in accordance with the present invention.
Figure 3:
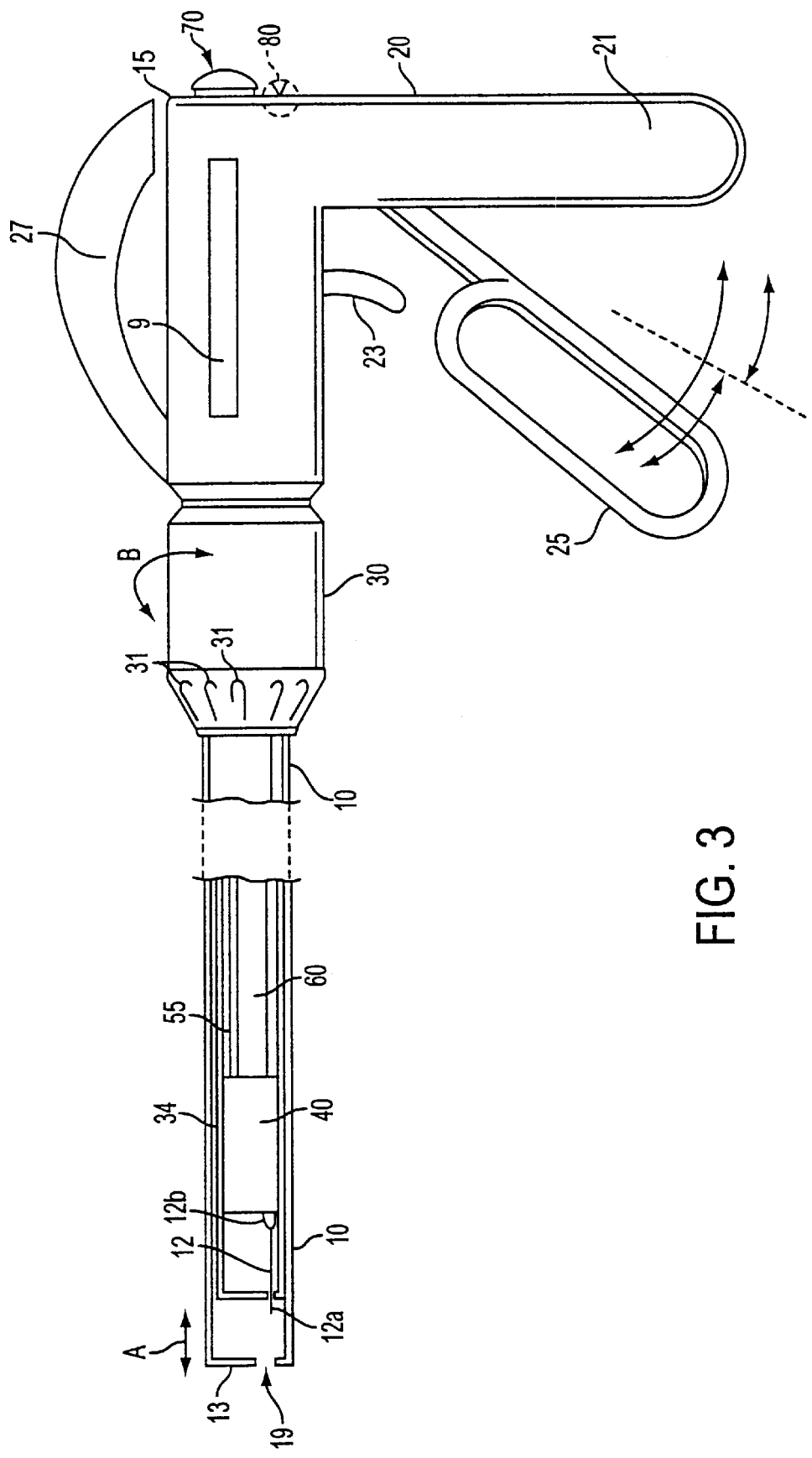
FIG. 3 is also a side elevation view further illustrating the fiberoptic-guided interstitial seed manual applicator shown in FIG. 2.

With specific reference to FIGS. 2 and 3, the FOGISMA device 1 includes a distal end 13 (which is also the distal end of the outer sheath 10) and a proximal (control) end 15. As used herein, the term "distal" is intended to generally refer to the relevant portion of the FOGISMA device 1 that is closet to the distal end 13 (and furthest away from the proximal end 15) of the device 1 and the term "proximal" is intended to generally refer to the relevant portion of the FOGISMA device 1 that is furthest away from the distal end 13 (and closest to the proximal end 15) of the device 1.

At the proximal end 15 of the FOGISMA device 1 is a housing 20 that facilitates handling and control of the device by the surgeon or other operator thereof. The housing 20 is preferably made of any suitable molded material (e.g., plastic or stainless steel) that is acceptable for such medical procedures and may be formed in two complimentary halves that may be fastened or otherwise joined together to facilitate construction of the FOGISMA device 1.

While the housing 20 may be formed in a variety of different configurations, it is preferred that the housing be of a generally L-shaped pistol configuration for convenient and ready control and operation of the FOGISMA device 1. The preferred housing 20 therefore includes a handle or grip portion 21 to be held by the surgeon or operator of the device 1. At least a portion of the handle may be lined or coated with a thin layer of radiation insulating material (e.g., lead) to prevent or minimize radiation exposure to the surgeon or operator of the device 1.

As will be discussed further below, one embodiment of the housing 20 comprises a seed advancement trigger 23 and an implantation lever 25 for controlling the operation of the FOGISMA device 1. The trigger 23 and lever 25 are each mounted proximate the handle portion 21 so that the surgeon or operator of the FOGISMA device 1 may actuate the trigger 23 and/or the lever 25 to control operation of the device 1 with the same hand that the surgeon or operator is using to hold the handle portion 21.

A supplemental handle 27 may also be integrally formed or separately mounted on the housing 20, which supplemental handle 27 may be used by the surgeon or operator of the FOGISMA device 1 to transport and/or further steady the FOGISMA device 1 during operation. In FIGS. 2 and 3, the supplemental handle 27 is illustrated as preferably being mounted on the top of the housing 20.

Figure 4:
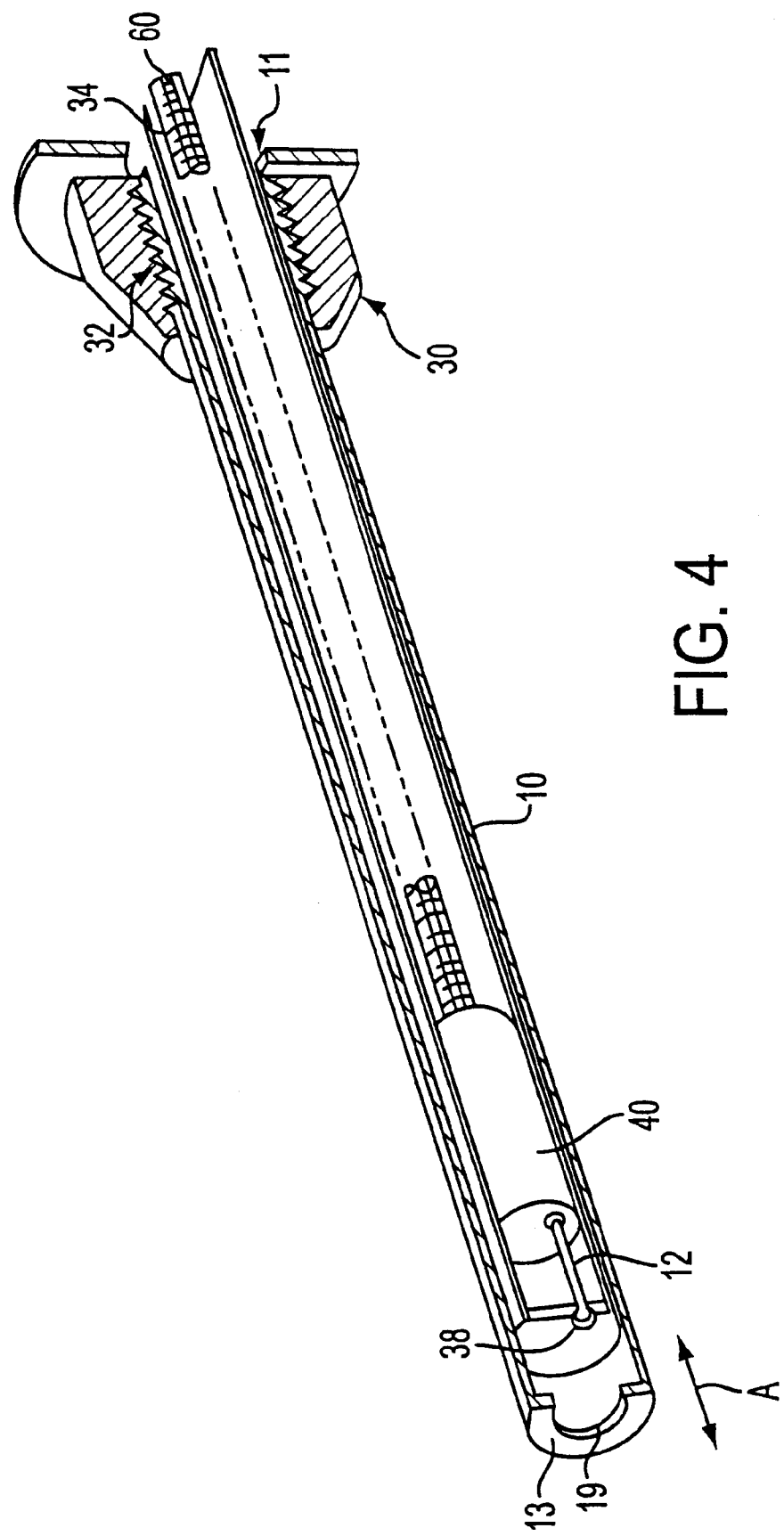
FIG. 4 is a longitudinal cross-sectional view of the roticulator ring and outer sheath of the fiberoptic-guided interstitial seed manual applicator illustrated in FIG. 3.

In one embodiment of the present invention, the outer sheath 10 of the FOGISMA device 1 is movably attached to the housing 20 using a roticulator ring 30 positioned between the outer sheath 10 and the housing 20. With reference to FIGS. 3 and 4, the roticulator ring 30 is rotatably mounted on a forward end of the housing 20 in a conventional manner. The roticulator ring 30 includes a bore therethrough of a diameter slightly greater than the outside diameter of the outer sheath 10 in order to permit the outer sheath to snugly pass therethrough during assembly of the FOGISMA device 1. Internal threads 32 are formed within the bore of the roticulator ring 30 for interlocking engagement with external circumferential threads 11 formed in at least a portion of the exterior circumferential surface of the outer sheath 10. Thus, rotation of the roticulator ring 30 (in the direction of arrow B in FIG. 3) causes the outer sheath 10 to move longitudinally (in the direction of arrow A) relative to the handle 20.

Accordingly, the surgeon or operator of the FOGISMA device 1 is able to precisely control or modulate the depth of the introducer needle 12 within the target tissue 2 by rotating the roticulator ring 30 either clockwise for shallower insertions of needle 12 or counterclockwise for deeper insertions of needle 12. Because the outer sheath 10 is intended to abut against the tumor, tissue wall, template or grid during operation of the device 1, it is the length of introducer needle 12 protruding beyond the outer sheath 10 when the insertion lever 25 is fully depressed that determines the relative needle length and thereby dictates the depth of insertion. Calibrated markings or indicia 31 on the roticulator ring 30 permit the surgeon or operator to precisely set the depth of the introducer needle 12 according to the desired specification. That is, the indicia 31 indicate the relationship between the distal end 12 of the outer sheath 10 and the distal tip 12a of the introducer needle 12.

Referring now to FIGS. 2, 3, 4 and 5, the outer sheath 10 extends from the handle 20 to the distal end 13 of the FOGISMA device 1. The outer sheath 10 is preferably a rigid, elongated, hollow, tubular member. Alternatively, the outer sheath 10 be a flexible or deflectable tubular member. The portion of the outer sheath 10 proximate the distal end 13 of the device 1 is substantially enclosed to protect or cover the components of the FOGISMA device 1 (including introducer needle 12) located within the outer sheath 10. An exit port 19 is formed in the end of the outer sheath 10 (proximate the distal end 13 of the device) in aligned relation to the introducer needle 12 to permit at least a portion of the needle 12 to pass therethrough during operation of the FOGISMA device 1 at the time of implantation of a seed 3.

A rigid, elongated, hollow, tubular inner sheath 34 may be located within the outer sheath 10 of the FOGISMA device 1. The length and outside diameter of the inner sheath 34 is less than the length and inside diameter of the outer sheath 10 to facilitate assembly of the inner sheath 34 within the outer sheath 10. Like the outer sheath 10, the distal end of the inner sheath 34 (proximate the distal end 13 of the device 1) is substantially enclosed to protect or cover the components of FOGISMA device 1 located within the inner sheath 34. An exit port 38 is formed in the distal end of the inner sheath 34 (proximate the distal end 13 of the device ) in aligned relation with the exit port 19 of the outer sheath 10 and the introduce needle 12 to permit at least a portion of the needle 12 to pass therethrough during set up and operation of the FOGISMA device 1. In the neutral or non-implantation position, it is preferred that the distal end 12a of the introducer needle 12 project just slightly through the exit port 38 formed in the inner sheath 34. Preferably, the inner and outer sheaths 34 and 10 are made from any suitable material that is capable of withstanding conventional medical instrument sterilization techniques (e.g., autoclave, radiation, x-ray, or ethylene oxide gas sterilization) and is acceptable for such medical procedures (e.g., plastic, stainless steel, etc.).

Figure 5:
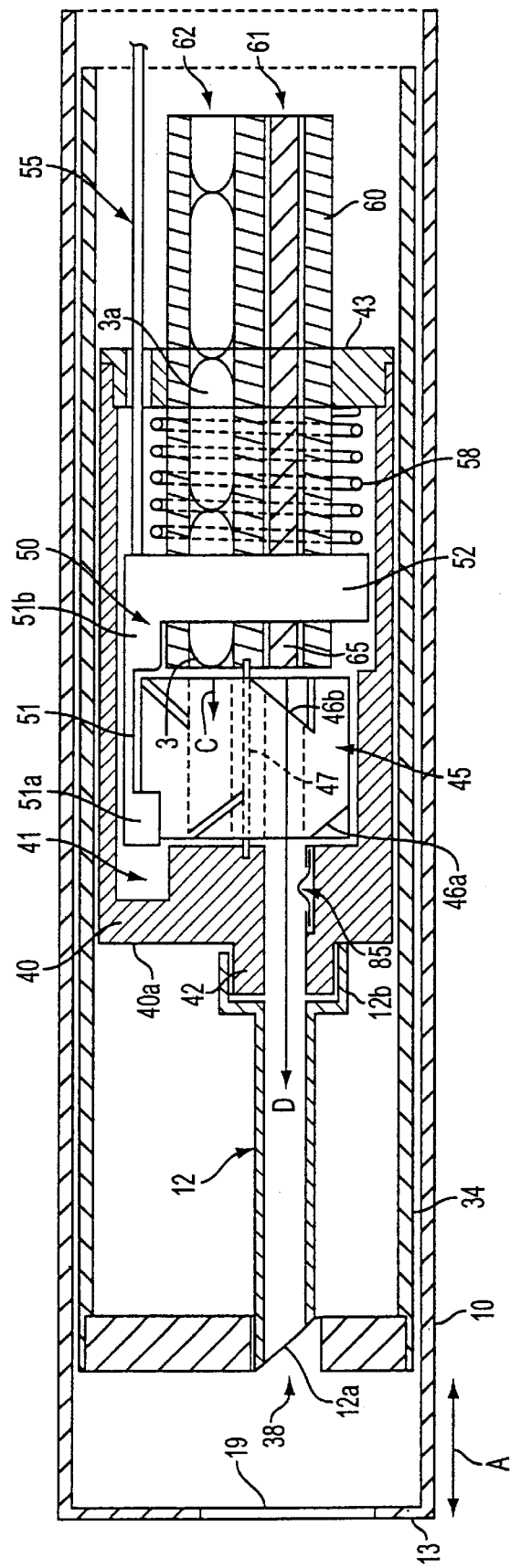
FIG. 5 is an enlarged longitudinal cross-sectional view of the distal portion of the fiberoptic-guided interstitial seed manual applicator illustrated in FIG. 3.
Figure 6:
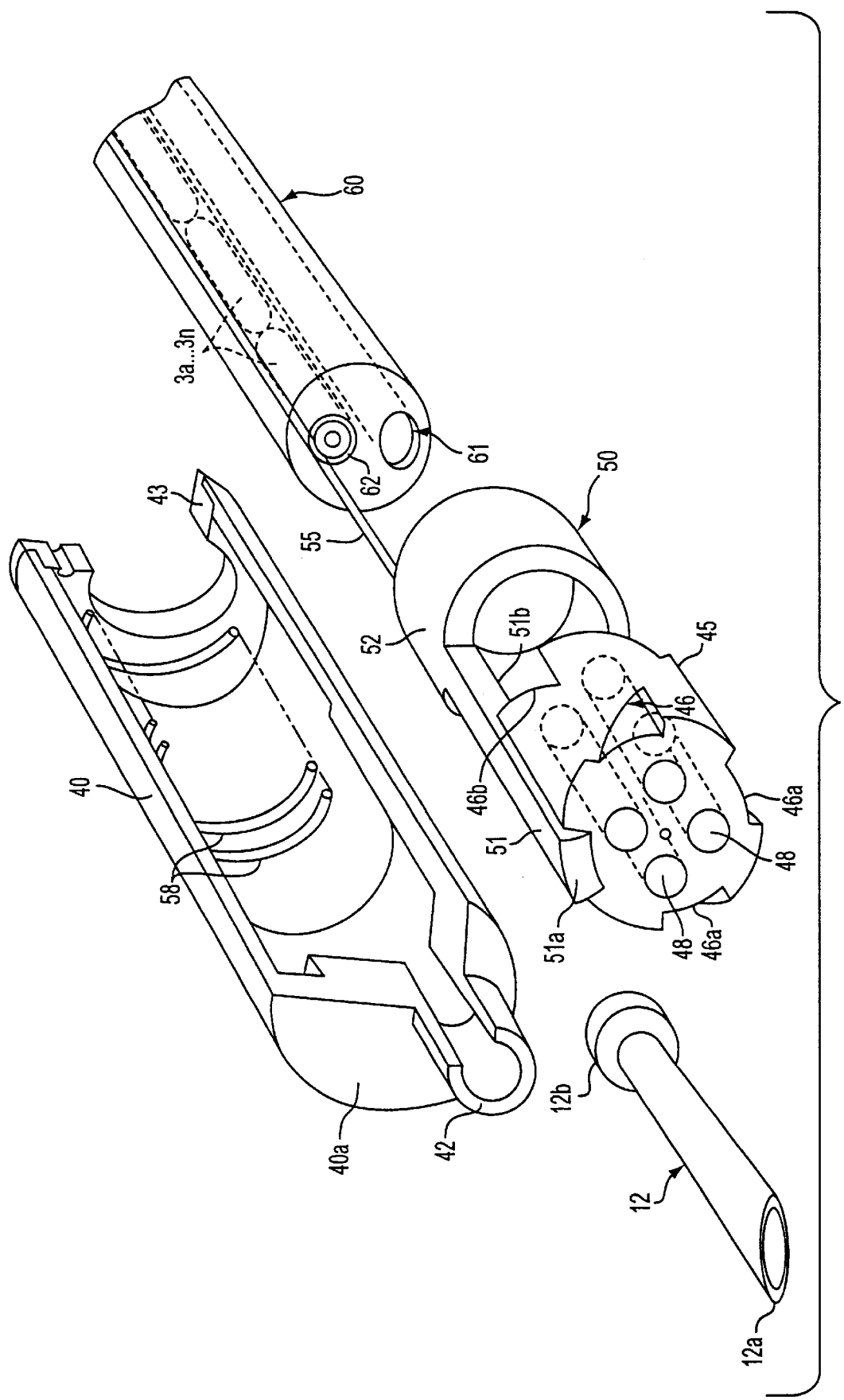
FIG. 6 is an exploded view of the seed transfer barrel mechanism illustrated in FIG. 5.
Figure 7:
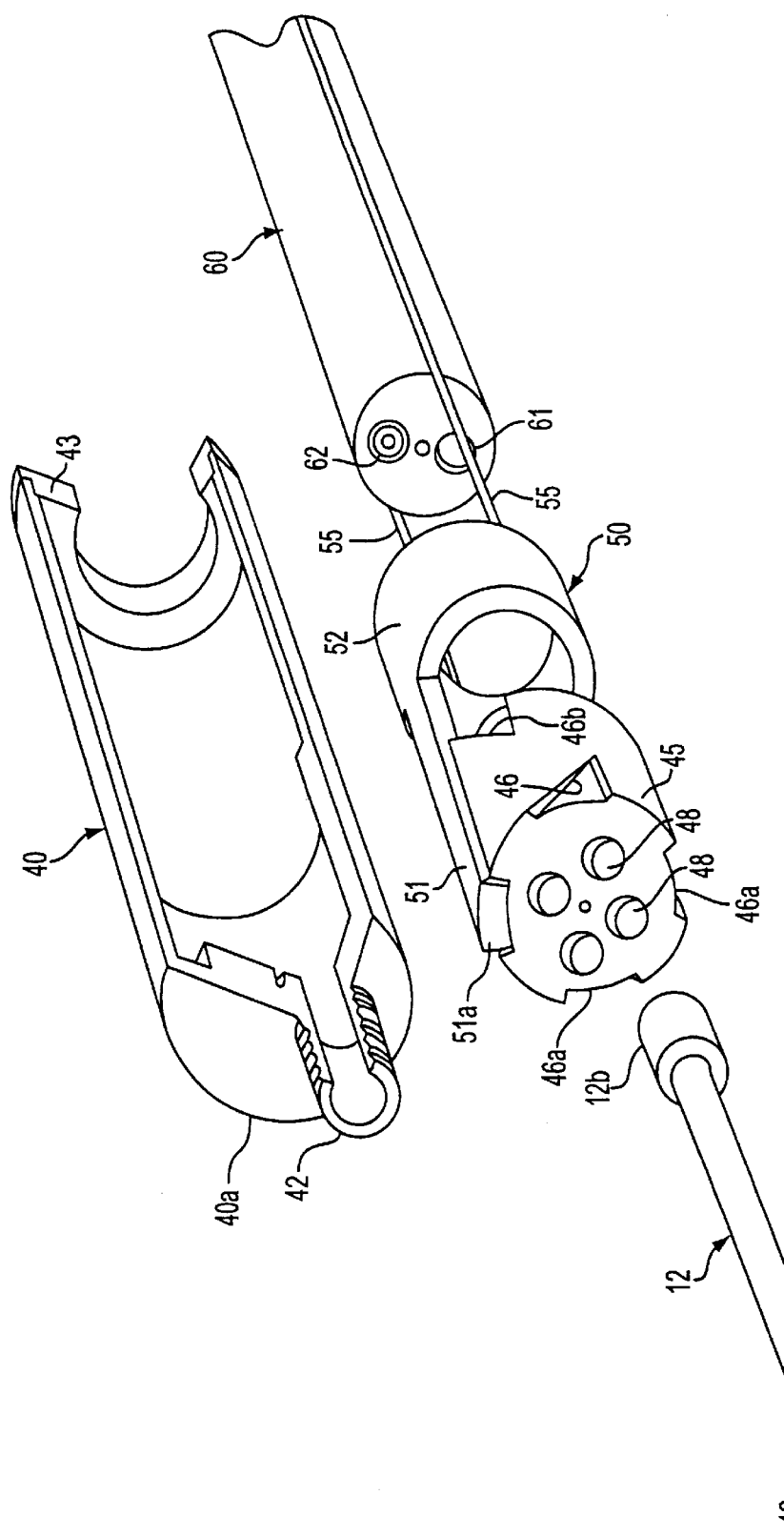
FIG. 7 is also an exploded view of the seed transfer barrel mechanism illustrated in FIG. 5.

Referring to FIGS. 5, 6 and 7, the introducer needle 12 and a seed transfer barrel housing 40 are located within the inner and outer sheaths 10 and 34. The introducer needle 12 is hollow throughout its entire length to allow seeds 3, 3a, ... 3n to pass therethrough. Accordingly, the diameter of the bore or hollow through the needle 12 is generally slightly larger than that of the seeds, 3, a , ... 3n. The introducer needle 12 preferably includes a flanged proximal end 12b and a tapered or sharpened point at its distal end 12a to facilitate injection into body tissue.

The flanged proximal end 12b of the needle 12 is preferably formed having internal threads for convenient attachment (e.g., threaded engagement) to mating threads formed on the circumference of the threaded flange 42 of the seed transfer barrel housing 40, as will be discussed further below. Alternatively, the needle 12 may be attached to the seed transfer barrel housing 40 using a conventional Luer-Lok connection.

As is best illustrated in FIGS. 5, 6 and 7, the seed transfer barrel housing 40 is shown mounted within the inner and outer sheaths 10 and 34. The seed transfer barrel housing 40 is generally cylindrical in shape having a smaller outside diameter than the inside diameter of the inner sheath 34. Projecting from one end 40a of the barrel housing 40 is the threaded flange 42 for securing the introducer needle 12 to the barrel housing 40. As discussed above, the threaded flange 42 may contain male threads or other means (e.g., Leur-Lok connection) for engagement with female threads formed on the proximal end 12b of the introducer needle 12. It is understood, however, that the proximal end 12b of the introducer needle 12 could alternatively be formed with male threads that screw into and engage threads formed within a female portion (e.g., aperture) of the barrel housing 40.

Preferably, a plurality of different interchangeable introducer needles 12 should be available to the surgeon or operator of the FOGISMA device 1. These needles 12 may, for instance, range from 1–20 cm in length and from 0.2–15 mm in diameter. Depending upon the particular application, therefore, the surgeon or operator of the device 1 may select the appropriate sized introducer needle 12 from the available selection of interchangeable needles and conveniently attach the selected needle 12 to the threaded flange 42 of the seed transfer barrel housing 40.

The opposing or proximal end of the barrel housing 40 (opposite end 40a) is preferably open so that the barrel housing 40 has a longitudinally extending bore running substantially therethrough to the end 40a. In addition, a longitudinally extending aperture is formed through flange 42 and end 40a of the barrel housing 40, which aperture is in aligned relation with the bore or hollow through the introducer needle 12 when the needle is secure to the flange 42. The diameter of the aperture extending through flange 42 and end 40a is generally slightly larger than that of the seeds, 3, 3a, . . . 3n to facilitate transfer of the seeds through the aperture in the direction of arrow D in FIG. 5.

A cylindrically-shaped cover 43 having an opening formed therein is secured in a conventional manner to the open end of barrel housing 40. The opening in cover 43 is of such size as to permit introduction of elongated, longitudinally extending member 60 through the opening and partially into the bore of barrel housing 40. The elongated member 60 is preferably a rigid, generally cylindrical member (e.g., injection molded plastic) having one end located within the bore of barrel housing 40 and an opposing end proximate the proximal end 15 of the FOGISMA device 1. The elongated member may be lined or coated with a thin layer of radiation insulating material (e.g., lead) to prevent or minimize radiation exposure to the surgeon or operator during operation of the device 1.

Extending through the elongated member 60 are two parallel longitudinally extending channels, a fiberoptic channel 61 and a seed alignment channel 62. Fiberoptic channel 61 is aligned with the bore or hollow through the introducer needle 12 and the aperture through the flange 42. A plunger 65, which preferably contains a fiberoptic scope or other optical means, is positioned within the fiberoptic channel 61 and is movable within the channel 61 in response to movement of the lever 25. A fiberoptic port 80 is provided in the proximal end 15 of the FOGISMA device 1 to facilitate connection of a fiberoptic scope or other optical means (not shown) to the plunger 65, as is illustrated in FIG. 3.

In one preferred embodiment, a plunger 65 containing a fiberoptic scope is utilized to provide visual assistance to the surgeon for implant guidance and to transfer the seed 3 from the multi-chamber transfer barrel 45 through the introducer needle 12 and into the tumor 2. It is understood, however, that other conventional optical means may be substituted for the fiberoptic scope, such as a rod lens scope, Hopkins type scope, laparoscope, endoscope, etc. The fiberoptic scope or other optical means may be inserted through a longitudinal bore through the plunger 65 for providing such visual assistance.

The seed alignment channel 62 formed within the elongated member 60 is generally slightly larger than the diameter of the seeds 3, 3a, . . . 3n to facilitate transfer of the seeds in end-to-end aligned relation through the seed alignment channel 62 in the direction of arrow C in FIG. 5.

A seed transfer barrel 45 is positioned within the bore of the barrel housing 40 and is rotatable relative the housing 40. Preferably, the seed transfer barrel 45 is generally cylindrical in shape with a centrally positioned, longitudinally extending opening therethrough. A mounting pin 47 supported on one end by the end 40a of the barrel housing 40 and on the opposing end by the elongated member 60 is received within the opening in the barrel 45 in order to rotatably support the barrel.

Figure 8:
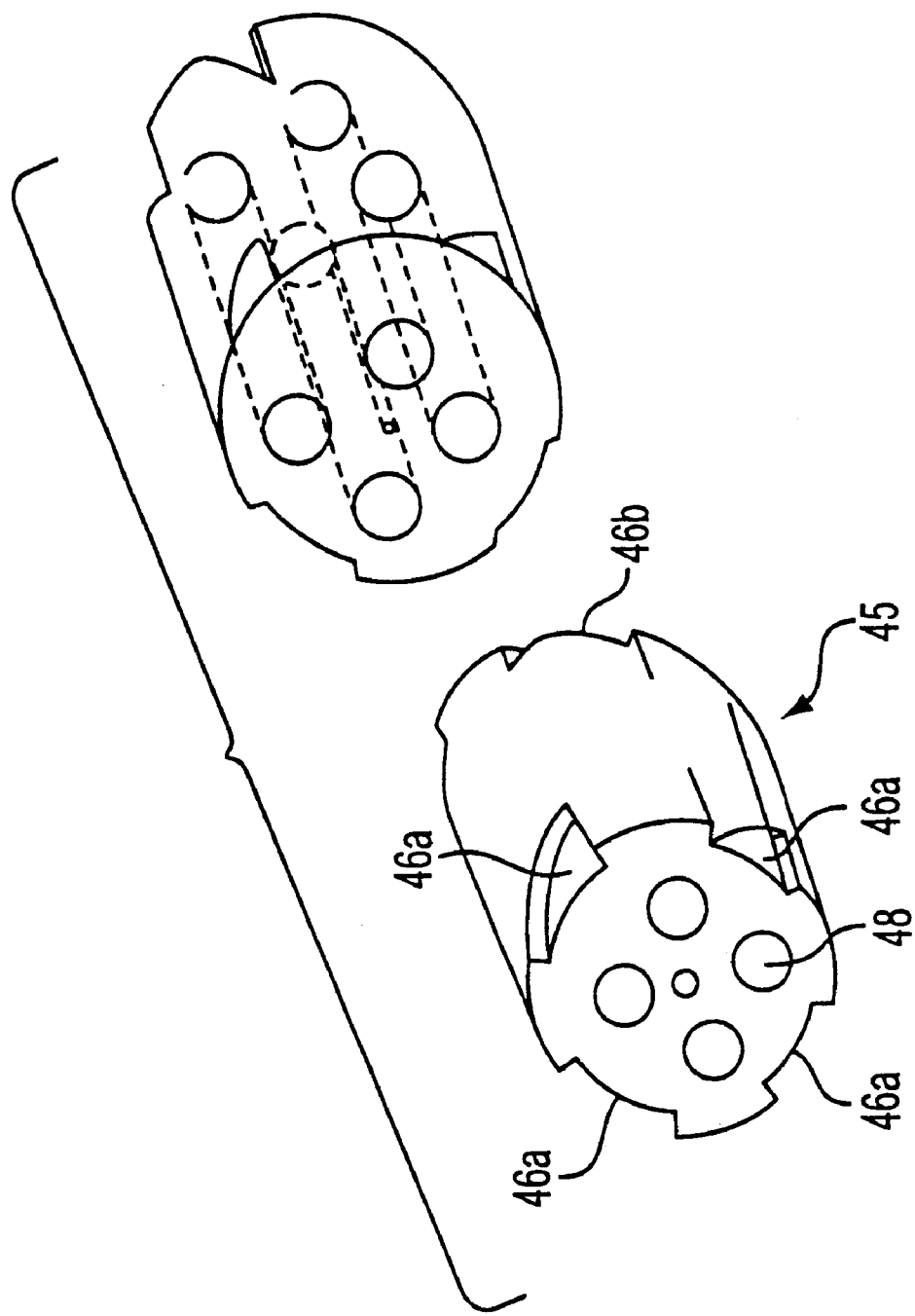
FIG. 8 is a perspective view of the multichamber seed transfer barrel illustrated in FIG. 5.
Figure 9:
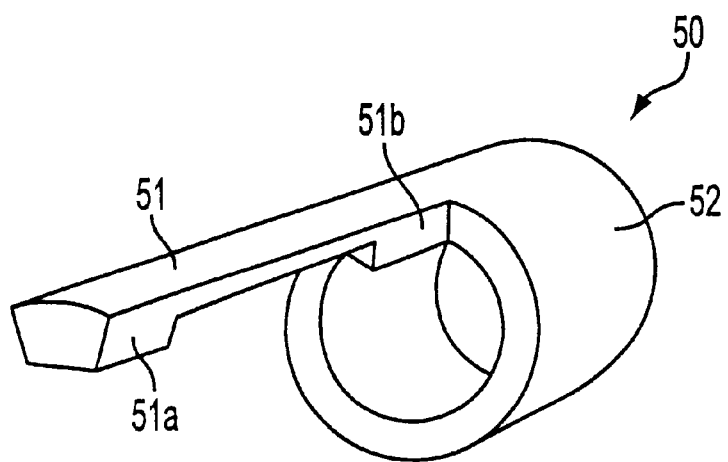
FIG. 9 is a perspective view of the advancing pin and ring mechanism illustrated in FIG. 5.
Figure 10:
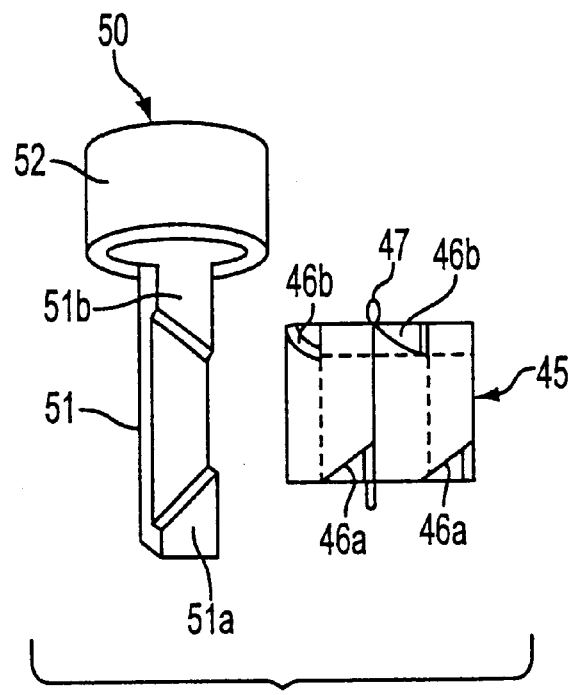
FIG. 10 is an exploded view of the advancing pin and ring mechanism and seed transfer barrel mechanism illustrated in FIG. 5.
Figure 11:
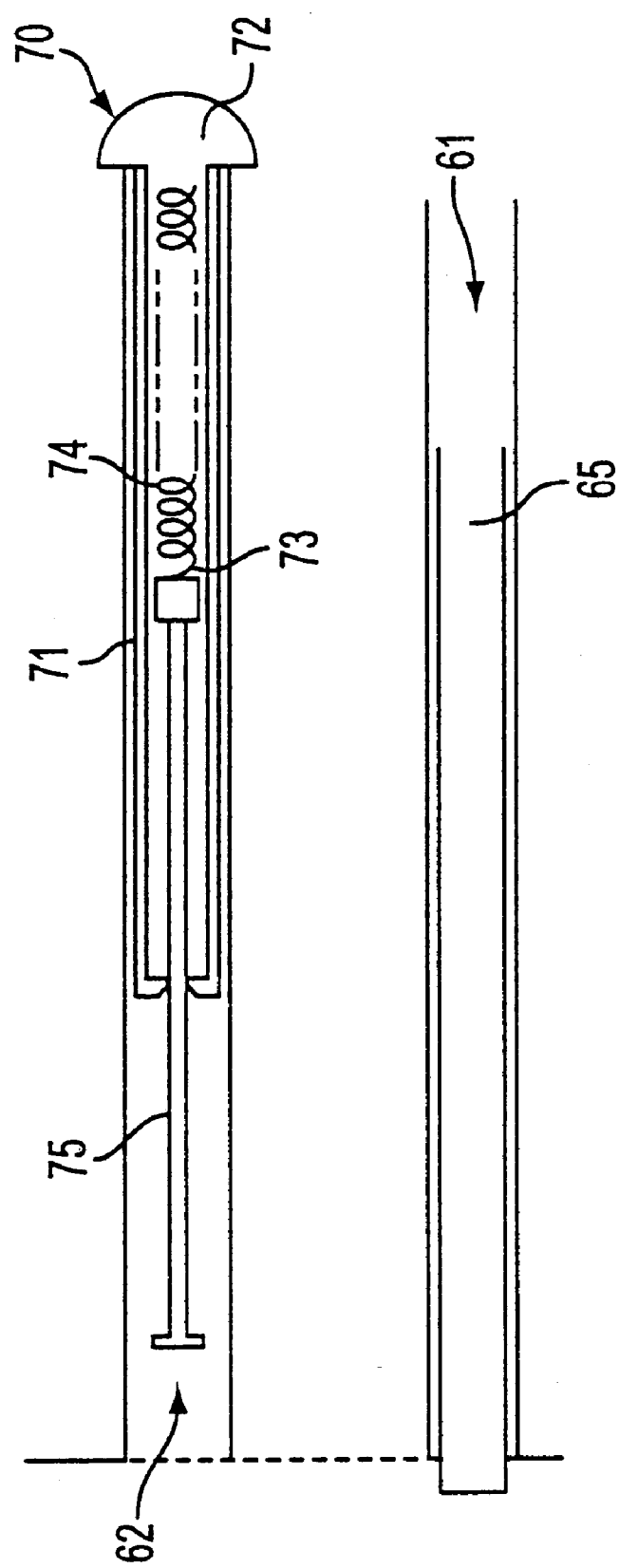
FIG. 11 is a longitudinal cross-sectional view of the seed biasing mechanism and fiberoptic plunger of the fiberoptic-guided interstitial seed manual applicator illustrated in FIG. 3.

The seed transfer barrel 45 also comprises a plurality of parallel, equally spaced apart seed chambers 48, each of which extends longitudinally through the barrel 45. In the embodiment illustrated in FIGS. 6, 7 and 8, four seed chambers 48 are shown, each of which is equally spaced apart at 90° from the preceding and subsequent chambers 48. The length and diameter of each chamber 48 is such as to permit only one seed 3 to enter a given chamber 48 at one time. It is understood, however, that a greater or lesser number of seed chambers 48 may be utilized in accordance with the invention. For instance, the seed transfer barrel 45 could be provided with only two seed chambers 48 spaced apart from one another by 180°.

The barrel housing 40, cover 43, seed transfer barrel 45, advancing pin and ring mechanism 50, and elongated member 60 are preferably made in a conventional manner (e.g., injection molded) from any suitable material that is capable of withstanding conventional medical sterilization techniques( e.g., autoclave, radiation, x-ray, or ethylene oxide gas sterilization), is acceptable for such medical procedures (e.g., plastic, stainless steel, etc.) and may be manufactured to suitable tolerances. These components and/or other outer or inner sheaths 10, 34 may be lined or coated with a thin layer of radiation insulating material (e.g., lead) to prevent or minimize radiation exposure to the surgeon or operator of the device 1.

As illustrated in FIGS. 3, 5, 11 and 12A–12C, a seed biasing member 70 removably mounted on the housing 20 biases the seeds 3, 3a, . . . 3n within the seed alignment channel 62 toward the seed transfer barrel 45. The seed biasing member 70 preferably comprises an elongate hollow body 71 that is closed on one end by a locking cap 72. A piston 73 is slidingly received within the hollow body 71. The piston 73 includes a piston rod 75 that projects longitudinally through an opening in the distal end of the hollow body 71. A biasing member 74, such as a compression spring, is positioned within the hollow body 71 and biases the piston 73 away from the locking cap 72.

The elongated body 71 of the seed biasing member 70 is received within a seed insertion port 81 extending through the housing 20 in alignment with the seed alignment channel 62 of the elongated member 60. The locking cap 72 is removably secured to the proximal end 15 of housing 20 in a conventional manner, such as via a tongue-in-grove arrangement. When installed on the FOGISMA device 1, the distal end of the piston rod 75 engages the last seed 3n within the seed alignment channel 62. Because the biasing member 74 biases the piston 73 and rod 75 toward the distal end 13 of the FOGISMA device 1, the seeds 3, 3a, . . . 3n are similarly biased within the seed alignment channel 62 in the direction of arrow C in FIG. 5, thereby advancing the first seed 3 into the seed chamber 48 within the transfer barrel 45.

Because each seed chamber 48 can only accommodate one seed 3, the second seed 3a within the seed alignment channel 62 may only advance after the seed transfer barrel 45 rotates so that an empty seed chamber 48 becomes aligned with the alignment chamber 62.

On the circumference of the seed transfer barrel 45 are formed a plurality of equally spaced cut-out sections or cam portions 46, as is illustrated in FIGS. 5, 6, 7, 8, 10 and 12A–12C. As will be explained further below, these cam portions 46 are used to selectively rotate or drive the transfer barrel 45 relative the barrel housing 40 in order to feed one seed 3 at a time into the introducer needle 12.

The transfer barrel 12 is driven in response to longitudinal movement of a substantially rigid barrel advancing pin and ring assembly 50 positioned within the bore of the barrel housing 40. With reference to FIGS. 5, 6, 7, 9, 10 and 12A–12C, the advancing pin and ring assembly 50 preferably comprises a generally cylindrical-shaped ring portion 52 and a longitudinally extending advancing pin or member 51. An aperture is formed through the ring portion 52 for slidably receiving the distal end of the elongated member 60. The outside diameter of the ring portion 52 is preferably slightly smaller than the inside diameter of the bore within the barrel housing 40 to facilitate sliding movement of the advancing pin and ring assembly 50 in the direction of arrow A relative the barrel housing 40 and transfer barrel 45.

The barrel advancing pin and ring assembly 50 is biased toward the transfer barrel 45 in the direction of arrow D in FIG. 5 by a spring member 58 (e.g., a compression spring). The spring member 58 is preferably positioned within the bore of the barrel housing 40 between the cover 43 and the ring portion 52. The outside diameter of the spring member 58 is smaller than the inside diameter of the bore in the barrel housing 40 to facilitate insertion of the spring member 58 into the housing 40. Similarly, the inside diameter of the spring member 58 is larger than the outside diameter of elongated member 60 to permit the member 60 to be inserted through the inside diameter of spring member 58.

A linking shaft 55 is also located within the inner and outer sheaths 10 and 34 and, in one embodiment, extends longitudinally therein between the ring portion 52 of the barrel advancing pin and ring assembly 50 and a seed advancement trigger 23 located in a housing 20 at the proximal end 15 of the FOGISMA device 1, which will be described further below. The distal end of the linking shaft 55 is connected in a conventional manner to the ring portion 52 in order to control the longitudinal movement of the barrel advancing pin and ring assembly 50 within the barrel housing 40 relative the seed transfer barrel 45. As further illustrated in FIG. 7, two linking shafts 55 operatively connected to the seed advancement trigger 23 may be utilized to control the longitudinal movement of the advancing pin and ring assembly 50. Referring to FIG. 5, for each linking shaft 55, an aperture may be formed within the cover 43 enclosing the barrel housing 40 to permit the linking shaft 55 to freely move through the cover 43.

The advancing pin 51 of the barrel advancing pin and ring assembly 50 projects longitudinally from the ring portion 52 in the direction of arrow D in FIG. 5. A first barrel advancing tooth 51a is formed on the projects downwardly from the advancing pin 51 proximate the distal end of the pin. A second barrel advancing tooth 51b is formed on and projects downwardly from the advancing pin 51 proximate the ring portion 52.

The first and second barrel advancing teeth 51a and 51b are configured to interlock with and engage cam portions 46a and 46b, respectively, on the transfer 45. In the preferred embodiment, the transfer barrel 45 is provided with a total of eight equally spaced cam portions 46. Four identical proximal cam portions 46b are circumferentially coated proximate the proximal end of the transfer barrel 45 and four identical distal cam portions 46a are circumferentially located proximate the distal end of the transfer barrel 45. In this preferred arrangement, the distal cam portions 46a are equally spaced along the circumference of the transfer barrel 45 at 90° intervals and the proximal cam portions 46b are similarly equally spaced along the circumference of the transfer barrel 45 at 90° intervals, but are shifted 45° along the circumference of the transfer barrel 45 from the distal cam portions 46a.

Figure 12A:
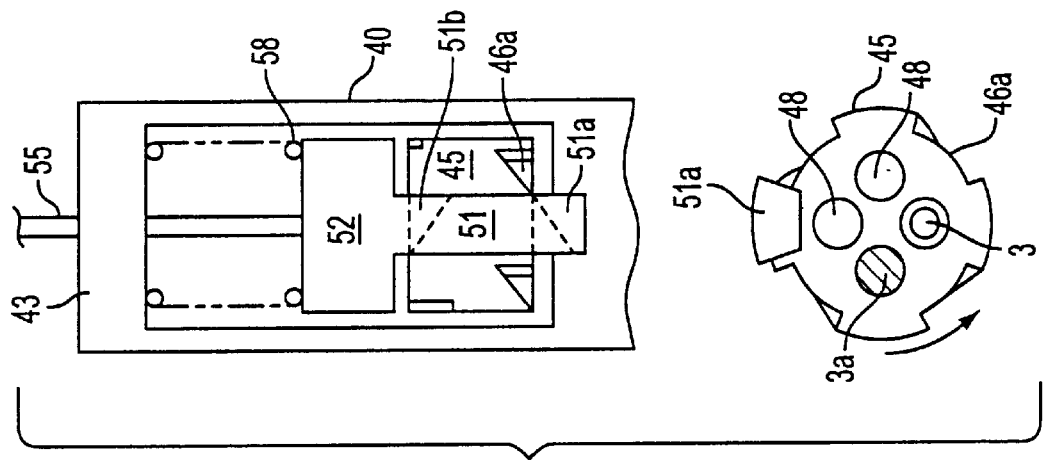
FIGS. 12A–12C are longitudinal cross-sectional views illustrating the operation of the multichamber seed transfer barrel and advancing pin and ring mechanism in accordance with the present invention.

A relieved portion 41 is formed in the end 40a of the seed transfer barrel housing 40 proximate the first barrel advancing tooth 51a of the advancing pin 51. As illustrated in FIG. 12A, because the advancing pin and ring assembly 50 is biased by spring member 58 toward the end 40a of the barrel housing 40, the first barrel advancing tooth 51a is received within the relieved portion 41 and is disengaged from the distal cam portion 46a of the transfer barrel 45, while the second barrel advancing tooth 51b is in interlocking engagement with the proximal cam portion 46b of the transfer barrel 45. In this portion, a seed is located within alignment chamber 62 is biased by the seed biasing member 70 into the empty seed chamber 48 of the transfer barrel 45 that is aligned with the chamber 62. A seed 3 is also illustrated in FIG. 12A as being located within the adjacent seed chamber 48.

Figure 12B:
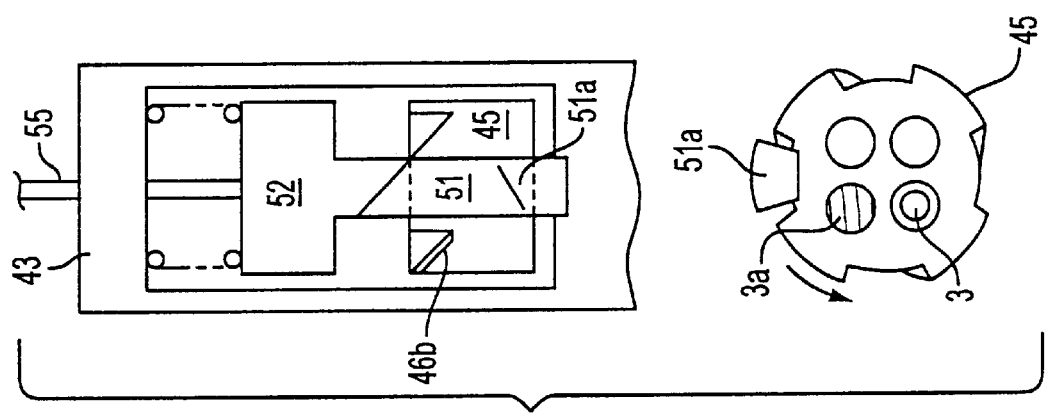

When the seed advancement trigger 23 is depressed by the surgeon or operator of the FOGISMA device 1, the movement of the trigger 23 overcomes the biasing force of the spring member 58 and causes the linking shaft 55 to move longitudinally within the inner sheath 34 toward the proximal end 15 of the device 1. As is illustrated in FIG. 12B, such longitudinal movement of the linking shaft 55 causes the barrel advancing pin and ring assembly 50 to move longitudinally within the barrel housing 40 in a direction toward proximal end 15. At the end of the trigger stroke, the first barrel advancing tooth 51a moves out of the relived portion 41 and engages a distal cam portion 46a of the transfer barrel 45, while the second barrel advancing tooth 51b disengages from the proximal cam portion 46b of the transfer barrel 45. Engagement of the first barrel advancing tooth 51a with one of the distal cam portions 46a causes the seed transfer barrel (and seed 3a) to rotate a predetermined amount. In the preferred embodiment having a total of eight equally spaced cam portions 46, this rotation of the multi-chamber transfer barrel 45 is precisely one eighth of a revolution. Thus, seeds 3 and 3a are illustrated in FIG. 12B as having rotated with transfer barrel 45 precisely 45° in the counterclockwise direction.

Figure 12C:
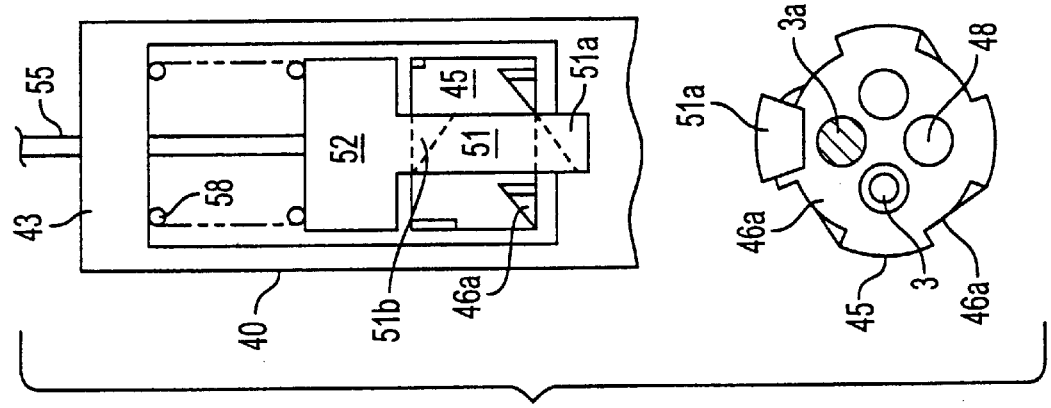

Referring to FIG. 12C, upon release of the trigger 23 by the surgeon or operator, the spring member 58 biases the advancing pin and ring mechanism 50 back to its original position with the first barrel advancing tooth 51a again received within the relieved portion 41 and disengaged from the distal cam portion 46a of the transfer barrel 45, while the second barrel advancing tooth 51b engages with one of the proximal cam portions 46b of the transfer barrel 45. Engagement of the second barrel advancing tooth 51b with one of the proximal cam portions 46b causes the seed transfer barrel 45 to further rotate a predetermined amount. In the preferred embodiment having a total of eight equally spaced cam portions 46, this further rotation of the multichamber transfer barrel 45 is precisely one eighth of a revolution (or a total of one quarter a revolution from depression of the trigger 23 to release thereof). In this position, the next or subsequent seed 3b (not shown) with alignment chamber 62 that was adjacent to ejected seed 3a is biased by the seed biasing member 70 into the empty seed chamber 48 of the transfer barrel 45 that is aligned with the chamber 62. In addition, seeds 3 and 3a have rotated with transfer barrel 45 another 45° in the counterclockwise direction.

In the preferred embodiments described and illustrated herein, the FOGISMA device 1 is ready for firing when the seed chamber 48 (containing a single seed 3) of the multi-chamber seed transfer barrel 45 rotates 180° from the point where seed 3 was initially biased into the chamber 48 (i.e., when chamber 48 was aligned with seed alignment channel 62) to a position where chamber 48 containing that seed 3 is aligned with fiberoptic channel 61 and the bore through introducer needle 12.

To prevent seed 3 in this firing position from prematurely discharging from chamber 48 (e.g., should the needle 12 be pointed in a downward direction such that the force of gravity may cause seed 3 to prematurely discharge from chamber 48 and continue through needle 12), a reducible seed lock 85 is preferably provided in the longitudinal opening of the threaded flange 42 of the barrel housing 40, as illustrated in FIGS. 5 and 13. The reducible seed lock 85 preferably comprises a spring member 86. Spring member 86 may be a flat, elongated metal or plastic spring having a distal end 86a and a proximal end 86b. A portion 87 of the threaded flange 42 is relieved within the longitudinal opening passing through the threaded flange 42 for receiving the distal and proximal ends 86a and 86b of the spring member 86. The relieved portion 87 is sufficiently large to permit the ends 86a and 86b to expand longitudinally when spring member 86 is compressed.

When the distal and proximal ends 86a and 86b of the spring member 86 are inserted within relieved portion 87, a portion 86c of spring member 86 projects into the longitudinal opening in threaded flange 42. Because spring portion 86c projects into the opening, spring portion 86c prevents a seed 3 prematurely discharging from chamber 48 from passing through the flange 42 into needle 12. Only when a longitudinal force is provided to seed 3 sufficient to overcome (compress) spring 86 within relieved portion 87 (e.g., when fiberoptic plunger 65 is advanced down the fiberoptic channel 61, through the aligned seed channel 48 of the transfer barrel 40 and into the aligned opening of flange 42) will seed 3 be able to advance beyond the seed lock 85 and into the needle 12.

Figure 14:
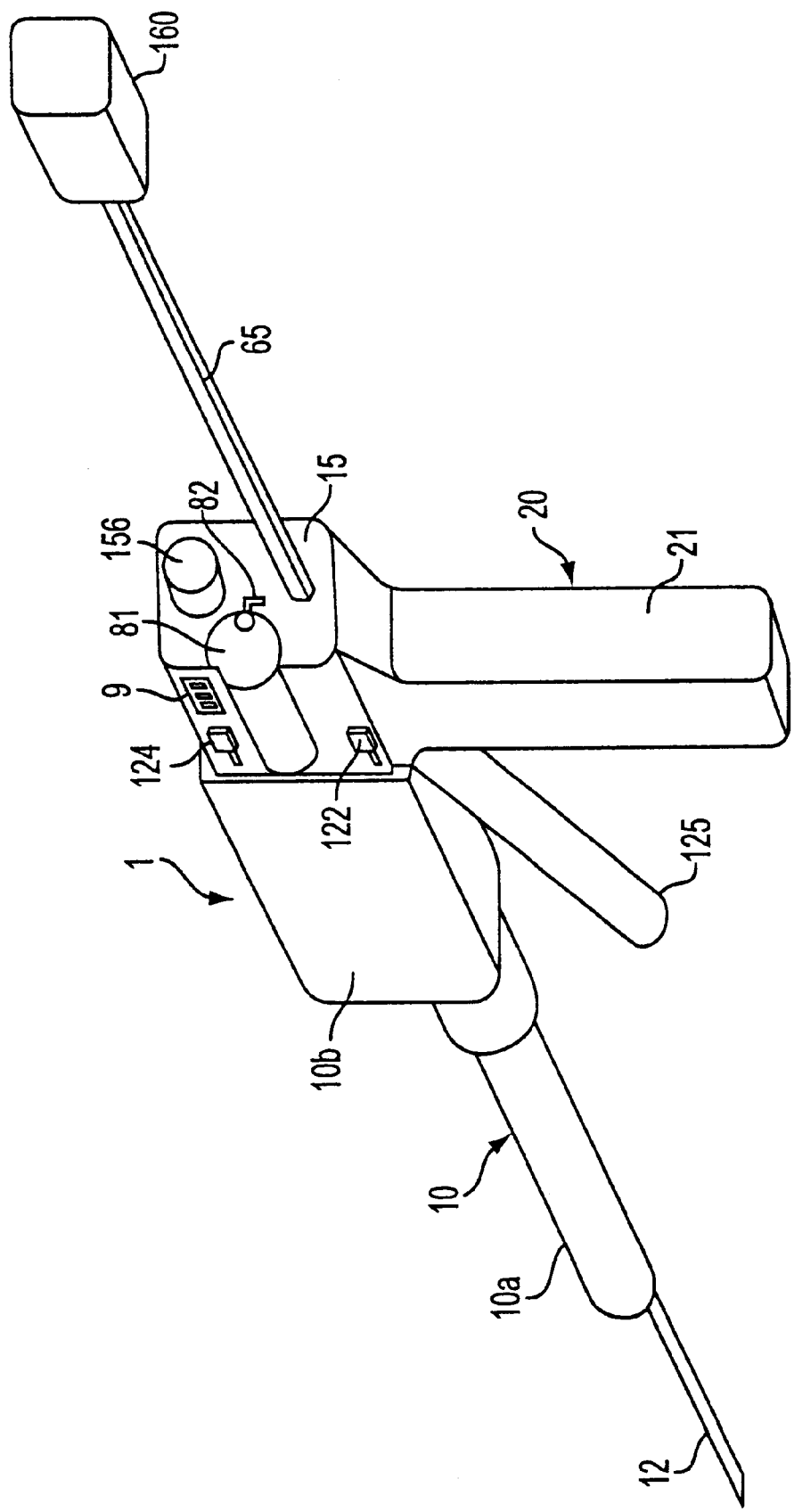
FIG. 14 is a perspective view of a second embodiment of the fiberoptic-guided interstitial seed manual applicator in accordance with the present invention.
Figure 15:
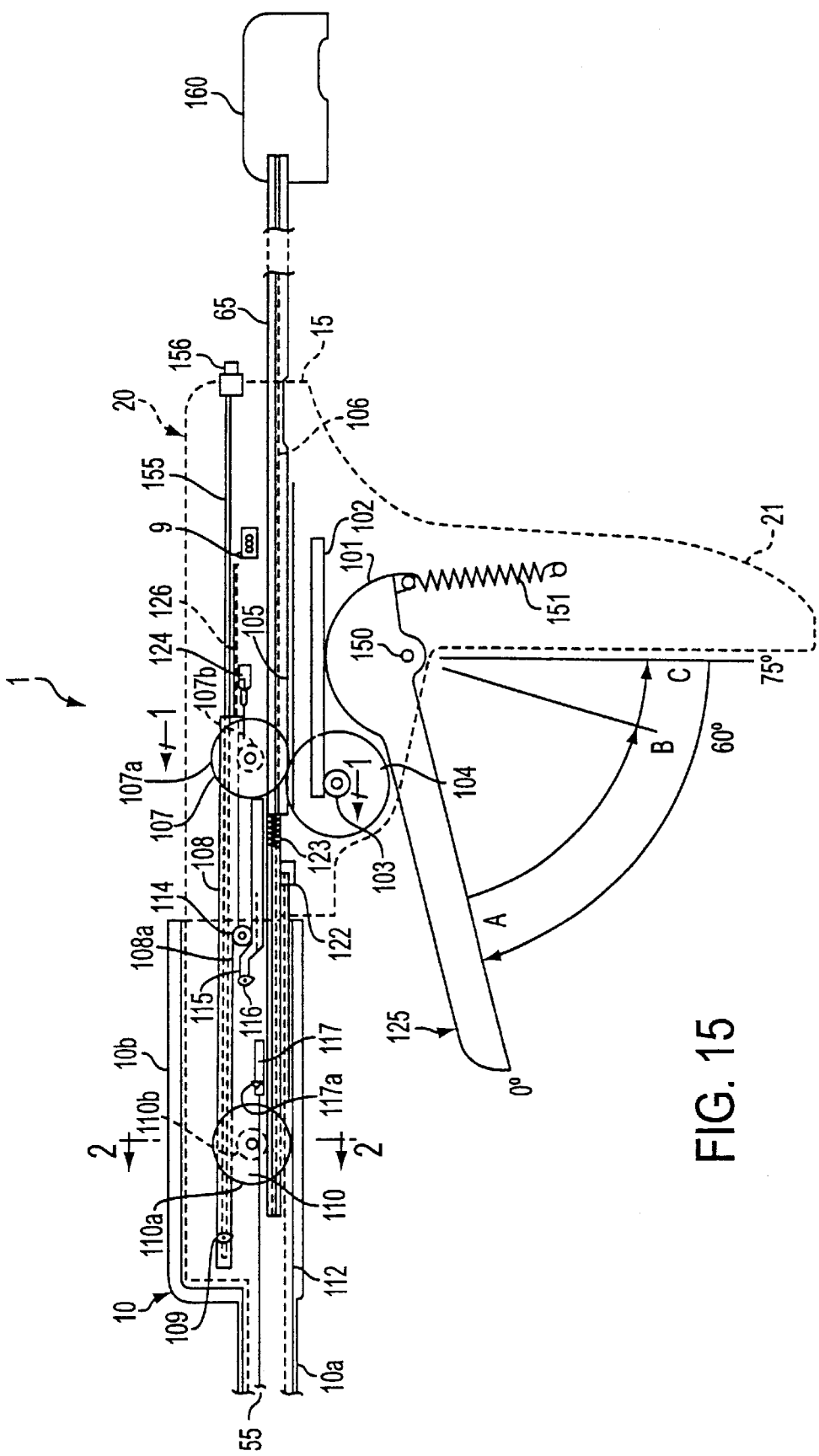
FIG. 15 is a side elevational view of the fiberoptic-guided interstitial seed manual applicator illustrated in FIG. 14.

A second embodiment of the FOGISMA device 1 is illustrated in FIGS. 14–17. Referring to FIG. 15, a cross-section of a housing 20 and the proximal portion of the outer sheath 10 of the FOGISMA device 1 are illustrated. Like the first embodiment described above, the housing 20 of the second embodiment is preferably L-shaped and may be injection molded from a suitable plastic that is capable of maintaining accurate dimensional stability during and after repeated use and sterilizations. The housing 20 may be formed in two complimentary halves that may be fastened or otherwise joined together to facilitate construction of the FOGISMA device 1.

The outer sheath 10 of this second embodiment is similar to that described above with respect to the first embodiment. Although only partially illustrated in FIG. 15, a distal portion 10a of outer sheath 10 includes a first bore extending longitudinally through the distal end 13 of the device 1 in a similar manner to the outer sheath of the first embodiment.

A proximal portion 10b of the outer sheath 10 having a second bore is connected to the distal portion 10a. The second bore of outer sheath portion 10b is preferably larger than the first bore of outer sheath portion 10a so that the proximal portion 10b may slidingly receive at least the distal end of the housing 20.

A control lever 125 is pivotally mounted proximate the handle portion 21 so that the surgeon or operator of the FOGISMA device 1 may actuate the lever 125 to control operation of the device 1 with the same hand that the surgeon or operator is using to hold the handle portion 21. Control lever 125 is pivotally mounted to housing 20 by pin 150. The control lever 125 comprises an arcuate, first pinion section 101 within housing 20 having a plurality of gear teeth formed thereon. A spring 151 having one end affixed to handle portion 21 and the opposing end affixed to the control lever 125 biases the control lever about pin 150 to a neutral position A, as illustrated in FIG. 15.

Figure 16:
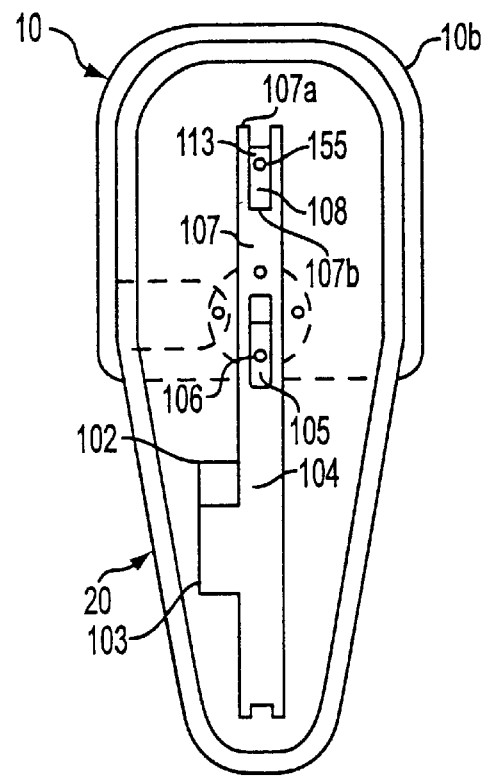
FIG. 16 is a cross sectional view taken along line 1—1 shown in FIG. 15.
Figure 17:
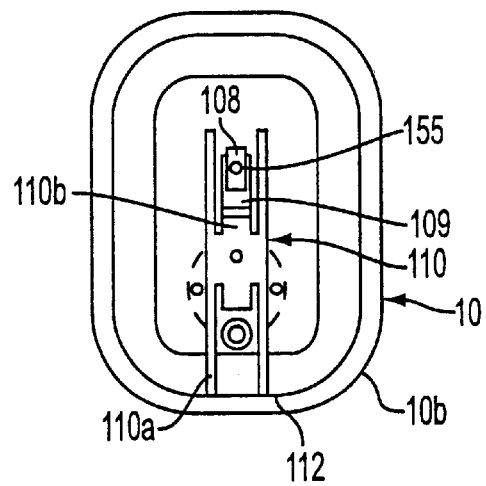
FIG. 17 is a cross sectional view taken along line 2—2 shown in FIG. 15.
Figure 18:
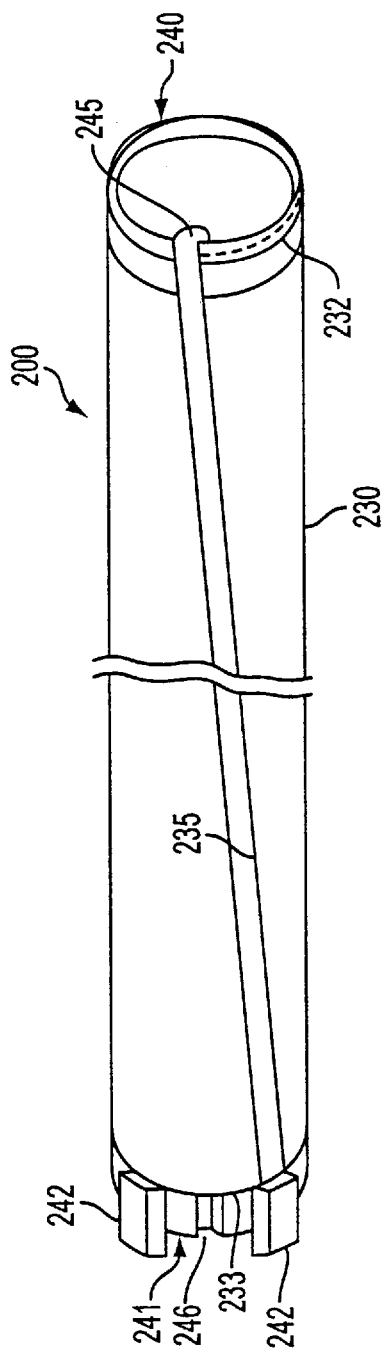
FIG. 18 is a perspective view illustrating a seed cartridge in accordance with the present invention.

Referring to FIGS. 15, 16 and 17, a first rack 102, which is supported and longitudinally displaceable within the housing 20, includes a plurality of gear teeth for interlocking engagement with the pinion section 101 of the control lever 125. A first gear 103 is rotatably mounted within housing 20 and has gear teeth that interlockingly engage the gear teeth of first rack 102. A second gear 104 is attached to first gear 103 so that the first and second gears rotate together and do not rotate relative to one another. The first and second gears 103, 104 may, for instance, by mounted on the same supporting shaft or be formed integrally together as a single unit. As is best illustrated in FIG. 16, second gear 104 is generally H-shaped, having a first set of gear teeth circumferentially formed on its major outside diameter and having a second set of centrally located gear teeth circumferentially formed on its minor outside diameter.

A proximal portion of the plunger 65 is illustrated in FIG. 15. It is understood that the distal end of the plunger 65 continues longitudinally through the fiberoptic channel 61 within portion 10a of the outer sheath 10 toward the distal end 13 of the device 1. The plunger 65 is substantially hollow 106 from end-to-end to facilitate insertion of a fiberoptic scope (rigid or flexible) or other optical means (e.g., rod lens scope, Hopkins type scope, laparoscope, endoscope, etc.) therein. The plunger 65 passes through an opening or fiberoptic port 80 in the proximal end 15 of the housing 20, as illustrated in FIG. 3, and terminates at its proximal end within a scope rest 160. The scope rest 160 is used to support the fiberoptic or optical scope, including the eyepiece, light guide post, camera head and light guide cable (not shown). A geared portion 105 of the plunger 65 proximate the second gear 104 has formed thereon a plurality of gear teeth for interlocking engagement with the second set of gear teeth centrally located on the second gear 104.

A third gear 107 of generally H-shaped configuration comprises an outer set of gear teeth 107a circumferentially formed on the major outside diameter of the third gear 107 and an inner set of centrally located gear teeth 107b circumferentially formed on the minor outside diameter of the third gear. The outer teeth 107a engage the first set of teeth on second gear 104 and the inner teeth 107b engage the teeth formed on the second rack 108, which second rack extends and is displaceable longitudinally within housing 20.

The second rack 108 is preferably rectangular in shape and has a proximal and a distal end. The second rack 108 includes a bore extending longitudinally from the proximal end of the rack 108 at least substantially to the distal end thereof. The distal end of an outer sheath adjustment rod 155 is received within the bore and rotatably connected to the second rack 108. The proximal end of the rod 155 extends through an opening in the proximal end 15 of the housing 20 and terminates in an adjustment knob 156. A plurality of pawls or gear teeth 109 are supported by the rod 155 proximate its distal end and project outwardly through an opening formed in the second rack 108. In this manner, rotation of the know 156 turns rod 155 relative to the second rack 108, thereby causing the rod and associated pawls 109 to move longitudinally within the opening formed in the second rack 108 (i.e., the pawls move relative the second rack).

A fourth gear 110 is rotatably mounted within housing 20 and is rotatable in only one direction. The fourth gear 110 is of generally H-shaped configuration comprising an outer set of gear teeth 110a circumferentially formed on the major outside diameter of the fourth gear 110 and an inner set of centrally located gear teeth 110b circumferentially formed on the minor outside diameter of the fourth gear. The inner set of centrally located gear teeth 110b interlockingly engage pawls 109 of the second rack 108 for driving the fourth gear 110 in a first direction. However, pawls 109 disengage from the teeth 110b of the fourth gear 110 when the fourth gear is driven in the opposite direction. As such, the second rack 108, pawls 109 and the fourth gear 110 generally act as a continuous ratchet type assembly wherein the longitudinal movement of the second rack 108 in one direction causes the fourth gear 110 to rotate in that direction, while longitudinal movement of the second rack 108 in the opposite direction disengages pawls 109 from the fourth gear 110 without moving the fourth gear. A one way clutch could also be operatively connected to the fourth gear 110 to permit the gear to be driven in only one direction (i.e., clockwise direction) by pawl 109 of the second rack 108.

The proximal portion 10b of the outer sheath 10 includes a set of gear teeth 112 that project inwardly within the second bore of portion 10b. The outer set of teeth 110a formed on the fourth gear 110 partially project through an opening or slot formed in the housing 20 in order to interlockingly engage the inwardly projecting gear teeth 112 formed on the proximal portion 10b of the outer sheath 10 so that rotation of the fourth gear 110 causes the outer sheath 10 to move longitudinally relative the housing 20.

As mentioned above, the distal portion 10a of outer sheath 10 has a first bore extending longitudinally to the distal end 13 of the device 1 in a similar manner to the outer sheath of the first embodiment. While not specifically illustrated in FIGS. 15–17, it is understood that the second embodiment of the FOGISMA device 1 comprises at least the introducer needle 12, seed transfer barrel housing 40, seed transfer barrel 45, advancing pin and ring assembly 50, linking shaft 55, elongated member 60, plunger 65 and seed lock 85 described above and illustrated in FIGS. 1–13 with respect to the first embodiment. These components are located within the first bore of the distal portion 10a of the outer sheath 10 proximate the distal end 13 of the FOGISMA device 1.

Referring now to FIG. 15, the linking shaft 55 has a distal end that is operatively connected to the advancing pin and ring mechanism 50 for controlling the longitudinal movement of the mechanism 50 relative to the multichamber seed transfer barrel 45. The proximal end of the linking shaft 55 is illustrated in FIG. 15 as being operatively connected to a hook member 117. Hook member 117 is preferably an elongated bar or rod having an upwardly extending flexible hook 117a projecting therefrom. The hook member 117 is located within and slidably supported by the housing 20 between the third and fourth gears 107, 110.

A fifth gear 114 is located within and rotatably supported by housing 20 proximate the second rack 108. The fifth gear 114 includes a set of gear teeth circumferentially formed thereon for interlockingly engaging a corresponding set of gear teeth 108a formed on at least a portion of the second rack 108. The gear teeth on the fifth gear 114 also interlockingly engage corresponding gear teeth formed on a third rack 115. Like the hook member 117, the third rack 115 is also located within and slidably supported by the housing 20 between the third and fourth gears 107, 110. A flexible hook or tooth 116 projects downwardly from the third rack 115 so that when the third rack 115 is driven longitudinally toward the hook member 117, the downwardly extending hook 116 in the third rack temporarily engages the upwardly extending hook 117a in the hook member 117.

It is understood that control lever 125 and gears 103, 104, 107, 110 may be rotatably mounted within the housing 20 in a conventional manner, such as by mounting each gear on a shaft or pin and rotatably supporting the shaft by a pair of suitable bearings or bushings mounted within the housing 20. In addition, hook member 117 and racks 102, 108, 115 may be slidably supported within the housing using suitable journals or bearings mounted within the housing 20.

The operation of the second embodiment of the FOGISMA device 1 is discussed below. Initially, to prepare the device 1 for operation, the surgeon or operator of the device will set the desired spacing between implanted seeds 3, 3a, . . . , 3n by turning the adjustment knob 156. As knob 156 is manually rotated, outer sheath adjustment rod 155 is moved longitudinally relative the second rack 108, thereby moving pawls 109 longitudinally within the opening of the second rack 108 relative the fourth gear 110. Because pawls 109 engage and drive the fourth gear 110, which fourth gear in turn drives the outer sheath 10 longitudinally relative the housing 20, the surgeon or operator of the FOGISMA device 1 is able to precisely set and control the longitudinal distance that the outer sheath 10 travels or advances relative the housing 20 each time the control lever 125 is fully actuated. That is, the surgeon or operator is able to precisely adjust the timing when pawls 109 engage the gear teeth of the fourth gear 110.

As illustrated in FIGS. 14 and 15, control lever 125 is capable of being actuated by the surgeon or operator of the FOGISMA device 1 from neutral position A to position B (actuated approximately 60° from position A) to position C (actuated approximately 75° from position A) and back to position A. As will be discussed in greater detail below, when the lever 125 is actuated from point A to point B as is illustrated in FIG. 15, the fiberoptic plunger 65 (and fiberoptic scope or other optical means received with the bore 106) is advanced through the seed transfer barrel 45 to the distal end 12a of the introducer needle 12. When the lever 125 is further actuated from point B to point C as is illustrated in FIG. 15, the outer sheath 10 is advanced a predetermined distance (as set by the surgeon or operator using the adjustment knob 156). Finally, when the lever 125 is released by the surgeon or operator of the FOGISMA device 1 and automatically returns from point C to point A by virtue of control lever spring 151 as illustrated in FIG. 15, the fiberoptic plunger 65 (and fiberoptic scope or other optical means) are withdrawn from the needle 12 and seed transfer barrel 45 toward the proximal end 15 of the device 1 and the seed transfer barrel 45 is indexed a predetermined amount.

Referring to FIG. 15, when the control lever 125 of the FOGISMA device 1 is actuated from point A to point B, the control lever 125 pivots about pin 150, thereby causing the pinion section 101 of the control lever 125 to rotate in a counterclockwise direction. Because the gear teeth on pinion section 101 engage mating gear teeth on the first rack 102, the first rack 102 is caused to move or is driven longitudinally toward the distal end 13 of the device 1. Such longitudinal displacement of the second rack 102 causes the first gear 103 to rotate in a counterclockwise direction due to the interlocking engagement of the gear teeth on the second rack 102 and first gear 103. Because second gear 104 is fixed to the first gear 103, the second gear 104 is also caused to rotate in the counterclockwise direction. Such counterclockwise rotation of the second gear 104 causes the fiberoptic plunger 65 (and fiberoptic scope or other optical means retained therein) to move longitudinally toward the distal end 13 of the device 1 due to the interlocking engagement of the first set of centrally located gear teeth on the second gear 104 with the gear teeth 105 formed on the plunger 65. Such longitudinal movement of the plunger 65 also compresses plunger return spring 123 with sufficient force to overcome the opposing biasing force of spring 123.

Once the lever 125 is actuated to point B (approximately 60° from point A), the last or proximal-most gear tooth 105 formed on the plunger 65 engages the teeth on the second fear 104. Since there are no teeth 105 formed on the plunger after this point or last tooth 105, continued counterclockwise rotation of gear 104 no longer longitudinally advances the plunger 65 toward the distal end 13 of the device 1.

Accordingly, when the lever 125 is at point B, the plunger 65 has advanced through the fiberoptic channel 61 in the elongated member 60, through chamber 48 of the seed transfer barrel 45, through threaded flange 42 to approximately the distal end 12a of the introducer needle 12. Thus, a seed 3 that had previously been loaded into chamber 48 of the transfer barrel 45 will have been fired or forced by the advancing plunger 65 out of the chamber 48, through the introducer needle 12, and deposited within the tumor 2.

The fiberoptic scope or other optical means (e.g., rod lens scope, Hopkins type scope, laparoscope, endoscope, etc.) (not shown) that is preferably retained within the bore 106 through the fiberoptic plunger 65, permits the surgeon or operator of the device 1 to view the proximal end of the seed 3 to ensure that the "fired" seed 3 exits the introducer needle 12 into the tumor 2 or other tissue. The fiberoptic scope or other optical means also facilitates visual inspection of the implanted seed 3 with the tumor 2 or other tissue. Such visual inspection of the implanted seed 3 permits the surgeon or operator of the device 1 to verify that the seed 3 had been implanted in the proper location of the tumor 2, or tissue. Such visual verification may be quite valuable where, for instance, there exists the possibility that the introducer needle 12 has penetrated beyond the tumor or tissue wall whereby implanted seeds 3 might otherwise by deposited in undesirable locations orifices within the patient.

In addition to advancing the plunger 65 to the distal end 12a of the introducer needle 12 when the control lever 125 is actuated from point A to point B, such counterclockwise rotation of the second gear 104 causes the third gear 107 to rotate in a clockwise direction due to the interlocking engagement of the mating outer circumferential gear teeth on the second and third gears. Such clockwise rotation of third gear 107 thereby causes the second rack 108 and pawl 109 to move longitudinally toward the proximal end 15 of the FOGISMA device 1.

Such longitudinal movement of the second rack 108 in the proximal direction causes: (1) the fifth gear 114 to rotate in a counterclockwise direction due to the interlocking engagement of gear teeth on the second rack 108 and fifth gear 114; and (2) pawls 109 to move longitudinally with the second rack in the proximal direction into contact with the inner gear teeth centrally located on the fourth gear 110 (but does not yet cause the fourth gear 110 to rotate). When the fifth gear 114 is driven in the counterclockwise direction by the second rack 108, the fifth gear 114 causes the third rack 115 to move longitudinally toward the distal end 13 of the device 1 due to the interlocking engagement of gear teeth on the fifth gear 114 and the third rack 115. Such longitudinal movement of the third rack 115 cause the engaging hook 116 on the third rack 115 to move toward (but not yet engage) the hook 117a of hook member 117.

Thus, when the control lever 125 is actuated to point B as illustrated in FIG. 15, the fiberoptic plunger 65 (and fiberoptic scope or other optical means) is advanced to the distal end 12a of the introducer needle 12 and the outer sheath 10 is about to advance.

Referring to FIG. 15, when the control lever 125 of the FOGISMA device 1 is further actuated from point B to point C (e.g., approximately 75° from point A), the control lever 125 pivots further about pin 150, thereby causing the pinion section 101 of the control lever 125 to continue to rotate in a counterclockwise direction. Such continued counterclockwise rotation of pinion section 101 drives the first rack 102 longitudinally toward the distal end 13, thereby causing the first and second gears 103 and 104 to rotate further in the counterclockwise direction. Because the gear teeth formed on the second gear 104 no longer engage any additional gear teeth 105 formed on the fiberoptic plunger 65, the plunger 65 (and fiberoptic scope or optical means) does not advance further longitudinally in the direction of the distal end 13 of the FOGISMA device 1. However, the distal end of the plunger 65 remains in its advanced position at the distal end 12a of the introducer needle 12 (with spring 123 remaining in a compressed state).

The continued counterclockwise rotation of the second gear 104 drives the second rack 108 further in the longitudinal direction toward the proximal end 15 of the device 1. Such further movement of the second rack 108 drives the fifth gear 114 in the clockwise direction, thereby driving the third rack 115 longitudinally toward the hook member 117 so that the engaging hook 116 on the third rack 115 releasingly engages the hook 117a of the hook member 117. Because the hooks 116, 117a are made of a flexible, resilient material, the hooks deform slightly to permit the engaging hook 116 to travel slightly beyond and engage book 117a. Upon engagement with one another, the hooks 116, 117a resiliently return to their original shape to maintain such locking engagement until a sufficient releasing force is applied to again deform the hooks when the third rack 115 is moved longitudinally away from hook member 117 in the proximal direction.

In addition, the continued longitudinal movement of the second rack 108 (and therefore of the pawls 109) in the direction of the proximal end 15 of the device 1 causes pawls 109 to engage the centrally located inner gear teeth 110b formed in the fourth gear 110, thereby causing the fourth gear 110 to rotate in the clockwise direction (fourth gear 110 is only permitted to rotate in the clockwise direction). When the fourth gear 110 rotates in the clockwise direction, the outer sheath 10 is caused to precisely move or advance longitudinally relative housing 20 toward the distal end 13 of the device 1 due to the interlocking engagement of the outer circumferential gear teeth 110a formed in the fourth gear 110 with the gear teeth 112 formed on the interior of the outer sheath 10.

Since the distal end 13 of the outer sheath 10 is intended to abut the wall of the tumor 2 or other body tissue of the patient, a template or a grid during operation of the FOGISMA device 1, the above-described longitudinal movement of the outer sheath 10 in the distal direction relative housing 20 (and therefore relative introducer needle 12) will cause the introducer needle 12 to withdraw a predetermined distance from the tumor 2 or other tissue in which the needle has penetrated, thereby leaving a seed 3 (previously advanced by plunger 65 through the implantation needle 12) implanted in the tumor 2. The predetermined distance that the needle 12 moves relative the outer sheath 10 due to advancement of the outer sheath relative the housing 20 controls the spacing between implanted seeds 3, 3a, . . . , 3n within the tumor 2 and is established by the surgeon or operator of the FOGISMA device 1 by turning the adjustment knob 156 as described above to adjust the timing when pawls 109 engage the fourth gear 110.

Thus, when the control lever 125 is actuated to point C as illustrated in FIG. 15, the fiberoptic plunger 65 (and fiberoptic scope or other optical means) remains in the advanced position at the distal end 12a of the introducer needle 12 and the outer sheath 10 has been advanced a predetermined distance toward the distal end 13 of the device 1 relative the housing 20, thereby partially withdrawing the needle 12 from the tumor 2 by that predetermined distance.

With reference to FIG. 15, when the actuated control lever 125 of the FOGISMA device 1 is thereafter released by the surgeon or operator, the spring 151 biases the control lever 125 back to the neutral position from point C to point A. When this occurs, the control lever 125 pivots about pin 150, thereby causing the pinion section 101 of the control lever 125 to rotate in a clockwise direction. Such clockwise rotation of pinion section 101 drives the first rack 102 longitudinally toward the proximal end 15, thereby causing the first and second gears 103 and 104 to rotate in a clockwise direction. The clockwise rotation of second gear 104 causes the gear teeth formed on the second gear 104 to once again engage the gear teeth 105 formed on the fiberoptic plunger 65, thereby driving (with the assistance of spring 123) the plunger 65 (and fiberoptic scope or other optical means) longitudinally in the direction of the proximal end 15 of the FOGISMA device 1. At this point, the distal end of the plunger 65 is returned to its original position and no longer extends within the introducer needle 12 or seed transfer barrel 45.

The clockwise rotation of the second gear 104 also drives the second rack 108 in the longitudinal direction back to its original position toward the distal end 13 of the device 1. Such return movement of the second rack 108 also causes pawls 109 to disengage and move away from the fourth gear 110. The fourth gear 110, which can only rotate in the clockwise direction, is not driven by the disengaging pawls 109 when the second rack moves longitudinally toward the distal end 13 of the device 1. As such, the outer sheath 10 does not move when the control lever 125 returns from point C to the neutral position at point A and the control lever 125 remains in the advanced position which occurred when the lever 125 was previously actuated from point B to point C.

The return movement of the second rack 108 also drives the fifth gear 114 in the counterclockwise direction, thereby driving the third rack 115 longitudinally away the hook member 117 to its original position. Because of the engagement of hooks 116, 117a the movement of the third rack 115 toward the proximal end 15 of the device 1 causes the hook member 117 to also move longitudinally in the proximal direction. Such longitudinal movement of the hook member 117 causes the advancing pin and ring assembly 50 to similarly move longitudinally relative the seed transfer barrel 45 toward the proximal end 15 of the FOGISMA device 1 due to the connection of the hook member 117 with the advancing pin and ring assembly 50 by the linking shaft 55, thereby compressing spring member 58 located within the need transfer barrel housing 40.

As discussed above with respect to FIGS. 5–10 and 12A–12C, when the advancing pin and ring assembly 50 moves in the proximal direction relative the seed transfer barrel 45, the first barrel advancing tools 51a formed on the assembly 50 moves out of the relieved portion 41 and engages a distal cam portion 46a of the transfer barrel 45, while the second barrel advancing tooth 51b disengages from the proximal cam portion 46b of the transfer barrel 45. Engagement of the first barrel advancing tooth 51a with one of the distal cam portions 46a causes the seed transfer barrel (and seed 3a contained therein) to rotate a predetermined amount, as is illustrated in FIG. 12B. As mentioned above, a preferred embodiment of the seed transfer barrel 45 includes a total of eight equally spaced cam portions 46, so that the predetermined rotation of the multichamber transfer barrel 45 is precisely one-eighth of a revolution.

Once the transfer barrel 45 is actuated that predetermined amount (e.g., one-eighth revolution) by the first barrel advancing tooth 51a, the resultant force opposing continued longitudinal movement of hook member 117 in the proximal direction exceeds the holding force of the engaged hooks 116, 117a, thereby deforming and disengaging the hooks from one another. The third rack 115 continues to be driven in the proximal direction back to its original position and the spring member 58 biases the advancing pin and ring mechanism 50 distally back to its original position with the first barrel advancing tooth 51a again received within the relieved portion 41 and disengaged from the distal cam portion 46a of the transfer barrel 45, while the second barrel advancing tooth 51b again engaging one of the proximal cam portions 46b of the transfer barrel 45. Engagement of the second barrel advancing tooth 51b with one of the proximal cam portions 46b causes the seed transfer barrel to further rotate a predetermined amount. In the embodiment of the seed transfer barrel 45 having a total of eight equally spaced cam portions 46, this predetermined rotation of the multichamber seed transfer barrel 45 is precisely one-eighth of a revolution (or a total of one-quarter of a revolution from actuation of the control lever 125 to release thereof), as illustrated in FIG. 12C.

By rotating the seed transfer barrel 45 a total of 90° when the control lever 125 returns to neutral point A from point C, the next or subsequent seed 3b (not shown) within alignment chamber 62, which seed 3b was adjacent to the seed 3a previously loaded into the adjacent seed chamber 48, is biased into the empty seed chamber 48 of the transfer barrel 45 that is now aligned with the seed alignment channel 62. In addition, the seed chamber 48 containing seed 3 as illustrated in FIG. 12C has rotated 90° so that the seed chamber 48 containing seed 3 is now aligned with fiberoptic channel 61, plunger 65, the bore through introducer needle 12 and the aperture through flange 42. Thus, the seed 3 illustrated in FIG. 12C is now in position to be fired or driven by the plunger 65 into the tumor 2 when the surgeon or operator of the FOGISMA device 1 once again actuates the control lever 125 from point A to point B.

It is understood that the number of seed channels 48 and cam portions 46 in the seed transfer barrel 45 may vary depending upon the application and that the above-described embodiment of the seed transfer barrel 45 having eight cam portions and four seed transfer channels is illustrative of one preferred arrangement. Another possible arrangement could include two seed chambers 48 spaced 180° apart from one another and four cam portions 46 (each providing 45° rotation of the seed transfer barrel 45 when engaged-by one of the advancing pin teeth 51a, 51b of the advancing pin and ring assembly 50).

Thus, when the control lever 125 returns from point C to the neutral position at point A as illustrated in FIG. 15, the fiberoptic plunger 65 (and fiberoptic scope or other optical means) retract from the introducer needle 12 and seed transfer barrel 45 to the original position within the fiberoptic channel 61, and the seed transfer barrel 45 is rotated a predetermined amount in order to place the next seed within the transfer barrel in position for firing through needle 12 and to load another seed from the seed alignment channel 62 into an empty seed chamber 48 in the barrel 45.

It is also understood that the present invention is not limited to any particular tooth configuration of the various gears, pinions and racks described herein. However, it is preferable that the teeth of these gears, pinions and racks be very fine and precise to facilitate accurate control and operation of the FOGISMA device 1. These gears, pinions and racks may preferably be manufactured in a conventional manner from any suitable material that is capable of withstanding conventional medical instrumentation sterilization techniques (e.g., autoclave, radiation, x-ray, or ethylene oxide gas sterilization) and is acceptable for such medical procedures (e.g., plastic, stainless steel, etc.).

A first disengagement lever 124 having a wedge-shaped portion may also be provided on the housing 20 to selectively disengage the third gear 107 from the second rack 108, as is illustrated in FIGS. 14 and 15. Selective actuation of the first disengagement lever 124 will cause the gear 107 to move slightly away from the second rack 108, or vice versa, just enough to disengage their respective gear teeth. When the third gear 107 is disengaged from second rack 108, the surgeon or operator of the device 1 can actuate the control lever 125 to move the fiberoptic plunger 65 longitudinally through the device 1 without operating any of the other components of the device 1. This may be useful during set-up of the FOGISMA device 1, for instance, to initially insert the needle 12 into the target tissue prior to implantation. Thus, the advanced plunger 65 may be used as a stylet to prevent introduction of tissue into the bore of the needle 12 and for viewing the implantation site prior to implantation. Once this is accomplished, the first disengagement lever 124 may be actuated to return to its original position wherein the third gear 107 and second rack 108 are again in meshing engagement with one another.

A second disengagement lever 122 having a wedge-shaped portion may also be provided on the housing 20 to selectively disengage the fourth gear 110 from the gear teeth 112 formed on the interior of the outer sheath 10, as is illustrated in FIGS. 14 and 15. Selective actuation of the second disengagement lever 122 will cause the fourth gear 110 to move slightly away from gear teeth 112 on the outer sheath 10 just enough to disengage the two from one another. When the fourth gear 110 is in disengaged position relative outer sheath gear teeth 112, the surgeon or operator of the device 1 can manually adjust the longitudinal location of the outer sheath 10 relative the housing 20. This may be useful during set-up of the FOGISMA device 1, for instance, to set the desired starting position of the outer sheath 10. Calibrated markings or indicia (not shown) may be provided on the housing 20 relative the proximal end of the outer sheath 10 to precisely set the depth of the introducer needle 12 according to the desired specification. Selective actuation of the second disengagement lever 122 may also be useful during set-up of the FOGISMA device 1, for instance, to load seeds 3, 3a, . . . , 3n into respective chambers 48 of the multichamber seed transfer barrel 45 in order to position a seed in the firing position (e.g., in aligned relation to the plunger 65 and needle 12). Once set-up is complete, the second disengagement lever 122 may be actuated to return to its original position wherein the fourth gear 110 again interlockingly engages the outer sheath gear teeth 112.

The housing 20 of the FOGISMA device 1 may also be provided with a seed counter indicator 9 for visually providing a numerical cumulative seed tally of implanted "fired" seeds 3 and "unfired" seeds 3a, 3b . . . , 3n remaining in the device 1. The seed counter 9 may preferably be a conventional gear-type counter mechanism that actuates each time a seed 3 is fired or discharged from the device 1 through needle 12. The conventional gear-type counter mechanism may, for instance, be operatively connected to any one of the elements (e.g., control lever pinion section 101, first rack 102, first gear 103, second gear 104, or plunger gear teeth 105) that drive the plunger 65 through the needle 12 to fire or discharge a seed 3 from the device 1. In the embodiment illustrated in FIG. 15, the seed counter indicator 9 is actuated by an actuator rod 126 that is connected to the proximal end of the second rack 108. Thus, each time the second rack 108 is driven longitudinally to advance the multichamber seed transfer barrel 45, the actuator rod 126 moves into engagement with the seed counter indicator 9 and causes the seed counter indicator 9 to actuate one numerical value. The seed counter indicator 9 includes a visual display of the number of seeds fired from the device 1, which visual display is preferably provided on the housing 20, as illustrated in FIGS. 2, 3, 14 and 15.

In either of the above-described embodiments of the FOGISMA device 1, it is necessary to load the seeds 3, 3a, . . . , 3n into the device 1. Referring to FIGS. 18–21, there is illustrated a Brachytherapy Interstitial Seed Cartridge ("BISC" or "seed cartridge") 200 that is ideally suited for use in conjunction with the FOGISMA device 1. It is understood, however, that the seed cartridge 200 may also be easily adapted to fit existing interstitial seed applicators.

In one embodiment of the seed cartridge 200 illustrated in FIGS. 18–21, a cylindrically-shaped inner core 210 is provided having multiple chambers 212 extending longitudinally therethrough. The inner core 210 is preferably made of either plastic or metal, and includes a plurality of substantially parallel seed chambers or conduits 212a, 212b, 212c and 212d extending longitudinally from a proximal end 214 of the core 210 to a distal end 215 of the core 210.

Each conduit 212a, 212b, 212c, 212d is generally slightly larger than the diameter of the seeds 3, 3a, . . . 3n for receiving the seeds in end-to-end aligned relation. While the length of the inner core 210 dictates the number of seeds that may be held in each seed conduit 212, each conduit 212a, 212b, 212c, 212d preferably holds up to 25 seeds 3, 3a, . . . , 3n in end-to-end aligned relation.

For each seed conduit 212a, 212b, 212c, 212d, a longitudinal slot or opening 220 is formed in the circumference of the inner core 210, which opening 220 extends from the proximal end 214 to the distal end 215 of the inner core 210. Each opening 220 is tangential to one of the seed conduits 212a, 212b, 212c, 212d so that each seed conduit is open or slotted about the circumference of the inner core 210.

The inner core 210 is contained within a cylindrically-shaped outer sleeve 230. The outer sleeve 230 includes a bore extending longitudinally from the proximal end 232 of the outer sleeve 230 to the distal end 233 of the outer sleeve.

The diameter of the bore through the outer sleeve 230 is preferably slightly larger than the outside diameter of the inner core 210 so that the inner core 210 may be received within the bore of the outer sleeve 230.

The outer sleeve 230 is preferably made from lead or steel in order to effectively shield personnel handling the seed cartridge 200 from exposure to the seeds 3 contained therein (e.g., radioactive or chemical exposure). It is understood, however, that other materials such as plastic may be utilized in making the outer sleeve 230 and that a protective insulating layer of lead or steel may be applied or bonded to the outer sleeve 230 to provide the desired protection from radiation exposure.

Figure 21:
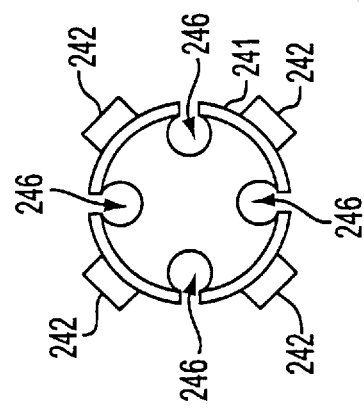
FIG. 21 is an elevational view of a distal end cap of the seed cartridge shown in FIG. 18.
Figure 20:
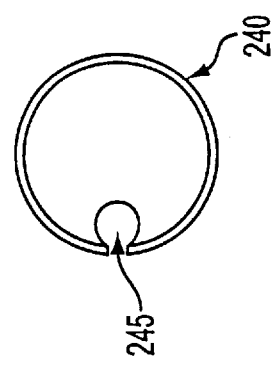
FIG. 20 is an elevational view of a proximal end cap of the seed cartridge shown in FIG. 18.
Figure 19:
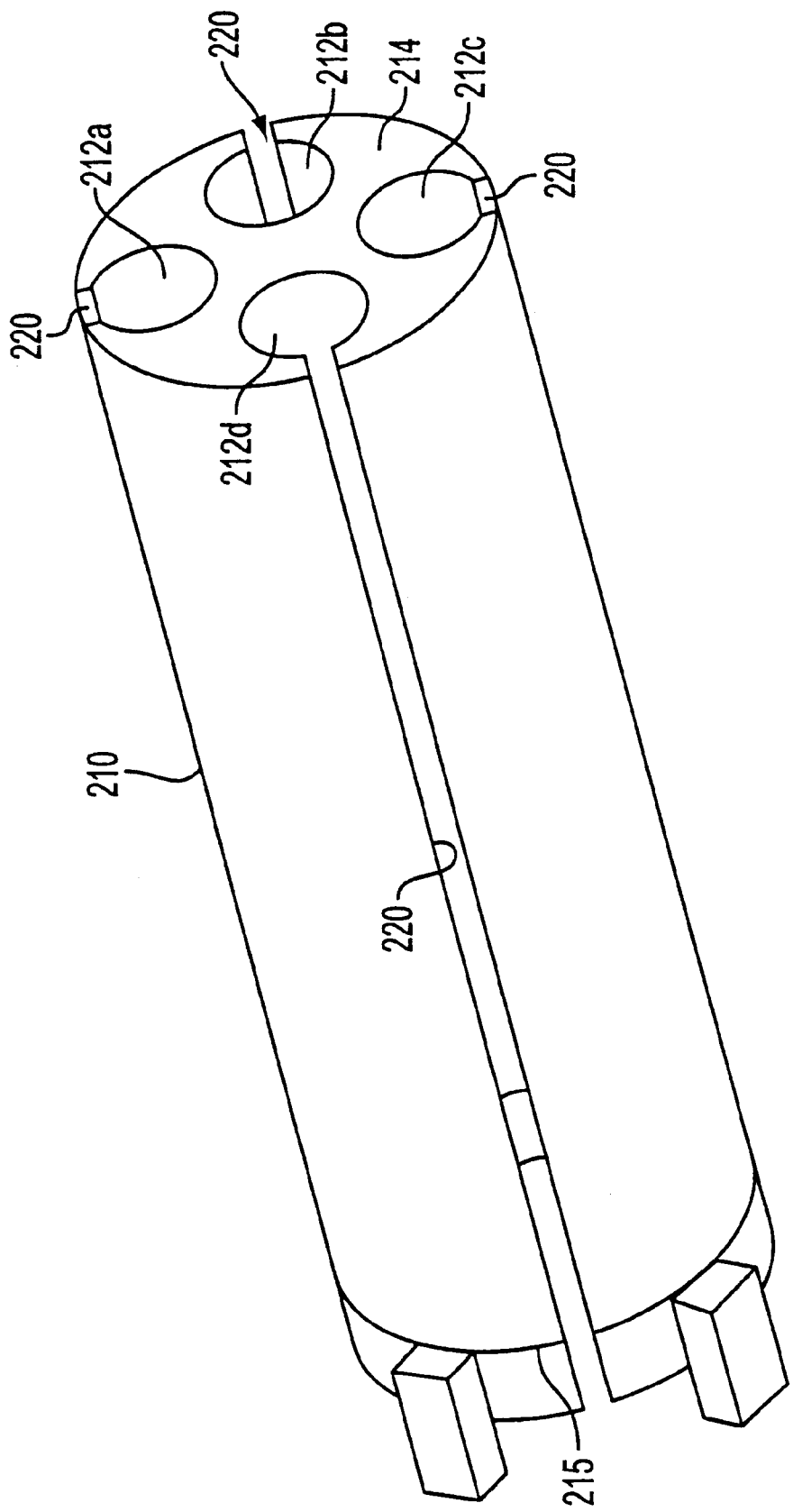
FIG. 19 is a perspective view illustrating the core member of the seed cartridge shown in FIG. 18.

The outer sleeve 230 has a circumferential slot 235 extending from the proximal end 232 to the distal end 233 of the sleeve. The depth of the slot 235 is such as to terminate within the bore of the outer sleeve 230; that is, the slot 235 extends into the bore of the sleeve 230. Unlike the openings 220 of the inner core 210, which are generally straight, the slot 235 formed in the outer sleeve 230 is substantially S-shaped or curved along the circumference of the outer sleeve 230, as is best illustrated in FIG. 21. The preferred slot 235 is configured so that when the inner core 210 is received within the outer sleeve 230, only one seed 3 in any of the seed channels 212a, 212b, 212c, 212d may be visible through a conduit opening 220 of the inner core 210 in alignment with the slot 235 of the outer sleeve 230. This configuration, therefore, effectively shields personnel from exposure to the seeds 3 contained in the seed cartridge 200.

While the inner core 210 preferably includes four substantially parallel seed conduits 212a, 212b, 212c and 212d, it is understood that the present invention is not limited to this number of conduits. For instance, the inner core 210 may only include three substantially parallel seed conduits 212a, 212b, 212c so that the outer sleeve 230 may be rotated relative the inner core 210, or vice versa, to a neutral position where the slot 235 does not intersect with any conduit opening 220 in the inner core 210. Thus, in this neutral position, no seeds 3, 3a, . . . , 3n within seed conduits 212a, 212b, 212c are visible through the opening 220 and slot 235, thereby minimizing or preventing radiation exposure from the seeds.

A proximal end cap 240 is releasably secured or otherwise connected to the proximal end 232 of the outer core 210 and a distal end cap 241 is releasably secured or otherwise connected to the distal end 215 of the inner core 210. This is preferably accomplished after the inner core 210 is received within the bore of the outer sleeve 230. The end caps 240, 241 are generally cylindrical in shape and a preferred method of securing the end caps 240, 241 to the outer sleeve 230 and inner core 210, respectively, is by forming threads on the end caps 240, 241 for threadedly engaging mating threads formed on the outer sleeve 230 and inner core 210.

Like the outer sleeve, the end caps 240, 241 are preferably made from lead or steel in order to effectively shield personnel handling the seed cartridge 200 from radioactive exposure to the seeds 3 contained therein. Alternatively, a lead foil may be inserted between each end cap 240, 241 and the inner core 210, which foil may be penetrated by a push rod or other device 250 (FIG. 28) in order to discharge seeds 3, 3a, . . . , 3n out of the BISC seed cartridge 200.

The proximal end cap 240 includes at least one cut-out section 245 passing therethrough so that when the end cap 240 is secured to the outer sleeve 230 containing the inner core 210, the cut-out 245 is in aligned relationship with the particular seed conduit 212a, 212b, 212c, 212d of the inner core 210 that is proximate the slot 235 of the outer sleeve 230, as well as that portion of the slot 235 proximate the proximal end 232 of the outer sleeve 230.

Similarly, the distal end cap 241 includes a plurality of apertures 246 formed therein. When the distal end cap 241 is secured to the inner core 210, each aperture 246 is in aligned relationship with one of the seed reservoirs 212a, 212b, 212c, 212d and the opening 220 associated with that particular seed conduit of the inner core 210. The same overall configuration of each aperture 246 is generally the same as the seed conduit 212 and corresponding opening 220. The seed cartridge 200 is assembled by inserting the inner core 210 (containing seeds 3, 3a, . . . , 3n) within the outer sleeve 230 and securing the end caps 240, 241 to the proximal end 232 of the outer sleeve and distal end 215 of the inner core, respectively. The assembled BISC seed cartridge 200 may then be operably connected to the FOGISMA device 1 by aligning the distal end cap 241 with the seed insertion port 81 formed in the housing 20 of the device 1. The seed insertion port 81 preferably extends through the housing 20 from the proximal end 15 of the device 1 and is collinear with the seed alignment channel 62 formed in the elongated member 60.

A relieved portion or keyhole 82 is preferably formed in the proximal end 15 proximate the seed insertion port 81 for receiving a locking key 242 formed on the distal end cap 241. The locking key 242 projects outwardly from the circumference of the end cap 241 and is received within the relieved portion 82 to operatively connect the assembled seed cartridge 200 to the FOGISMA device 1. Once key 242 is received within the keyhole 82, the seed cartridge 200 is rotated slightly to releasably lock the key 242 within keyhole 82. The opposite rotation of the seed cartridge 200 back to its original inserted position will release the seed cartridge 200 from the device 1.

When the seed cartridge 200 is releasably locked to the FOGISMA device 1, one of the seed channels 212, apertures 245, insertion port 81 and the seed alignment channel 62 are in aligned relationship (i.e., collinear). In this manner, an elongated seed advancement push rod 250 may be inserted longitudinally through the cut-out 245 of proximal end cap 240 and into the seed conduit 212 aligned with the cut-out 245. A tab 251 projects upwardly from the push rod 250 and extends through the opening 220 associated with the seed conduit 212 in which the push rod 250 is received. The tab 251 also extends through the S-shaped slot 235 of the outer sleeve 230.

Thus, seeds 3, 3a, . . . , 3n contained within a particular seed conduit 212 of the inner core 210 may be advanced or loaded into the FOGISMA device 1 in the following manner. After the assembled BISC seed cartridge 200 is operably connected to the device 1 (e.g., via locking key 242), the push rod 250 is inserted longitudinally through the cut-out 245 of proximal end cap 240 and at least partially into the seed conduit 212 aligned with the aperture 245. The surgeon or operator of the device 1 is able to move the push rod 250 longitudinally through the seed conduit 212 toward the FOGISMA device 1 by grasping the push rod tab 251 extending through opening 220 and S-shaped slot 235. As the tab 251 advances distally through the S-shaped slot 235 of the outer sleeve 230, the outer sleeve is rotated relative the inner core 210 due to the S-shaped configuration of the slot 235 so that only one seed contained within the channel 212 bearing the push rod 250 is visually exposed through the opening 220 of the inner core 210 and slot 235 of the outer sleeve 230. Such continued distal movement of the push rod 250 through the seed conduit 212 causes seeds 3, 3a, . . . , 3n to advance in end-to-end aligned relation through aperture 245 in end cap 241 out of the seed cartridge 200, through the seed insertion port 81, and into the seed alignment channel 62 of the FOGISMA device 1.

The capability of the seed cartridge 200 to expose only one seed at a time through the opening 220 of the inner core 210 and slot 235 of the outer sleeve 230 minimizes exposure of the surgeon or operator handling the seed cartridge 200 to the seeds 3, 3a, . . . , 3n contained therein. In addition, such exposure of only one seed at a time permits the surgeon or operator to survey, inspect or otherwise measure the physical condition and characteristics (e.g., chemical or radioactive strength) of each seed contained within the seed cartridge 200.

Once the seeds 3, 3a, . . . , 3n are ejected from the BISC seed cartridge 200 into the seed alignment channel 62, the push rod 250 may be removed from the seed cartridge 200 and the seed cartridge may be removed from the FOGISMA device 1 by rotating the locking key 242 projecting from the distal end cap 241 relative the keyhole 82 of the housing 20 to disengage the key 242.

If a greater number of seeds 3 are still required for the particular medical procedure, then the surgeon or operator of the device 1 may rotate the outer sleeve 230 relative the inner sleeve 210 to align a new seed conduit 212b (containing seeds 3) with S-shaped slot 235 of the outer sleeve 230. The seed cartridge 200 may then be lockingly secured to the device 1 in the manner described above so that the new seed conduit 212b is in aligned relation to the seed insertion port 81 and seed alignment channel 62 of the FOGISMA device 1. The push rod 250 would then be inserted within and advanced through the new seed conduit 212b in the manner described above. Additional seed conduits 212c, 212d, etc. may be used in the above-described manner for insertion of an even greater number of aligned seeds 3. It is understood that the FOGISMA device 1 may be provided with more than one keyholes 82 and/or locking key 242 so that additional seed conduits 212 of the seed cartridge may be aligned with the seed insertion port 81.

Once all of the seeds 3, 3a, . . . , 3n are loaded in end-to-end aligned relation into the FOGISMA device 1, the BISC seed cartridge 200 is removed from the device and the seed biasing member 70 (described above) is inserted into the seed insertion port 81 to bias the seeds within the seed alignment channel 62 toward the multichamber seed transfer barrel 45.

Referring now to FIGS. 24–28, another embodiment of the BISC seed cartridge 300 is illustrated having a generally cylindrically-shaped inner core or seed cassette 310 having multiple chambers or conduits 312 extending longitudinally therethrough. The inner core 310 is preferably made of either plastic or metal, and includes a plurality of substantially parallel seed conduits 312 extending longitudinally from end to end.

Each conduit 312 is generally slightly larger than the diameter of the seeds 3, 3a, . . . 3n for receiving the seeds in end-to-end aligned relation. While the length of the inner core 310 dictates the number of seeds that may be held in each seed conduit 312, each conduit 312 preferably holds between approximately 25–30 seeds 3, 3a, . . . , 3n in end-to-end aligned relation.

For each seed conduit 312, a longitudinal slot or opening 320 is formed in the circumference of the inner core 310, which opening 320 extends from end to end of the inner core 310. Each opening 320 is tangential to one of the seed conduits 312 so that each seed conduit is open or slotted about the circumference of the inner core 310. While the inner core 310 preferably includes four substantially parallel seed conduits 312, it is understood that the present invention is not limited to this number of conduits.

The inner core 310 is contained within a cylindrically-shaped outer sleeve 330. The outer sleeve 330 includes a bore extending longitudinally from the proximal end 332 of the outer sleeve 330 to the distal end 333 of the outer sleeve. The diameter of the bore through the outer sleeve 330 is preferably slightly larger than the outside diameter of the inner core 310 so that the inner core 310 may be received within the bore of the outer sleeve 330. It is understood that the inner core 310 and outer sleeve 330 may be integrally formed as one piece.

The outer sleeve 330 is preferably made from lead or steel in order to effectively shield personnel handling the seed cartridge 300 from radioactive exposure to the seeds 3 contained therein. It is understood, however, that other materials such as plastic may be utilized in making the outer sleeve 330 and that a protective insulating layer of lead or steel may be applied or bonded to the outer sleeve 330 to provide the desired protection from radiation exposure.

Figure 22:
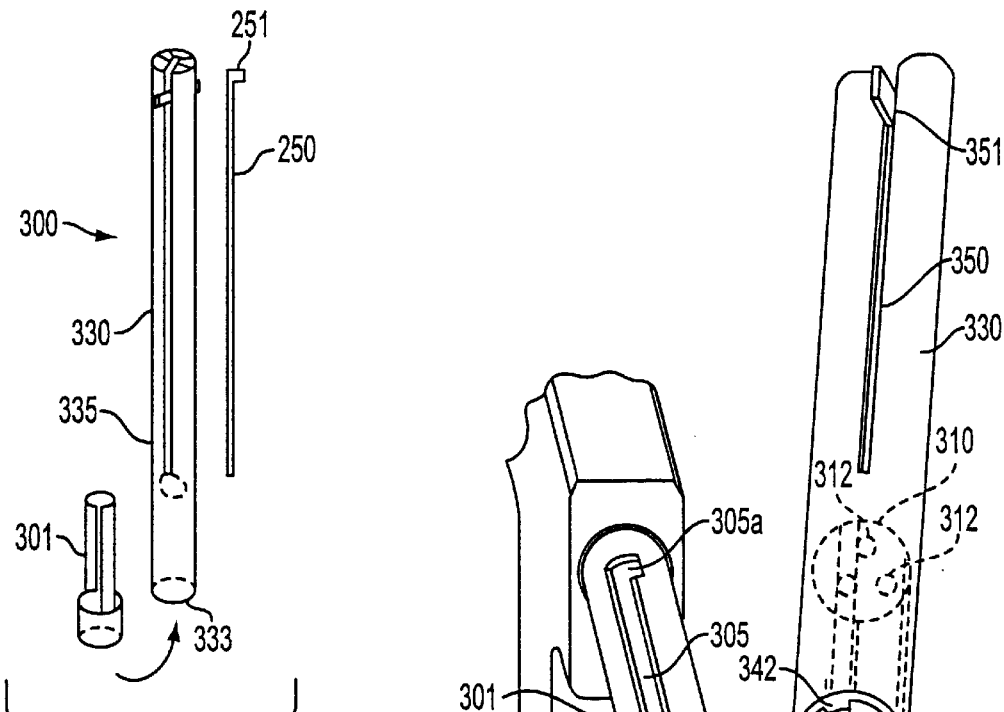
FIG. 22 is an exploded view of a second embodiment of the seed cartridge in accordance with the present invention.

The outer sleeve 330 has a circumferential slot 335 extending longitudinally from the proximal end 332 to the distal end 333 of the sleeve. The depth of the slot 335 is such as to terminate within the bore of the outer sleeve 330; that is, the slot 335 extends into the bore of the sleeve 330. Unlike the S-shaped slot 235 of the previously-described embodiment of the seed cartridge 200, the slot 335 formed in the outer sleeve 330 is substantially straight along the circumference of the outer sleeve 230, as is best illustrated in FIGS. 22, 26 and 27.

The outer sleeve 330 is longer than the inner core 310 so that a portion of the interior of the outer sleeve 330 proximate the distal end 333 thereof is substantially open when the inner core 310 is inserted or formed within the bore of the outer sleeve 330. A plurality of spaced apart locking keys 342 are formed proximate the distal end 333 of the outer sleeve 330 and project inwardly into the bore thereof.

An alignment adaptor/seed repository 301 is utilized to operatively connect the outer sleeve/inner core assembly 310, 330 to the FOGISMA device 1. The adaptor 301 is generally cylindrical in shape with a bore extending therethrough. The alignment adaptor 301 has a raised shoulder 302 proximate the distal end 303 of the adaptor 301. The raised shoulder 302 is received within the seed insertion port 81 formed in the proximal end 15 of housing 20 and is connected thereto in a conventional manner (e.g., threaded engagement). When installed, the bore through the adaptor 301 is in aligned relation (e.g., collinear) to the seed alignment channel 62 of the FOGISMA device 1.

Preferably, the BISC seed cartridge 300 will be provided to the surgeon or operator of the FOGISMA device 1 pre-loaded with seeds 3, 3a, . . . , 3n. At that time, the alignment adaptor/seed repository 301 may be releasably connected to the outer sleeve 330 in order to seal or otherwise plug the inner core/outer sheath assembly 310, 330 prior to use of the seeds. Furthermore, as is discussed further below, the alignment adaptor/seed repository 301 may also be used to store unused seeds following termination of the brachytherapy procedure. First and second film dams 317, 359 may be utilized to seal the inner core/outer sleeve assembly and to maintain a sterile environment for the seeds.

Figure 23:
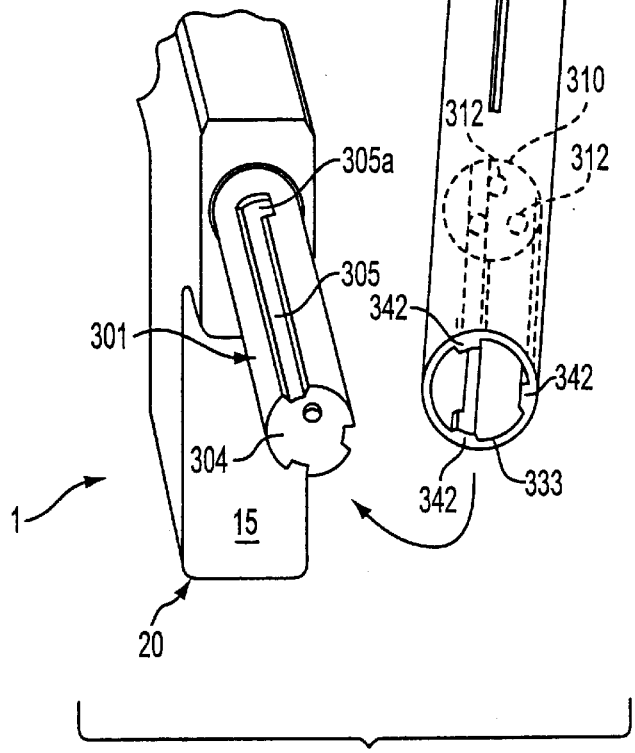
FIG. 23 is a perspective view illustrating attachment of the seed cartridge shown in FIG. 22 to the fiberoptic-guided interstitial seed manual applicator.
Figure 24:
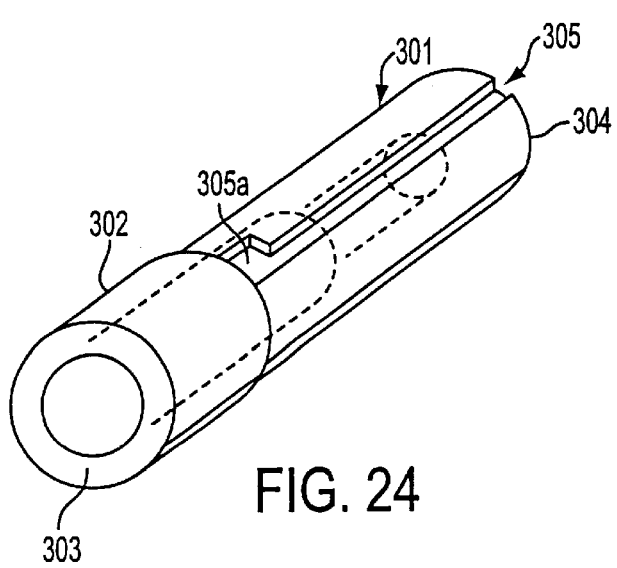
FIG. 24 is a perspective view of the alignment adaptor/seed repository used to attach the seed cartridge to the fiberoptic-guided interstitial seed manual applicator.

Referring to FIGS. 23 and 24, a plurality of spaced apart grooves or slide locks 305 are formed on the circumference of the adaptor 301 and extend longitudinally from approximately the raised shoulder 302 to the proximal end 304 of the adaptor 301. The grooves 305 are spaced apart along the circumference of the adaptor 301 so that each groove is aligned with one of the locking keys 342 formed on the outer sleeve 330 when the outer sleeve is slid onto the alignment adaptor 301. A notched or locking portion 305a of each groove 305 extends tangentially along the circumference of the adaptor at approximately 90° to the groove 305. As such, the outer sleeve 330 may be slid onto the alignment adaptor 301 by aligning and inserting the keys 342 within the grooves 305. Rotational or twist lock action of the outer sleeve 330 relative the adaptor 301 causes the keys 342 to lockingly engage the notched portions 305a. Similarly, rotation of the outer sleeve in the opposing direction disengages the keys 342 from notched portions 305 so that the outer sleeve 330 may be removed from the alignment adaptor 301.

Figure 30:
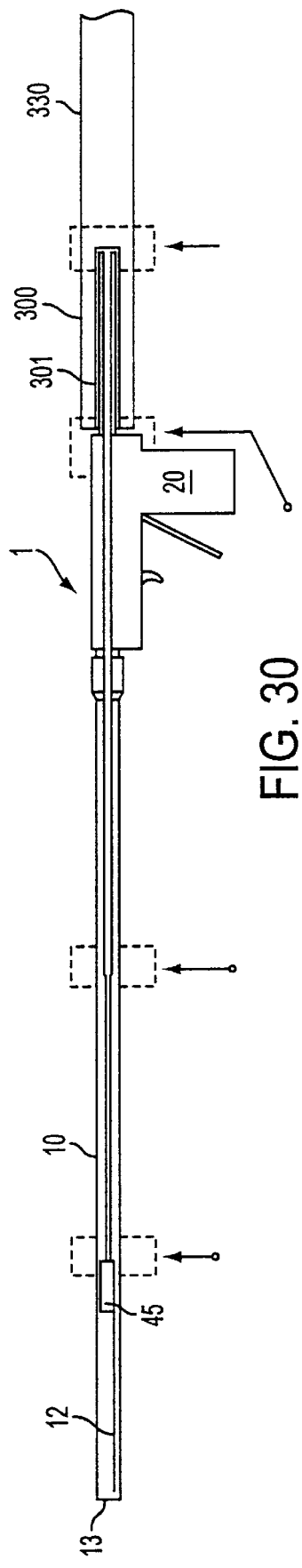
FIG. 30 illustrates the seed cartridge operably connected to the fiberoptic-guided interstitial seed manual applicator in accordance with the present invention.
Figure 31A:
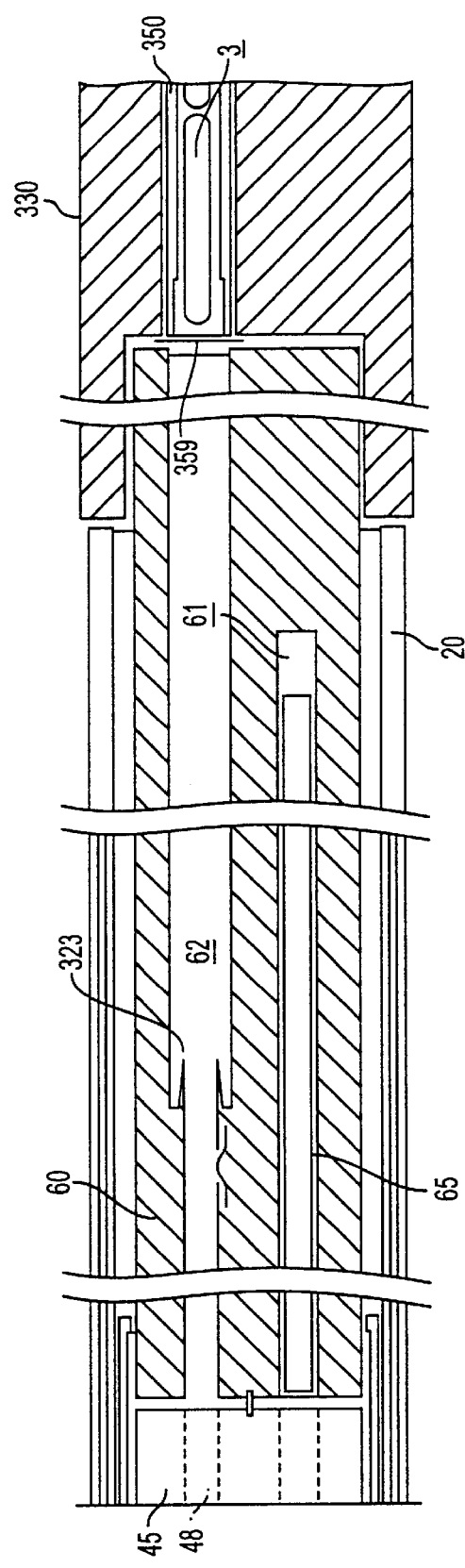
FIG. 31A is a segmented sectional view illustrating the film bayonet used to pierce a film dam associated with the seed cartridge during the loading of seeds into the fiberoptic-guided interstitial seed manual applicator shown in FIG. 30.
Figure 31B:
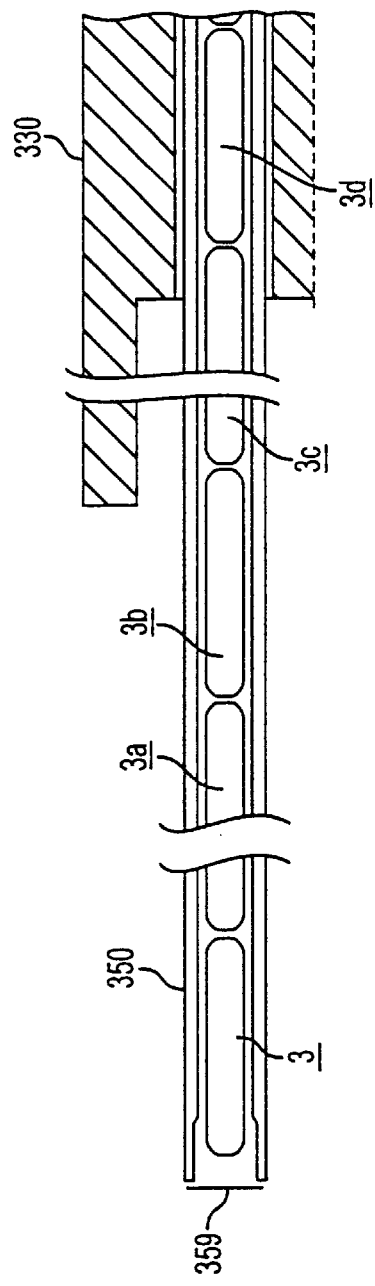
FIG. 31B is a segmented sectional view illustrating the advancement of a hollow push rod associated with the seed cartridge during the loading of seeds into the fiberoptic-guided interstitial seed manual applicator shown in FIG. 30.

When the seed cartridge 300 is releasably locked to the FOGISMA device 1 via the alignment adaptor 301, one of the seed channels 312 is in aligned relation (i.e., collinear) with the bore through the adaptor 301, the insertion port 81 and the seed alignment channel 62. In this manner, an elongated, hollow push rod 350 may be inserted longitudinally through the proximal end of the outer sleeve 330 and into the seed conduit 312 aligned with insertion port 81 and seed alignment channel 62. The seeds 3, 3a, . . . , 3n contained within that aligned conduit 312 are received within the hollow push rod 350. A first film dam 359 acts as a barrier to keep the seeds 3, 3a, . . . , 3n in end-to-end aligned position. A film bayonet 323 located within the seed alignment channel 62 may be used to tear or otherwise rupture the first film dam 359, thereby permitting the seeds 3, 3a, . . . , 3n to thereafter be ejected from the hollow push rod 350, as is illustrated in FIGS. 30, 31A and 31B.

Referring to FIG. 28, an elongated push rod or plunger 250 may be inserted through the hollow push rod 350 to advance the seeds 3, 3a, . . . , 31n contained therein out of the seed cartridge 300 and into the FOGISMA device 1. First and second tabs 351, 251 project upwardly from the hollow push rod 350 and seed plunger 360, respectively, each tab extending through the opening 320 associated with the seed conduit 312 in which the hollow push rod 350 and plunger 250 are received, as well as through the slot 335 of the outer sleeve 330. The tabs 351, 251 permit the surgeon or operator of the device 1 to grip and advance the push rod 350 or seed plunger 250 through the seed cartridge 300.

Figures 29E, 29F, 29G, 29H:
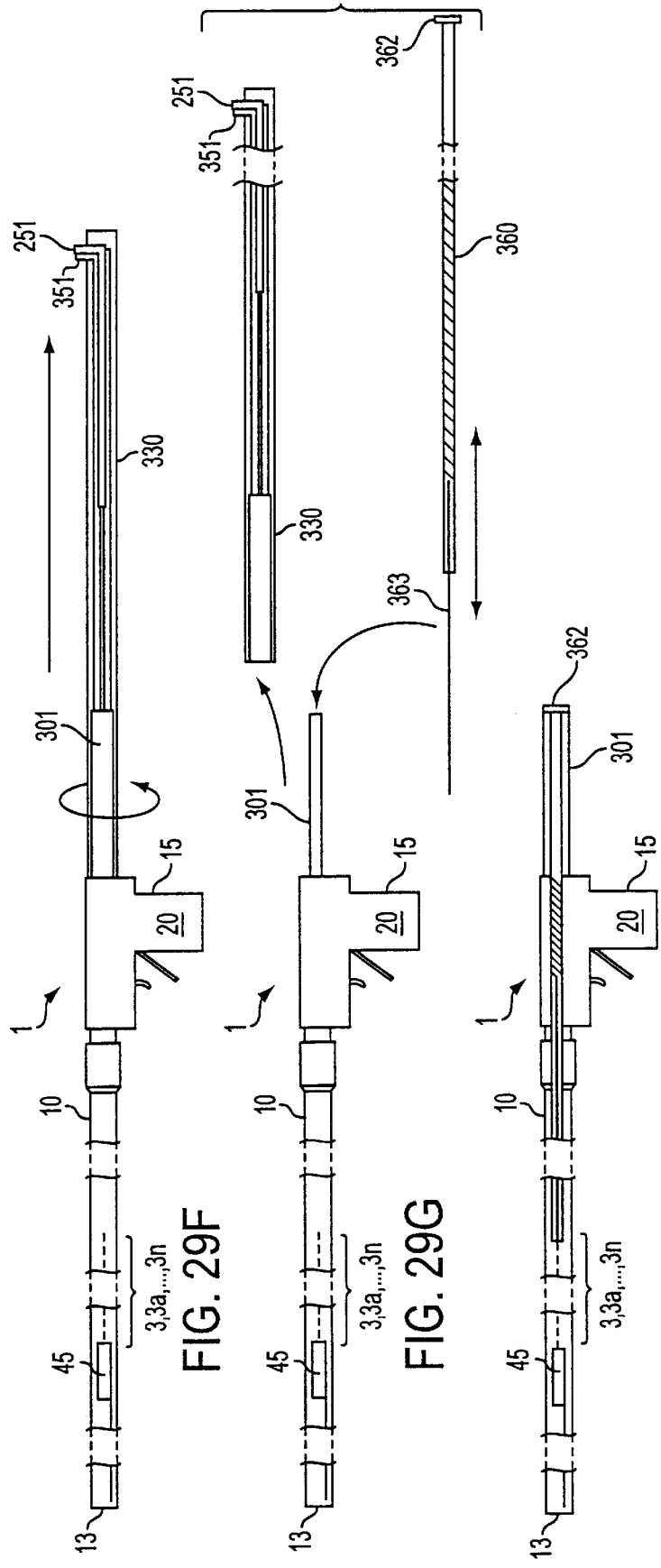

Thus, seeds 3, 3a, . . . , 3n contained within a particular seed conduit 312 of the inner core 310 may be advanced or loaded into the FOGISMA device 1 in the following manner as illustrated in FIGS. 29A–29H. In FIGS. 29A and 29B, a full pre-loaded seed cartridge 300 is operatively connected to the FOGISMA device 1 via the alignment adaptor 301 by the twist lock action described above.

Referring to FIG. 29C, after the assembled BISC seed cartridge 300 is operably connected to the device 1 (e.g., via alignment adaptor 301), the hollow push rod 350 is inserted longitudinally through the proximal end of the outer sleeve 330 and at least partially into the seed conduit 312 aligned with the insertion port 81 and alignment channel 62. The surgeon or operator of the device 1 is able to move the hollow push rod 350 longitudinally through the seed conduit 312 toward the FOGISMA device 1 by grasping the push rod tab 351 extending through opening 320 and slot 335. As the tab 351 advances distally, seeds 3, 3a, . . . , 3n advance in end-to-end aligned relation out of the seed cartridge 300, through the seed insertion port 81, and into the seed alignment channel 62 of the FOGISMA device 1.

The seed plunger or push rod 250 is then introduced through the second film dam 317 into the seed conduit 312 aligned with the insertion port 81 and alignment channel 62, as illustrated in FIG. 29D. The surgeon or operator of the device 1 is able to move the plunger 250 longitudinally through the seed conduit 312 toward the FOGISMA device 1 by grasping the push rod tab 251 extending through opening 320 and slot 335, as illustrated in FIG. 29E. In this position, the aligned seeds 3, 3a, . . . , 3n are longitudinally advanced through the seed alignment channel 62 toward the multichamber seed transfer barrel 45.

In FIG. 29F, the outer sleeve and inner core assembly is then disengaged from the adaptor 300 by removing the seed plunger 250, pulling back the hollow push rod 350 and rotating the outer sleeve 350 relative the adaptor 301 to release the slide lock. In FIG. 29G, the outer sleeve and inner core assembly has been removed from the adaptor 301 and the seed biasing mechanism 360 is inserted into the alignment adaptor 301, through the seed insertion port 81 and within the seed alignment channel 62 to bias the seeds 3 toward the seed transfer barrel 45.

Figure 32A:
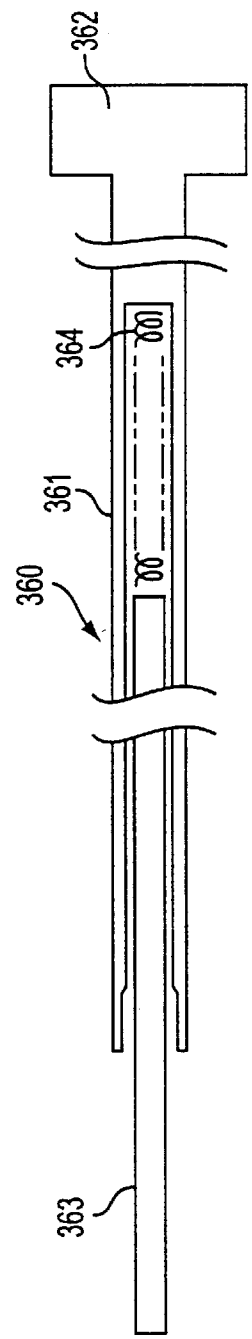
FIGS. 32 and 32A are longitudinal cross-sectional view of a seed biasing mechanism for use with the fiberoptic-guided interstitial seed manual applicator in accordance with the present invention.
Figure 32:
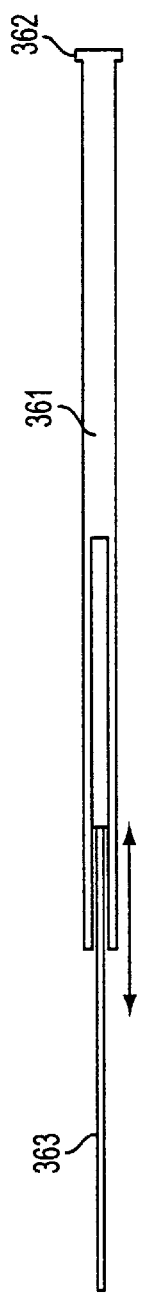

Once in place, a seed biasing mechanism 360 may be locked to the adaptor 301 in a manner similar to that described above with respect to seed biasing mechanism 70, and the FOGISMA device 1 is then fully loaded and ready to fire, as illustrated in FIG. 29H. Referring to FIGS. 32 and 32A, the seed biasing member 360 preferably comprises an elongated hollow body 361 that is closed on one end by a locking cap 362. An elongated piston 363 is slidingly received within the hollow body 361 and projects longitudinally through an opening in the distal end of the hollow body 361. A biasing member 364, such as a compression spring, is positioned within the hollow body 361 and biases the piston 363 away from the locking cap 362. In this manner, the seed biasing mechanism 360 biases the loaded seeds within the seed alignment channel 62 toward the multichamber seed transfer barrel 45.

It is understood that once the seeds 3, 3a, . . . , 3n are ejected from the BISC seed cartridge 300 into the seed alignment channel 62, the outer sleeve and inner core assembly 310, 330 may be removed from the device 1 and, if a greater number of seeds 3 are still required for the particular medical procedure, then the surgeon or operator of the device 1 may rotate the outer sleeve 330 to align a new seed conduit 312 (containing seeds 3) with the seed insertion port 81. The inner core/outer sleeve assembly may then be lockingly secured to the device 1 in the manner described above so that the new seed conduit 312 is in aligned relation to the seed insertion port 81 and seed alignment channel 62 of the FOGISMA device 1. The seeds 3, 3a, . . . , 3n contained in the newly aligned seed conduit 312 may be loaded into the FOGISMA device in the manner described above.

After the brachytherapy procedure has been completed, the physician or operator of the FOGISMA device 1 may discharge any unused seeds 3 remaining within the device 1 into the alignment adaptor/seed repository 301 of the BISC seed cartridge 300. FIG. 25 illustrates a longitudinal cross-sectional view of the seed repository 301 filled with unused seeds 3 that have been fired into it from the FOGISMA device 1 in preparation for their return to the seed distributor. This may be accomplished by first removing the alignment adaptor/seed repository 301 from the device 1 and thereafter firing the unused seeds 3 within the FOGISMA device 1 through a diaphragm 325 in the repository 301 that functions to keep the unused seeds 3 from spilling out of the seed repository 301.

Accordingly, a preloaded, self-contained BISC seed cartridge 200, 300 is provided for brachytherapy operators and adaptable for use with a host of implant applicators, including the FOGISMA device 1. The seed cartridge 200, 300 includes a protective outer sleeve 230, 330 for storing a pre-sterilized inner core 210, 310 containing the seeds 3. The easy-lock and unloading of the BISC seed cartridge 200, 300 facilitates implantation by: (1) preventing radioactive exposure to staff before the brachytherapy procedure; (2) ensuring a verified seed count; (3) eliminating the potential for seed spills or inadvertent loss due to seed manipulation in the brachytherapy hot room or operating suite; (4) efficient use of surgeon and operating room time by eliminating the need for autoclaving of the seeds/cartridge before use in the operating suite; (5) allowing rapid deposition of seeds, which are preloaded with many more seeds per cartridge than the standard number allowed by conventional seed magazines; and (6) limiting the potential for seed jamming or other misapplication through smooth mechanical action of seed loading cartridge.

Figure 33A:
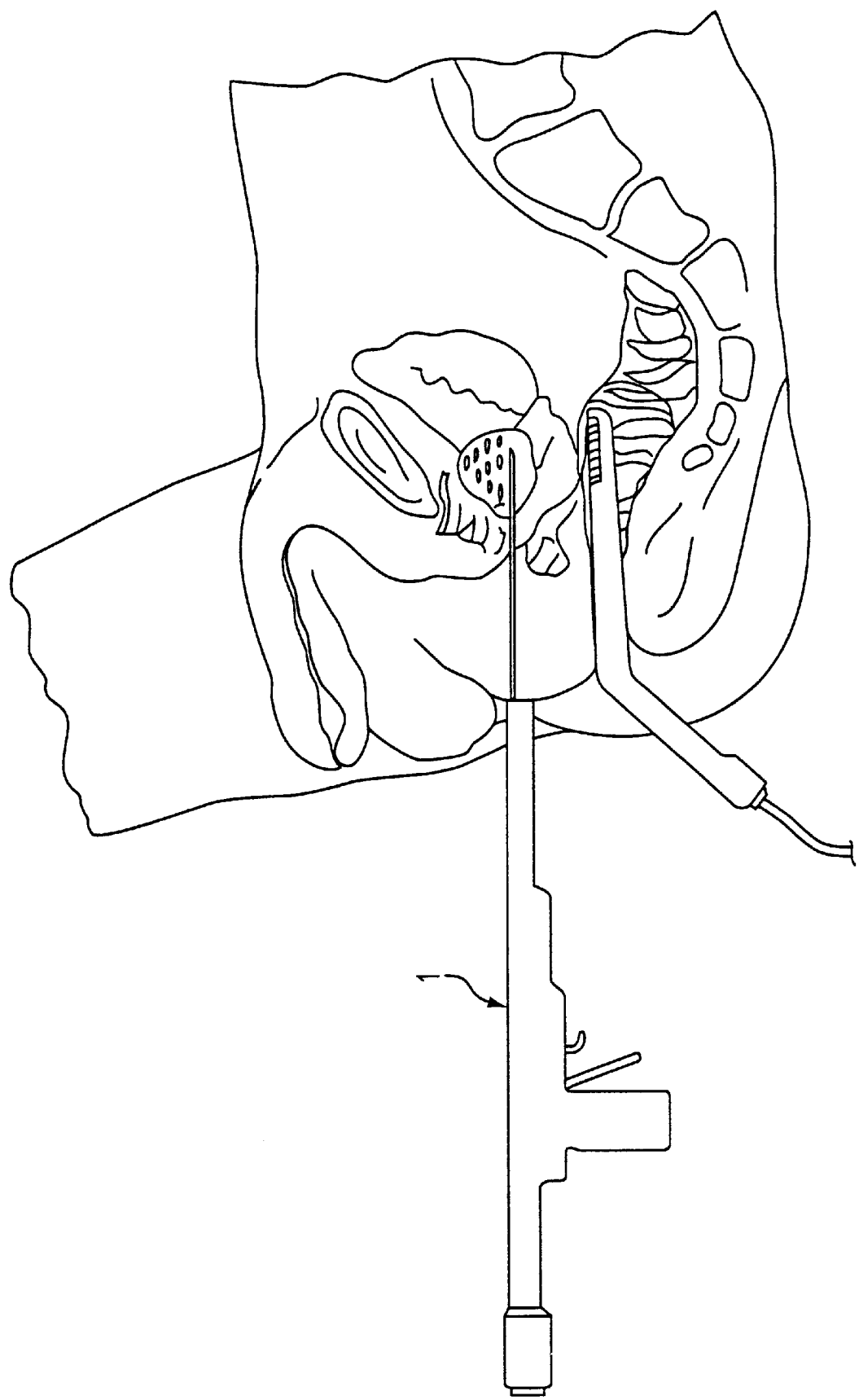
FIGS. 33A–33E illustrate various brachytherapy procedures accomplished using the fiberoptic-guided interstitial seed manual applicator in accordance with the present invention.

FIGS. 33A–33E are illustrative of some of brachytherapy procedures that may be accomplished using the FOGISMA device 1 in accordance with the present invention. FIG. 33A illustrates use of the device 1 for prostate brachytherapy using a minimal incision or no incision. An ultrasound transducer is also illustrated to assist the surgeon with the procedure.

Figure 33B:
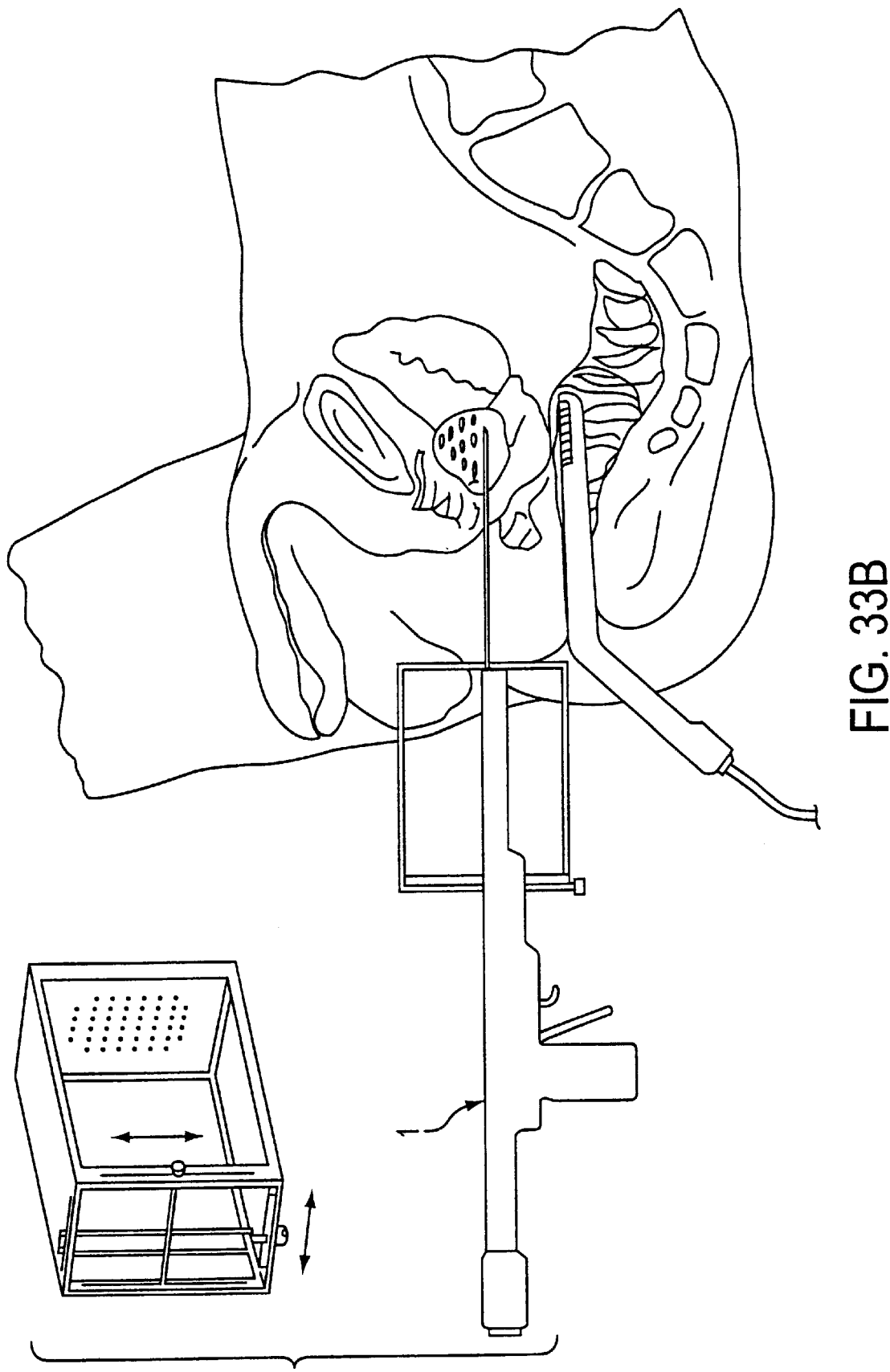

FIG. 33B also illustrates use of the FOGISMA device 1 for prostate brachytherapy using a minimal incision or no incision. However, unlike the preceding example, a conventional X-Y targeting grid may also be utilized to assist the surgeon in properly locating the FOGISMA device 1 relative to the implantation site.

Figure 33C:
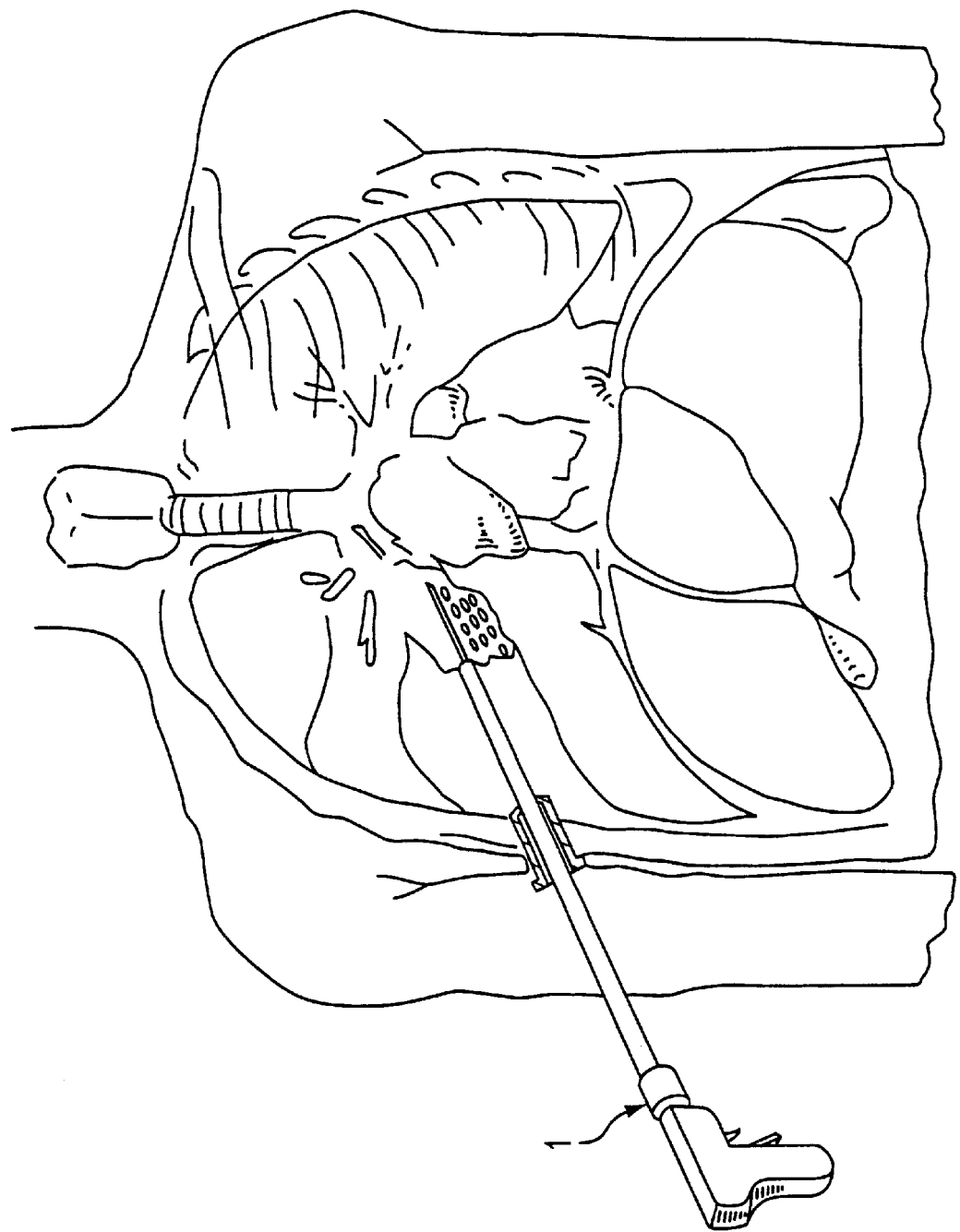
Figure 33D:
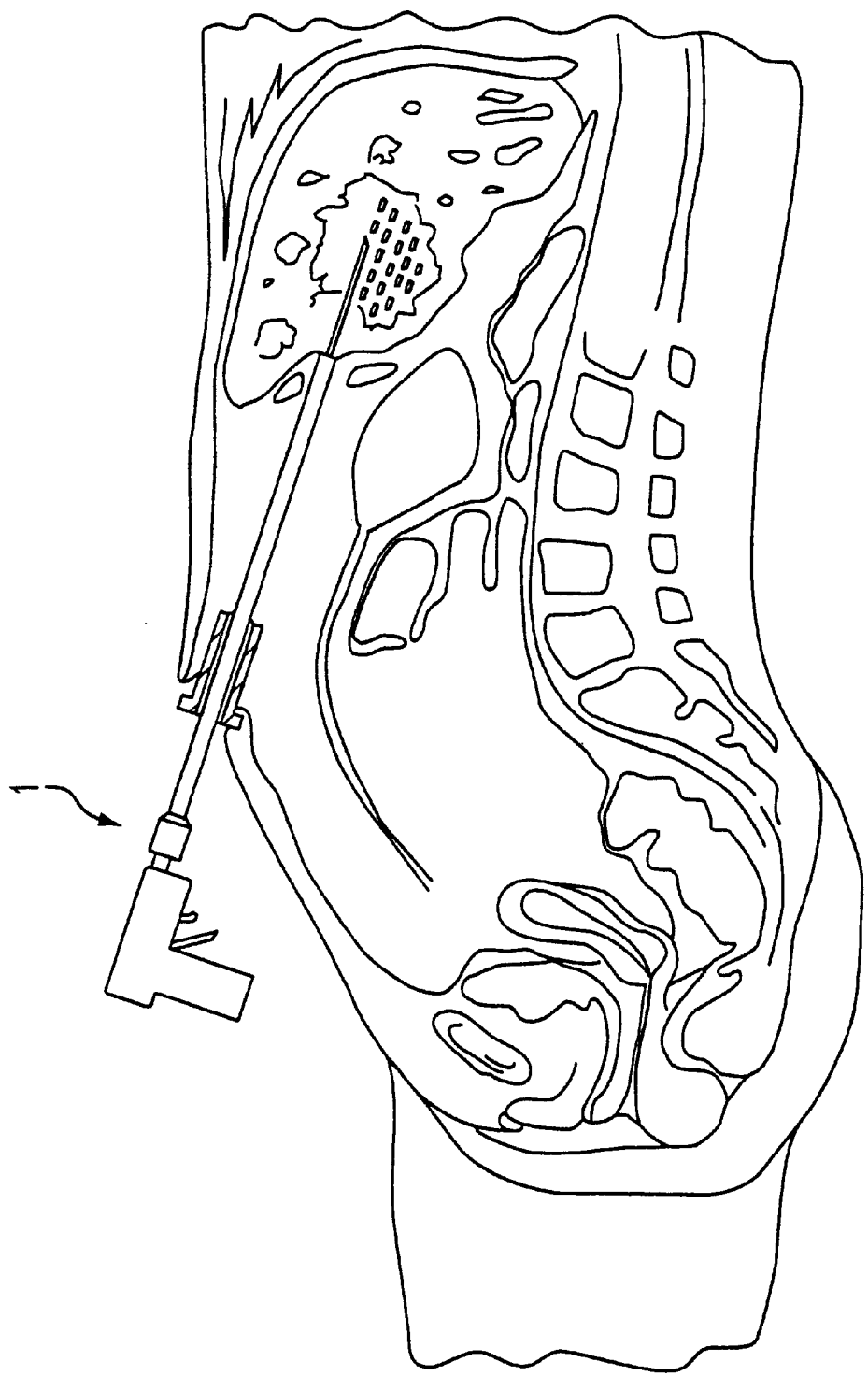
Figure 33E:
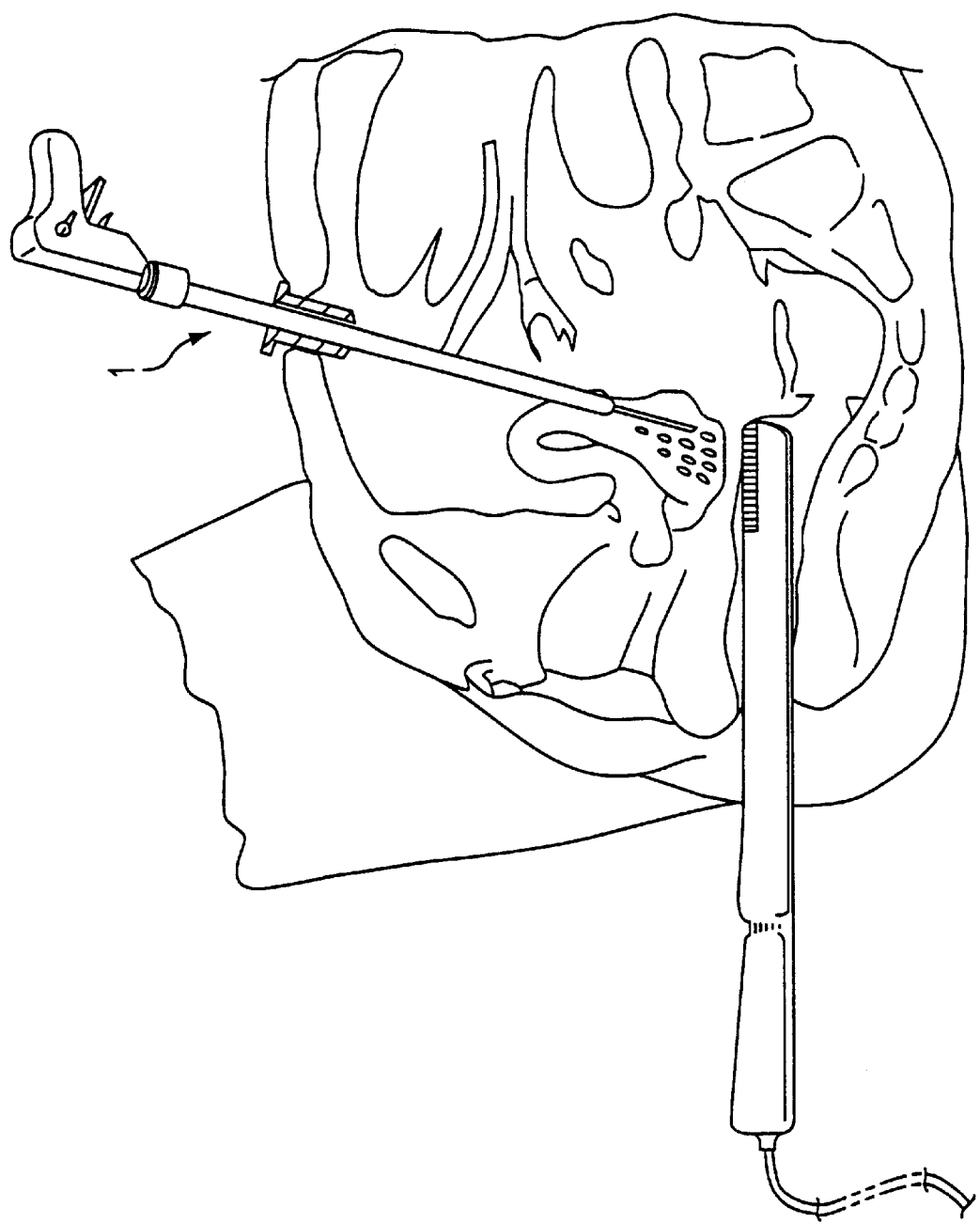

FIGS. 33C and 33D illustrate use of the FOGISMA device 1 for a minimally invasive brachytherapy treatment associated with lung cancer. Similarly, FIG. 33E illustrates use of the device 1 for a minimally invasive brachytherapy treatment associated with cervical cancer. An ultrasound transducer is also illustrated to assist the surgeon with the procedure.

The data presented below accentuates the need for the present invention. In 1995, it was estimated that 24,000 cases of pancreatic cancer would be diagnosed and at least that number of patients would die of the disease. Ten to fifteen percent of all patients (approximately 3,000) are treated surgically. For those patients having a tumor at the surgical margins, brachytherapy could be used intraoperatively. The other two-thirds of the cases (approximately 16,000 patients) were inoperable at the time of presentation and would typically be referred for radiotherapy following establishment of a tissue diagnosis. Previously, open biopsy and simultaneous seed implantation were performed on selected cases and the results in small series with the open implant procedure were encouraging. With the advent of CT-guided needle biopsies virtually replacing open incisional biopsies, a need exists for a non-invasive or minimally invasive surgical implantation device such as that in accordance with the present invention that would allow simultaneous CT-guided needle biopsy and implantation of the tumor.

In addition, more than 50% of the 200,000 patients having GI malignancies develop liver metastases, in addition to the 18,500 per year who are diagnosed with primary hepatobiliary tumors. In some circumstances, patients with solitary liver lesions may be candidates for surgical resection. However, in instances where the patient is medically unfit for laparotomy, or a lesion is technically unresectable, a non-invasive or minimally invasive surgical implantation device such as that in accordance with the present invention for interstitial brachytherapy would be desirable. The same principles may be applied to patients having a finite number of intrahepatic lesions, with less potential for uncontrolled bleeding in comparison to resection.

Furthermore, despite the fact that cervical cancer is the number one cause of cancer death in women worldwide, the advent of the Pap smear has cut the annual incidence in the U.S. to approximately 15,000 patients. Fully half of those patients with advanced disease (approximately 4,000 women) will fail radiation treatment. Many develop pelvic intraperitoneal recurrences that may be exceedingly difficult to resect if surgery is attempted. Laparoscopic exploration and transabdominal brachytherapy implantation using a non-invasive or minimally invasive surgical implantation device such as that in accordance with the present invention would be desirable for salvage in these patients.

Also, it was estimated in 1995 that there were 170,000 lung cancers diagnosed in the U.S., with only 5% of those diagnosed patients surviving five years. There are 34,000 cases of small cell lung cancer that are usually treated with chemotherapy. Of the 136,000 non-small cell cancer patients, approximately 40,000 are surgically resected. The remainder of the non-small cell cancer patients (approximately 96,000) require irradiation. Overall, more than 50% of patients (more than approximately 67,500) treated surgically or with radiation die from the effects of their intrathoracic disease. Reoperation for recurrence after surgery is seldom (if ever) performed. Reirradiation with external beam therapy of recurrent disease in the chest carries many risks, including further exposure of the spinal cord to doses possibly exceeding tolerance levels and inclusion of portions of precious remaining functional lung in the treatment fields. Transthoracic implantation using a non-invasive or minimally invasive surgical implantation device such as that in accordance with the present invention is a desirable option for salvage in the more than 67,500 patients with recurrences and should be explored as a means of boosting the dose of radiation in the 96,000 patients who receive radiotherapy as their initial treatment, with the overall applicability exceeding 100,000 cases per year.

Furthermore, it was also estimated that more than 50,000 urinary bladder cancers would be diagnosed in 1995. Although the disease is localized to the bladder in 90% of patients, as many as 80% develop recurrences. Cystoscopy and/or laparoscopy-guided interstitial implantation using a non-invasive or minimally invasive surgical implantation device such as that in accordance with the present invention is desirable for those patients with muscle-invasion disease. The precedent for successful brachytherapy in bladder cancer was set by Dutch investigators who placed needles into the bladder and surrounding tissue through laparotomy incisions. However, various problems, including the need to reopen some patients to extricate stuck needles and impaired wound healing, led to the virtual abandonment of brachytherapy in this organ. A non-invasive or minimally invasive surgical implantation device such as that in accordance with the present invention is desirable option for the radiotherapy and urologic communities, eliminating the problems encountered by users of the older implantation technique while duplicating its successful results in a patient population approaching 36,000 per year.

Additionally, the therapeutic approach to organ-confined prostate cancer remains controversial. It was estimated that 250,000 men would be diagnosed with this disease in 1995, many via the PSA blood test. As a result of the many advances in transrectal ultrasound, radioisotope availability, and computer modelling of dose distribution of implanted seeds, prostate implants have again become popular. They were initially accomplished through a laparotomy incision using a retropubic approach beginning in the early 1970's, but were abandoned because technical limitations prevented consistency in implanting seeds in an effective pattern. Nowadays, prostate implants have reemerged as an accepted modality with superb results. They are performed via the transperineal route, though conventional instrumentation is primitive by today's standards. It is estimated that there are approximately 200 centers performing more than 2,000 prostate implants per year. It must be recognized that, in this era of cost containment, prostate brachytherapy offers the most rapid, least morbid, least expensive, and possibly most effective method of treatment for early stage cancer, i.e. 40% of all patients (100,000). A safe, precise and convenient non-invasive or minimally invasive surgical implantation device such as that in accordance with the present invention for brachytherapy is desirable for treatment of these patients. Such treatment would represent a 5,000% nationwide increase in prostate brachytherapy, thus thrusting prostate brachytherapy into the lead in the therapy of early prostate cancer.

The American Brachytherapy Society membership represents radiation oncologists who have a dedicated interest in implantable radionuclides for cancer control. Results of its survey of brachytherapy facilities published in 1994 show that, among 1,321 radiation oncology centers nationwide, 78% of those responding perform some brachytherapy. Fifty-one percent of responding centers practice interstitial brachytherapy.

The indications for utilization of a manual interstitial brachytherapy system wedded to the latest technology in laparoscopic guidance in accordance with the present invention are seemingly boundless. This is a technology having broad applications and unlimited therapeutic benefits. In addition to the organ systems mentioned above, some or all aspects of this technology may be applicable to tumors of the upper aerodigestive tract, rectum, ovary, kidney, and brain.

Although illustrative preferred embodiments have been described herein in detail, it should be noted and will be appreciated by those skilled in the art that numerous variations may be made within the scope of this invention without departing from the principle of this invention and without sacrificing its chief advantages. The terms and expressions have been used herein as terms of description and not terms of limitation. There is no intention to use the terms or expressions to exclude any equivalents of features shown and described or portions thereof and this invention should be defined in accordance with the claims which follow.

We claim:

1. An implantation device for implanting seeds within or adjacent to a target area, such as a tumor, located within a patient, comprising:

an implantation needle having a bore extending longitudinally therethrough from a proximal end to a distal end of the needle, the needle bore being adapted to permit at least one seed to pass therethrough;

an elongated plunger extending longitudinally through the implantation device, the plunger being in aligned relation to the needle bore and being selectively movable in the longitudinal direction relative the needle from a retracted position spaced apart from the needle to an extended position wherein the plunger is advanced through the needle bore to eject at least one of the seeds through the bore, out of the distal end of needle and into the target area;

an outer sheath;

an optical device carried by and operatively connected to the implantation device, the optical device providing visual assistance to an operator of the implantation device to guide and verify implantation of the ejected seed into the target area; and an elongated inner sheath located within the outer sheath, the inner sheath substantially enclosing the plunger and at least a portion of the needle, wherein the optical device is at least temporarily positioned within the implantation device adjacent the distal end of the needle, and wherein the optical device is carried by and operatively connected to the plunger so that when the plunger is selectively moved to the extended position, the optical device is carried by the plunger through the needle bore to a position proximate the distal end of the needle.

2. An implantation device for implanting seeds within or adjacent to a target area, such as a tumor, located within a patient, comprising:

an implantation needle having a bore extending longitudinally therethrough from a proximal end to a distal end of the needle, the needle bore being adapted to permit at least one seed to pass therethrough;

an elongated plunger extending longitudinally through the implantation device, the plunger being in aligned relation to the needle bore and being selectively movable in the longitudinal direction relative the needle from a retracted position spaced apart from the needle to an extended position wherein the plunger is advanced through the needle bore to eject at least one of the seeds through the bore, out of the distal end of needle and into the target area;

an optical device carried by and operatively connected to the implantation device, the optical device providing visual assistance to an operator of the implantation device to guide and verify implantation of the ejected seed into the target area; and a seed biasing member positioned within a seed alignment channel and adapted to bias the seeds aligned within the seed alignment channel in a direction toward a seed chamber aligned with the seed alignment channel;

an elongated member having a seed alignment channel extending longitudinally therethrough, the seed alignment channel adapted to retain the seeds in end-to-end aligned relation within the implantation device;

a seed transfer barrel having at least one seed chamber adapted to receive a single seed, the seed chamber being selectively movable from a loading position in aligned relation and communicating with the seed alignment channel to a firing position in aligned relation to the needle and the plunger, wherein, in the loading position, a single seed may be advanced from the seed alignment channel into the seed chamber, and, in the firing position, the plunger may be selectively advanced through the seed chamber to eject the seed contained within the seed chamber out of the transfer barrel, through the needle bore and into the target area as the plunger moves from the retracted position to the extended position, wherein the optical device is at least temporarily positioned within the implantation device adjacent the distal end of the needle, and wherein the optical device is carried by and operatively connected to the plunger so that when the plunger is selectively moved to the extended position, the optical device is carried by the plunger through the needle bore to a position proximate the distal end of the needle.

3. An implantation device for implanting seeds within or adjacent to a target area, such as a tumor, located within a patient, comprising:

an implantation needle having a bore extending longitudinally therethrough from a proximal end to a distal end of the needle, the needle bore being adapted to permit at least one seed to pass therethrough;

an elongated plunger extending longitudinally through the implantation device, the plunger being in aligned relation to the needle bore and being selectively movable in the longitudinal direction relative the needle from a retracted position spaced apart from the needle to an extended position wherein the plunger is advanced through the needle bore to eject at least one of the seeds through the bore, out of the distal end of needle and into the target area;

an optical device carried by and operatively connected to the implantation device, the optical device providing visual assistance to an operator of the implantation device to guide and verify implantation of the ejected seed into the target area; and an elongated outer sheath substantially enclosing the plunger, wherein the outer sheath is selectively movable in predetermined increments in the longitudinal direction relative the needle;

a housing located at a proximal end of the outer sheath; and means for selectively moving the outer sheath in predetermined increments in the longitudinal direction relative the housing, wherein the means for selectively moving the outer sheath comprises a roticulator ring operably connecting the proximal end of the outer sheath to the housing, wherein the optical device is at least temporarily positioned within the implantation device adjacent the distal end of the needle, and wherein the optical device is carried by and operatively connected to the plunger so that when the plunger is selectively moved to the extended position, the optical device is carried by the plunger through the needle bore to a position proximate the distal end of the needle.

4. The implantation device according to claim 3, further comprising indicia formed on the roticulator ring to provide a visual indication of the selective movement of the outer sheath relative the housing.

5. An implantation device for implanting seeds within or adjacent to a target area, such as a tumor, located within a patient, comprising:

an implantation needle having a bore extending longitudinally therethrough from a proximal end to a distal end of the needle, the needle bore being adapted to permit at least one seed to pass therethrough;

an elongated plunger extending longitudinally through the implantation device, the plunger being in aligned relation to the needle bore and being selectively movable in the longitudinal direction relative the needle from a retracted position spaced apart from the needle to an extended position wherein the plunger is advanced through the needle bore to eject at least one of the seeds through the bore, out of the distal end of needle and into the target area;

an optical device carried by and operatively connected to the implantation device, the optical device providing visual assistance to an operator of the implantation device to guide and verify implantation of the ejected seed into the target area;

an elongated outer sheath substantially enclosing the plunger, wherein the outer sheath is selectively movable in predetermined increments in the longitudinal direction relative the needle;

a housing located at a proximal end of the outer sheath;

means for selectively moving the outer sheath in predetermined increments in the longitudinal direction relative the housing; and indicia formed on the housing to provide a visual indication of the selective movement of the outer sheath relative the housing, wherein the optical device is at least temporarily positioned within the implantation device adjacent the distal end of the needle, and wherein the optical device is carried by and operatively connected to the plunger so that when the plunger is selectively moved to the extended position, the optical device is carried by the plunger through the needle bore to a position proximate the distal end of the needle, wherein the means for selectively moving the outer sheath comprises:

a control lever carried by the housing, the control lever having a plurality of gear teeth formed thereon for driving at least one gear rotatably mounted within the housing; and a plurality of gear teeth formed on at least a portion of the outer sheath for interlocking engagement with the at least one gear, wherein rotation of the at least one gear in response to actuation of the control lever causes the outer sheath to move longitudinally relative the housing.

6. An implantation device for implanting seeds within or adjacent to a target area, such as a tumor, located within a patient, comprising:

an implantation needle having a bore extending longitudinally therethrough from a proximal end to a distal end of the needle, the needle bore being adapted to permit at least one seed to pass therethrough;

an elongated plunger extending longitudinally through the implantation device, the plunger being in aligned relation to the needle bore and being selectively movable in the longitudinal direction relative the needle from a retracted position spaced apart from the needle to an extended position wherein the plunger is advanced through the needle bore to eject at least one of the seeds through the bore, out of the distal end of needle and into the target area;

an optical device carried by and operatively connected to the implantation device, the optical device providing visual assistance to an operator of the implantation device to guide and verify implantation of the ejected seed into the target area;

a removable seed cartridge adapted to hold a plurality of seeds for use with the implantation device, the seed cartridge having a proximal end and a distal end, the distal end being releasably connected to the implantation device for feeding the seeds into the seed alignment channel from the seed cartridge;

an elongated member having a seed alignment channel extending longitudinally therethrough, the seed alignment channel adapted to retain the seeds in end-to-end aligned relation within the implantation device;

a seed transfer barrel having at least one seed chamber adapted to receive a single seed, the seed chamber being selectively movable from a loading position in aligned relation and communicating with the seed alignment channel to a firing position in aligned relation to the needle and plunger, wherein, in the loading position, a single seed may be advanced from the seed alignment channel into the seed chamber, and, in the firing position, the plunger may be selectively advanced through the seed chamber to eject the seed contained within the seed chamber out of the transfer barrel, through the needle bore and into the target area at the plunger moves from the retracted position to the extended position, wherein the optical device is at least temporarily positioned within the implantation device adjacent the distal end of the needle, and wherein the optical device is carried by and operatively connected to the plunger so that when the plunger is selectively moved to the extended position, the optical device is carried by the plunger through the needle bore to a position proximate the distal end of the needle.

7. The implantation device according to claim 6, wherein the seed cartridge comprises:

an elongated cylindrically-shaped core member having a seed conduit extending longitudinally therethrough, the seed conduit being in aligned relation to and communication with the seed alignment channel when the seed cartridge is releasably connected to the implantation device and the seed conduit being adapted to retain the plurality of seeds in end-to-end aligned relation prior to feeding the seeds into the seed alignment channel; and an elongated seed advancement push rod slidably received within the seed conduit, wherein longitudinal movement of the push rod toward the distal end of the seed cartridge causes the seeds contained within the seed conduit to advance into the seed alignment channel from the seed cartridge.

8. The implantation device according to claim 7, wherein the seed cartridge comprises at least one locking key projecting from the distal end of the seed cartridge, the locking key being received within one of a plurality of keyholes formed within a housing of the implantation device to releasably connect the seed cartridge to the implantation device, wherein the core member includes a plurality of substantially parallel, spaced apart seed conduits extending longitudinally therethrough, each seed conduit being adapted to retain a plurality of seeds in end-to-end aligned relation prior to feeding the seeds into the seed alignment channel, the core member having a plurality of substantially parallel, spaced apart circumferential slots formed therein and extending longitudinally throughout the length of the core member, each slot opening into one of the seed conduits, and the seed cartridge adapted to be releasably connected to the implantation device so that any one of the seed conduits is in aligned relation to and communication with the seed alignment channel when the seed cartridge is releasably connected to the implantation device, and wherein the core comprises a circumferential slot extending longitudinally throughout the length of the core member, the slot opening into the seed conduit; and wherein the push rod comprises a tab projecting therefrom that extends through the circumferential slot so that an operator of the implantation device may grip the tab to advance the push rod longitudinally through the seed conduit.

9. The implantation device according to claim 6, wherein the seed cartridge comprises a locking key projecting from the distal end of the seed cartridge, the locking key being received within a keyhole formed within a housing of the implantation device to releasably connect the seed cartridge to the implantation device.

10. An implantation device for implanting seed within or adjacent to a target area, such as a tumor, located within a patient, comprising:

an implantation needle having a bore extending therethrough along the first longitudinal axis from a proximal end to a distal end of the needle, the needle bore being adapted to permit at least one seed to pass therethrough;

an elongated member having a seed alignment channel extending along a second axis, the seed alignment channel adapted to retain the seeds in aligned relation within the implantation device prior to selectively advancing at least one of the seeds retained therein into aligned relation with the needle bore along the first axis;

an elongated plunger extending through the implantation device along the first longitudinal axis, the plunger being in aligned relation to the needle bore and being selectively movable in the longitudinal direction relative the needle from a retracted position spaced apart from the needle to an extended position wherein the plunger is advanced through the needle bore to eject at least one of the seeds aligned with the needle bore along the first axis through the bore, out of the distal end of needle and into the target area;

an elongated outer sheath substantially enclosing the plunger, wherein the outer sheath is selectively movable in predetermined increments in the longitudinal direction along the first axis relative the needle; and an elongated inner sheath located within the outer sheath, the inner sheath substantially enclosing the plunger and at least a portion of the needle.

* * * * *